United States Patent
Reeve et al.

(10) Patent No.: US 7,370,021 B2
(45) Date of Patent: May 6, 2008

(54) MEDICAL APPLICATIONS OF ADAPTIVE LEARNING SYSTEMS USING GENE EXPRESSION DATA

(75) Inventors: Anthony Edmund Reeve, Dunedin (NZ); Mathias Erwin Futschik, Dunedin (NZ); Michael James Sullivan, Christchurch (NZ); Nikola Kirilov Kasabov, Auckland (NZ); Parry John Guilford, Dunedin (NZ)

(73) Assignee: Pacific Edge Biotechnology Ltd., Dunedin (NZ)

( * ) Notice: Subject to any disclaimer, the term of this patent is extended or adjusted under 35 U.S.C. 154(b) by 370 days.

(21) Appl. No.: 10/507,737

(22) PCT Filed: Mar. 17, 2003

(86) PCT No.: PCT/NZ03/00045

§ 371 (c)(1),
(2), (4) Date: Sep. 15, 2004

(87) PCT Pub. No.: WO03/079286

PCT Pub. Date: Sep. 25, 2003

(65) Prior Publication Data

US 2005/0256815 A1 Nov. 17, 2005

(30) Foreign Application Priority Data

Mar. 15, 2002 (NZ) ..................................... 517817

(51) Int. Cl.
*G06E 1/00* (2006.01)
*G06E 3/00* (2006.01)
*G06F 15/18* (2006.01)
*G06G 7/00* (2006.01)

(52) U.S. Cl. ....................................................... 706/16

(58) Field of Classification Search ............ 706/15–16, 706/45–47
See application file for complete search history.

(56) References Cited

U.S. PATENT DOCUMENTS

| | | | | |
|---|---|---|---|---|
| 5,579,439 A | * | 11/1996 | Khan | 706/2 |
| 5,727,130 A | * | 3/1998 | Hung | 706/13 |
| 5,790,761 A | * | 8/1998 | Heseltine et al. | 706/16 |
| 6,493,637 B1 | * | 12/2002 | Steeg | 702/19 |
| 6,714,925 B1 | * | 3/2004 | Barnhill et al. | 706/48 |
| 6,760,715 B1 | * | 7/2004 | Barnhill et al. | 706/16 |

(Continued)

OTHER PUBLICATIONS

Gene selection and cancer classification using a fuzzy neural network Feng Chu; Wei Xie; Lipo Wang; Fuzzy Information, 2004. Processing NAFIPS '04. IEEE Annual Meeting of the vol. 2, Jun. 27-30, 2004 pp. 555-559 vol. 2 Digital Object Identifier 10.1109/NAFIPS.2004.1337361.*

(Continued)

*Primary Examiner*—Michael B Holmes
(74) *Attorney, Agent, or Firm*—D. Benjamin Borson

(57) ABSTRACT

A neural network module is provided. It comprises an input layer comprising one or more input nodes configured to receive gene expression data. It also has a rule base layer comprising one or more rule nodes and an output layer comprising one or more output nodes configured to output one or more conditions. It also comprises an adaptive component configured to extract one or more rules from the rule base layer representing relationships between the gene expression data and the one or more conditions. Methods and systems using the module are disclosed as well as specific profiles utilising the system.

40 Claims, 34 Drawing Sheets

U.S. PATENT DOCUMENTS

| | | | |
|---|---|---|---|
| 6,789,069 B1* | 9/2004 | Barnhill et al. | 706/12 |
| 6,882,990 B1* | 4/2005 | Barnhill et al. | 706/16 |
| 6,925,389 B2* | 8/2005 | Hitt et al. | 702/19 |
| 6,980,974 B2* | 12/2005 | Kobayashi et al. | 706/21 |
| 7,003,403 B1* | 2/2006 | Dougherty et al. | 702/19 |
| 7,062,076 B1* | 6/2006 | Osborne et al. | 382/128 |
| 7,089,217 B2* | 8/2006 | Kasabov | 706/12 |
| 7,096,206 B2* | 8/2006 | Hitt | 706/12 |
| 7,117,185 B1* | 10/2006 | Aliferis et al. | 706/12 |
| 7,117,188 B2* | 10/2006 | Guyon et al. | 706/20 |
| 7,240,038 B2* | 7/2007 | Hitt | 706/12 |
| 7,257,563 B2* | 8/2007 | Shmulevich et al. | 706/15 |

OTHER PUBLICATIONS

A graphical operating environment for neural network expert systems Quah, T.S.; Tan, C.L.; Teh, H.H.; Neural Networks, 1991. 1991 IEEE International Joint Conference on Nov. 18-21, 1991 pp. 684-689 vol. 1 Digital Object Identifier 10.1109/IJCNN.1991.170479.*

Drosophila Grail: an intelligent system for gene recognition in Drosophila DNA sequences Ying Xu; Helt, G.; Einstein, J.R.; Rubin, G.; Uberbacher, E.C.; Intelligence in Neural and Biological Systems, 1995. INBS'95, Proceedings., First International Symposium on May 29-31, 1995 pp. 128-135 Digital Object Identifier 10.1109/INBS.1995.404269.*

Finding Compact Classification Rules With Parsimonious Gene Expression Programming Weihong Wang; Qu Li; Zhihua Cai; Neural Networks and Brain, 2005. ICNN&B '05. International Conference on vol. 2, Oct. 13-15, 2005 pp. 702-705 Digital Object Identifier 10.1109/ICNNB.2005.1614725.*

Accurate Cancer Classification Using Expressions of Very Few Genes Wang Lipo ; Chu Feng ; Xie Wei ; IEEE/ACM Transactions on Computational Biology and Bioinformatics : Accepted for future publication vol. PP, Issue 99, 2007 p. 1-1 Digital Object Identifier 10.1109/tcbb.2007.1006.*

Bioinformatics with soft computing Mitra, S.; Hayashi, Y.; Systems, Man and Cybernetics, Part C, IEEE Transactions on vol. 36, Issue 5, Sep. 2006 pp. 616-635 Digital Object Identifier 10.1109/TSMCC.2006.879384.*

Uncertainty of data, fuzzy membership functions, and multilayer perceptrons Duch, W.; Neural Networks, IEEE Transactions on vol. 16, Issue 1, Jan. 2005 pp. 10-23 Digital Object Identifier 10.1109/TNN.2004.836200.*

Characterizing human gene splice sites using evolved regular expressions Jing-Jing Li; De-Shuang Huang; MacCallum, R.M.; Xiao-Run Wu; Neural Networks, 2005. IJCNN '05. Proceedings. 2005 IEEE International Joint Conference on vol. 1, Jul. 31-Aug. 4, 2005 pp. 493-498 vol. 1 Digital Object Identifier 10.1109/IJCNN.2005.1555880.*

Genes IV: A bit-serial processing element for a built-model neural-network accelerator Ienne, P.; Viredaz, M.A.; Application-Specific Array Processors, 1993. Proceedings., International Conference on Oct. 25-27, 1993 pp. 345-356 Digital Object Identifier 10.1109/ASAP.1993.397157.*

Genetic algorithm/neural network synergy for nonlinearly constrained optimization problems Shonkwiler, R.; Miller, K.R.; Combinations of Genetic Algorithms and Neural Networks, 1992. Cogann-92. International Workshop on Jun. 6, 1992 pp. 248-257 Digital Object Identifier 10.1109/COGANN.1992.273935.*

Bioinformatics: a knowledge engineering approach Kasabov, N.; Intelligent Systems, 2004. Proceedings. 2004 2nd International IEEE Conference vol. 1, Jun. 22-24, 2004 pp. 19-24 vol. 1.*

Splice-junction recognition on gene sequences (DNA) by Brain learning algorithm Rampone, S.; Neural Networks Proceedings, 1998. IEEE World Congress on Computational Intelligence. The 1998 IEEE International Joint Conference on vol. 1, May 4-9, 1998 pp. 774-779 vol. 1 Digital Object Identifier 10.1109/IJCNN.1998.682379.*

An evolution of cellular automata neural systems using DNA coding method Dong-Wook Lee; Kwee-Bo Sim; Fuzzy Systems Conference Proceedings, 1999. FUZZ-IEEE '99. 1999 IEEE International vol. 1, Aug. 22-25, 1999 pp. 117-122 vol. 1 Digital Object Identifier 10.1109/FUZZY.1999.793217.*

Synthesis of self-replication cellular automata using genetic algorithms Kajisha, H.; Saito, T.; Neural Networks, 2000. IJCNN 2000, Proceedings of the IEEE-INNS-ENNS International Joint Conference on vol. 5, Jul. 24-27, 2000 pp. 173-177 vol. 5 Digital Object Identifier 10.1109/IJCNN.2000.861453.*

A method for modelling genetic regulatory networks by using evolving connectionist systems and microarray gene expression data Kasabov, N.K.; Dimitrov, D.S.;Neural Information Processing, 2002. ICONIP '02. Proceedings of the 9th International Conference on vol. 2, Nov. 18-22, 2002 pp. 596-601 vol. 2 Digital Object Identifier 10.1109/I.*

An efficient heuristic-based evolutionary algorithm for solving constraint satisfaction problems Tam, V.; Stuckey, P.; Intelligence and Systems, 1998. Proceedings., IEEE International Joint Symposia on May 21-23, 1998 pp. 75-82 Digital Object Identifier 10.1109/IJSIS.1998.685421.*

On Classification Models of Gene Expression Microarrays: The Simpler the Better Pranckeviciene, E.; Somorjai, R.; Neural Networks, 2006. IJCNN '06. International Joint Conference on Jul. 16-21, 2006 pp. 3572-3579.*

Gene classification using expression profiles: a feasibility study Kuramochi, M.; Karypis, G.; Bioinformatics and Bioengineering Conference, 2001. Proceedings of the IEEE 2nd International Symposium on Nov. 4-6, 2001 pp. 191-200 Digital Object Identifier 10.1109/BIBE.2001.974429.*

Self-organizing neural networks for efficient clustering of gene expression data Ji He; Ah-Hwee Tan; Chew-Lim Tan; Neural Networks, 2003. Proceedings of the International Joint Conference on vol. 3, Jul. 20-24, 2003 pp. 1684-1689 vol. 3 Digital Object Identifier 10.1109/IJCNN.2003.1223660.*

A computational approach to reconstructing gene regulatory networks Deng, X.; Ali, H.; Bioinformatics Conference, 2003. CSB 2003. Proceedings of the 2003 IEEE Aug. 11-14, 2003 pp. 413-414 Digital Object Identifier 10.1109/CSB.2003.1227350.*

* cited by examiner

MEDICAL APPLICATIONS OF ADAPTIVE LEARNING SYSTEMS USING GENE EXPRESSION DATA

FIELD OF THE INVENTION

The invention relates to medical applications of adaptive learning systems using gene expression data, including but not limited to methodologies for disease profiling and gene expression profiling.

BACKGROUND TO INVENTION

Many diseases and disorders, such as cancer, have very complex genetic and phenotypic abnormalities and an unpredictable biological behaviour. The cancer cell represents the end-point of successive generations of clonal cell evolution, multiple gene mutations, genomic instability, and erroneous gene expression.

The biological behaviour of cancer is determined by multiple factors, most importantly the biological characteristics of the individual cancer, but also the biology of the patient such as age, sex, race, genetic constitution and the like, and the location of the cancer. This biological aud genetic complexity of cancer means that any individual cancer may follow an unpredictable clinical course, with an uncertain outcome for the patient.

Where multiple treatment options are available for a particular cancer, it is necessary to have an accurate prognosis for the patient, so that treatment can be tailored to the individual disease of that patient.

The clinical and information tools currently available to clinicians for the classification and prognostic evaluation of cancer have serious limitations, especially when applied to an individual patient. It would be desirable to integrate the clinical and biological information for a given cancer in an individual patient's particular cancer.

Gene expression data is available using standard microarray data. Gene expression microarrays, such as available from Affymetrix™, provide a large volume of data and can be used to characterise a particular disease or condition in a patient by comparing diseased or abnormal tissue with healthy normal tissue. However, the data obtained can be difficult to process to obtain meaningful information about a particular condition or disease.

This problem is particularly acute in medical applications relating to patient treatment. In order to influence patent management in a clinical environment, clinical decision support systems must have a high level of confidence. Shipp et al have elegantly demonstrated the potential of machine learning techniques for prognostic strafication of patients, however their approach misclassified 30% of the patients in terms of predicting the outcome of their treatment. They achieved 70% correct prognosis of cured cases of B-cell lymphoma cancer, and wrongly predicted 12% of the cases as cured in contrast to the actual fatal outcome. This accuracy is not appropriate for a clinical application of the model. The models on the same data presented in Alizadeh et al are not clinically applicable either.

Another difficulty with prior art approaches using machine learning is that they often do not provide an easy means for the model should new data become available. Instead, complete retaining of the model is required. This is time-consuming and potentially expensive as it involves intensive computational resources. It is desirable that any system used be able to adapt to the addition of new data without complete retaining of the system.

It has been found by the inventors that in a general view, techniques utilising Evolving Connectionist Systems (ECOS) techniques have the following advantages when compared with the traditional statistical and neural network techniques: (i) they have a flexible structure that reflects the complexity of the data used for their training; (ii) they perform both clustering and classification/prediction; (iii) the models can be adapted on new data without the need to be retained on old data; (iv) they can be used to extract rules (profiles) of different sub-classes of samples. The rules (profiles) are fuzzy with some statistical coefficients attached.

It is therefore an object of the present invention to provide a method for determining a relationship between gene expression data and one or more conditions or prognostic outcome, or at least to provide the public with a useful choice.

SUMMARY OF THE INVENTION

In broad terms in one aspect of the invention comprises a neural network module comprising an input layer comprising one or more input nodes configured to receive gene expression data; a rule base layer comprising one or more rule nodes; an output layer comprising one or more output nodes configured to output one or more conditions; and an adaptive component configured to extract one or more roles from the rule base layer representing relationships between the gene expression data and the one or more conditions.

In another aspect, the present invention provides a generic method for determining a relations between gene expression data and one or more conditions including at least the steps of:

a) providing sets of gene expression data categorised into one or more predetermined classes of condition;

b) training a neural network module on said gene expression data and said one or more predetermined classes of condition, wherein the neural network module comprises an input layer comprising one or more input nodes configured to receive gene expression data; a rule base layer comprising one or more rule nodes; an output layer comprising one or more output nodes configured to output one or more classes of condition; and an adaptive component configured to extract one or more rules from the rule base layer representing relationships between the gene expression data and the one or more classes of condition; and c) extracting rules from the ride base layer, said rules representing relationships between the gene expression data and the one or more classes of condition.

In another aspect the present invention, provides a system for determining a relationship between gene expression data and one or more conditions comprising:

a) an input capable of receiving sets of gene expression data categorised into one or more predetermined classes of condition;

b) a neural network module tile on said gene expression data and said one or more predetermined classes of condition, wherein the neural network module cases an input layer comprising one or more input nodes configured to receive gene expression data; a rule base layer comprising one or more rule nodes; an output layer comprising one or more output nodes configured to output one or more classes of condition; and an adaptive component configured to extract one or more rules from the rule base layer representing relations between the gene expression data and the one a more classes of condition; and c) means for extracting rules from the rule base layer, said rules representing relationships between the gene expression data and the one or more classes of condition.

In another aspect, the present invention provides a generic method for diagnosing a condition in a patent comprising determining whether gene expression data extracted from a biological sample from said patient satisfies rules representing relationships between the gene expression data and one or more classes of condition, said rules determined by a method of the invention.

In another aspect, the present invention provides a generic system for diagnosing a condition in a patient comprising means for determining whether gene expression on data extracted from a biological sample from said patent satisfies rules representing relationships between the gene ession data and one or more classes of condition, said rules determined by a method of the invention.

In another aspect, the present invention pomades a method for selecting a set of distinguishing over-expressed or under-expressed genes linked to one or more conditions comprising:
a) providing one or more sets of gene expression data categorised into one or mom predetermined conditions;
b) training a neural network module on said gene expression data and one or more predetermined conditions, the neural network comprising an input layer comprising one or more input nodes configured to receive gene expression data; a rule base layer comprising one or more rule nodes; an output layer comprising one or more output nodes configured to output one or more conditions; and an adaptive component configured to extract one or more rules from the rule base layer representing relationships between the gene expression data and the one or more condition, said adaptive component arranged to aggregate selected two or more rule nodes in the rule base layer based on the input data;
c) permitting the adaptive component to aggregate selected two or more rule nodes in the rule-base layer;
d) extracting rules from the rule base layer, said rules representing relationships between the gene expression data and the one or more conditions;
e) identifying over-expressed or under-expressed genes from the extracted rules, which genes represent a set of distinguishing over-expressed or under-expressed genes linked to the one or more conditions.

In another aspect, the present invention provides a system for selecting a set of distinguishing over-expressed or under-expressed genes linked to one or more conditions comprising:
a) an input capable of receiving one or more sets of gene expression data categorised into one or more predetermined conditions;
b) a neural network module adapted to receive said gene expression data and one or more predetermined conditions, the neural network comprising an input layer comprising one or more input nodes configured to receive gene expression data; a rule base layer comprising one or more rule nodes; an output layer comprising one or more output nodes configured to output one or more conditions; and an adaptive component configured to extract one or more rules from the rule base layer representing relationships between the gene expression data and the one or more conditions, said adaptive component arranged to aggregate selected two or more rule nodes in the rule base layer based on the input data;

d) an extraction component for extracting rules from the rule base layer, said rules representing relationships between the gene expression data and the one or more conditions;
e) an identifier for identifying over-dressed or under-dressed genes from the extracted rules, which genes represent a set of distinguishing over-expressed or under-expressed genes linked to the one or more conditions.

Preferably, the rules extracted permit specific gene expressions to be linked to a particular condition.

In another aspect, the present invention provides a method for gene expression set reduction comprising:
a) providing one or more sets of gene expression data categorised by one or more conditions;
b) training a neural network module on said gene expression data and the one or more classes of condition, the neural network comprising an input layer comprising one or more input nodes configured to receive gene expression data; a rule layer comprising one or more rule nodes; an output layer comprising one or more output nodes configured to output one or more conditions; and an adaptive component configured to extract one or more rules from the rule base layer representing relationships between the gene expression data and the one or more conditions, said adaptive component arranged to aggregate selected two or more rule nodes in the rule base layer based on the int data;
c) permitting the adaptive component to aggregate selected two or more rule nodes in the rule-base layer;
d) extracting rules from the rule base layer, said rules representing relationships between the gene expression data and the one or more conditions;
e) identifying genes from the extracted rules, which genes represent a reduced gene expression set linked to the one or more conditions.

In another aspect, the present invention provides a system fir gene expression set reduction comprising:
a) input means for receiving one or more sets of gene expression data categorised by one or more conditions;
b) a neural network module trainable on said gee expression data and the one or more classes of condition, the neural network comprising an input layer comprising one or more input nodes configured to receive gene expression data; a rule base layer comprising one or more rule nodes; an output layer comprising one or more output nodes configured to output one or more conditions; and au adaptive component configured to extract one or more rules from the rule base layer representing relationships between the gene expression data and the one or more conditions, said adaptive component arranged to aggregate selected two or more rule nodes in the rule base layer based on the input data;
d) rule extraction means adapted to extract rules from the rule base layer, said rules representing relationships between the gene expression data and the one or more conditions;
e) an identifier adapted to identify genes from the extracted rules, which genes represent a reduced gene expression set liked to the one or more conditions.

In another aspect, the present invention provides a neural network module comprising an input layer comprising one or more input nodes configured to receive gene expression data; a rule base layer comprising one or more rule nodes; an output layer comprising one or more output nodes configured to output one or more conditions; and au adaptive component configured to extract one or more riles from the rule base layer representing relationships between the gene expression data and the one or more condition; said adaptive component arranged to aggregate selected two or more rule nodes in the rule base layer based on the gene expression data.

In another aspect, the present invention provides rules representing relationships between gene epression data and one or more conditions when extracted from a neural network according to a method of the invention.

In another aspect, the present invention provides a method of training a neural network to diagnose a condition, the method including at least the steps of:
a) providing gene expression data categorised by one or more conditions;
b) training a neural network module on the gene expression data and the one or more conditions, wherein the neural network module comprises an input layer comprising one or more input nodes configured to receive gene expression data; a rule base layer comprising one or more rule nodes; an output layer comprising one or more output nodes configured to output one or more conditions; and an adaptive component configured to extract one or more rules from the rule base layer representing relationships between the gene expression data and the one or more conditions;
c) testing the data using a leave one out method;
d) reducing input gene expression data to give best test accuracy;
e) modifying the neural network module to accept the reduced gene expression data as its input layer;
f) training the modified neural network module;
g) extracting rules from the adaptive component;
h) optionally repeating the method from the reduction step.

In another aspect, the present invention provides a system for training a neural network to diagnose a condition, the system comprising:
a) an input able to receive providing gene expression data categorised by one or more conditions;
b) a neural network module trainable on the gene on data and the one or more conditions, wherein the neural network module comprises an input layer comprising one or more input nodes configured to receive gene expression data; a rule base layer comprising one or more rule nodes; an output layer comprising one or more output nodes configured to output one or more conditions; and an adaptive component configured to extract one or more rules from the rule base layer representing relationships between the gene expression data and the one or more conditions;
d) an input gene expression data reducer operable to reduce gene expression data to give best test accuracy;
e) a neural network modifier to modify the neural network module to accept the reduced gene expression data as its input layer;
g) a rule extracting means for extracting rules from the adaptive component;

Preferably, the above extracted rules are represented in human readable form. In a preferred embodiment, the neural network module further comprises a pruning algorithm arranged to prune nodes in the rule base layer not demonstrating a sufficient link to the one or more conditions.

In broad terms in another aspect of the invention comprises a neural network module comprising an input layer comprising one or more input nodes configured to receive gene expression data; a rule base layer comprising one or more rule nodes; an output layer comprising one or more output nodes configured to output one or more prognostic outcomes; and an adaptive component configured to extract one or more rules from the rule base layer representing relationships between the gene expression data and the one or more prognostic outcomes.

In another aspect, the present invention provides a generic method for determining a relationship between gene expression data and prognostic outcome including at least the steps of:
a) providing sets of gene expression data classified by a predetermined prognostic outcome;
b) training a neural network module on said gene expression data and prognostic outcome, wherein the neural network module comprises a input layer comprising one or more input nodes configured to receive gene expression data; a mile base layer comprising one or more rule nodes; a output layer comprising one or more output nodes configured to output one or more prognostic outcomes; and an adaptive component configured to extract one or more rules from the role base layer representing relationships between the gene expression data and the one or more prognostic outcomes;
c) extracting rules from the rule base layer, said rules representing relationships between the gene expression data and one or more prognostic outcomes.

In another aspect, the present invention provides a generic system for condition prognosis in a patient comprising a correlating engine adapted to correlate gene expression data extracted from a biological sample from said patient with roles represent relationships between the gene expression data and prognostic outcomes, said rules determined by a method of the invention.

In another aspect, the present invention provides a generic system for determining a relationship between gene expression data and prognostic outcome comprising:
a) input for receiving sets of gene expression data classified by a predetermined prognostic outcome;
b) a neural network module trainable on said gene expression data and prognostic outcome, wherein the neural network module comprises an input layer comprising one or more input nodes configured to receive gene expression data; a rule base layer comprising one or more rule nodes; an output layer comprising one or more output nodes configured to output one or more prognostic outcomes; and an adaptive component configured to extract one or more rules from the rule base layer representing relationships between the gene expression data and the one or more prognostic outcomes;
c) a rule extractor adapted to extract rules from the rule base layer, said rules representing relationships between the gene expression data and one or more prognostic outcomes.

In another aspect, the present invention provides a generic method for condition prognosis in a patient comprising correlating gene expression data extracted from a biological sample from said patient with rules representing relationships between the gene expression data and prognostic outcomes, said rules determined by a method of the invention.

In another aspect, the present invention provides a generic system for condition prognosis in a patient comprising a correlating means adapted to correlate gene expression data extracted from a biological sample from said patient with roles representing relationships between the gene expression data and prognostic outcomes said rules determined by a method of the invention.

In another aspect, the present invention provides a method for selecting a set of distinguishing over-expressed or under-expressed genes linked to one or more prognostic outcomes comprising;

a) providing one or more sets of gene expression data categorised into one or more predetermined prognostic outcomes;
b) training a neural network module on said gene expression data and one or more predetermined prognostic outcomes, the neural network comprising an input layer comprising one or more input nodes configured to receive gene expression data; a rule base layer comprising one or more rule nodes; an output layer comprising one or more output nodes configured to output one or more prognostic outcomes; and an adaptive component configured to extract one or more rules from the rule base layer representing relationships between the gene expression data and the one or more prognostic outcomes, said adaptive component arranged to aggregate selected two or more rule nodes in the rule base layer based on the input data;
c) permitting the adaptive component to aggregate selected two or more rule nodes in the rule-base layer;
d) extracting rules from the rule base layer, said rules representing relationships between the gene expression data and the one or more prognostic outcomes;
e) identifying over-expressed or under-expressed genes from the extracted rules, which genes represent a set of distinguishing over-expressed or under-expressed genes linked to the one or more prognostic outcomes.

In another aspect, the present invention provides a system for selecting a set of distinguishing over-expressed or under-expressed genes linked to one or more prognostic outcomes comprising:
a) input for receiving one or more sets of gene expression data categorised into one or more predetermined prognostic outcomes;
b) a neural network module trainable on said gene expression data and one or more predetermined prognostic outcomes, the neural network comprising an input layer comprising one or more input nodes configured to receive gene expression data; a rule base layer comprising one or more rule nodes; an output layer comprising one or more output nodes configured to output one or more prognostic outcomes; and an adaptive component configured to extract one or more rules from the rule base layer representing relationships between the gene expression data and the one or more prognostic outcomes, said adaptive component arranged to aggregate selected two or more role nodes in the rule base layer based on the input data;
d) a rule extractor adapted to extract rules from the rule base layer; said rules representing relationships between the gene expression on data and the one or more prognostic outcomes;
e) an identifier able to identify over-expressed or under-expressed genes from the extracted roles, which genes represent a set of distinguishing over-expressed or under-expressed genes liked to the one or more prognostic outcomes.

In another aspect, the present invention provides a method for gone expression set reduction comprising:
a) providing one or more sets of gene expression data categorised by one or more prognostic outcomes;
b) training a neural network module on said gene expression data and the one or more classes of condition, the neural network comprising an input layer comprising one or more input nodes configured to receive gene expression data; a rule base layer comprising one or more rule nodes; an output layer comprising one or more output nodes configured to output one or more prognostic outcomes; and an adaptive component configured to extract one or more rules from the rule base layer representing relationships between the gene expression data and the one or more prognostic outcomes, said adaptive component arranged to aggregate selected two or more rule nodes in the rule base layer based on the input data;
c) permitting the adaptive component to aggregate selected two or more rule nodes in the rule-base layer;
d) extracting rules from the rule base layer, said rules representing relationships between the gene expression data and the one or more prognostic outcomes;
e) identifying genes from the extracted rules, which genes represent a reduced gene expression set linked to the one or more prognostic outcomes.

In another aspect, the present invention provides a system for gene expression set reduction comprising:
a) input to receive or more sets of gene expression data categorised by one or more prognostic outcomes;
b) a neural network module trainable on said gene expression data and the one or more classes of condition, the neural network comprising an input layer comprising one or more input nodes configured to receive gene expression data a rule base layer comprising one or more rule nodes; an output layer comprising one or more output nodes configured to output one or more prognostic outcomes; and an adaptive component configured to extract one or more rules from the rule base layer representing relationships between the gene expression data and the one or mom prognostic outcomes, said adaptive component arranged to aggregate selected two or more role nodes in the rule base layer based on the input data;
d) a rule extractor adapted to extract rules from the rule base layer, said rules representing relationships between the gene expression data and the one or more prognostic outcomes;
e) an identifying means adapted to identify genes from the extracted rules, which genes represent a reduced gene expression set linked to the one or more prognostic outcomes.

In another aspect, the preset invention provides a neural network module comprising an input layer comprising one or more input nodes configured to receive gene expression data; a rule base comprising one or more rule nodes; an output layer comprising one or more output nodes configured to output one or more prognostic outcomes; and an adaptive component configured to extract one or more rules from the rule base layer representing relationships between the gene epression data and the one or more prognostic outcomes, said adaptive component arranged to aggregate selected two or more rule nodes in the rule base layer based on the gene expression data.

In another aspect, the present invention provides rules representing relationships between gene expression data and one or more prognostic outcomes when extracted from a neural network according to a method of the invention.

In another aspect, the present invention provides a method of training a neural network to provide a prognostic outcome, the method including at least the steps of:
a) providing gene expression data categorised by one or more prognostic outcomes;
b) training a neural network module on the gene expression data and the one or more prognostic outcomes, wherein the neural network module comprises au input layer comprising one or more input nodes configured to receive gene expression data; a rule base layer comprising one or more rule nodes; an output layer comprising one or more output nodes configured to output one or more prognostic outcomes; and an adaptive component configured to extract one or more rules from the rule base layer representing relationships between the gene expression data and the one or more prognostic outcomes;
c) testing the data using a leave one out method;
d) reducing input gene expression data to give best test accuracy,
e) modifying the neural network module to accept the reduced gene expression data as its input layer;
f) training tie modified neural network module;
g) extracting rules from the adaptive component;
h) optionally repeating the method from the reduction step.

In another aspect, the present invention provides a system of training a neural network to provide a prognostic outcome, the system comprising:
a) input for receiving gene expression data categorised by one or more prognostic outcomes;
b) a neural network module trainable on the gene expression data and the one or more prognostic outcomes, wherein the neural network module comprises au input layer comprising one or more input nodes configured to receive gene expression data; a rule base layer comprising one or more rule nodes; an output layer comprising one or more output nodes configured to output one or more prognostic outcomes; and an adaptive component configured to extract one or more rules from the rule base layer representing relationships between the gene expression data and the one or more prognostic outcomes;
d) a reducer for reducing input gene expression data to give best test accuracy;
e) a modifier adapted to modify the neural network module to accept the reduced gene expression as its input layer;
g) a rule extractor for extracting rules from the adaptive component;

Preferably, the above extracted are represented in human readable form. In a preferred embodiment, the neural network module further comprises a pruning algorithm arranged to prune nodes in the rule base layer not demonstrating a sufficient link to the one or more prognostic outcomes.

In one embodiment, the rules extracted permit profiling of breast adenocarcinoma, prostate adenocarcinoma, lung adenocarcinoma, colorectal adenocarcinoma, lymphoma, bladder transitional cell carcinoma, melanoma uterine adenocarcinoma, leukemia, renal cell carcinoma, pancreatic adenocarcinoma, ovarian adenocarcinoma, pleural mesothelioma, and central nervous system cancer.

In another preferred embodiment, the methods and systems of the invention are applied to profiling breast adenocarcinoma, prostate adenocarcinoma, lung adenocarcinoma, colorectal adenocarcinoma, lymphoma, bladder transitional cell carcinoma, melanoma, uterine adenocarcinoma, leukemia, renal cell carcinoma, pancreatic adenocarcinoma, ovarian adenocarcinoma, pleural mesothelioma, and central nervous system cancer.

In another embodiment, the rules extracted permit profiling of DLBCL (Diffuse Large B-Cell Lymphoma).

In another preferred embodiment, the methods and systems of the invention are applied to profiling DLBCL (Diffuse Large B-Cell Lymphoma).

In another aspect, the present invention provides a gene profile for any one of 14 types of cancer: Breast-, Prostate-, Bladder-, Leukemia-, Lymphoma-, Central nervous system-, Lung-, Colorectal-Melanoma, Uterine, Renal cell-, Pancreatic-, Ovarian-, and Pleural Cancers as set forth in the Figures as read with the description herein.

In another aspect, the present invention provides a gene profile for any one of 14 types of cancer: Breast-, Prostate-, Bladder-, Leukemia-, Lymphoma-, Central nervous system-, Lung-, Colorectal-Melanoma, Uterine-, Renal cell-, Pancreatic-, Ovarian-, and Pleural Cancers comprising at least one of the genes as set forth in the Figures as read with the description herein.

Preferably the profile comprises at least two genes in the profile, more preferably at least three genes in the profile, most preferably at least four genes in the profile.

In another aspect, the present invention relates to a diagnostic kit for diagnosing a cancer selected from the group comprising Breast-, Prostate-, Bladder-, Leukemia-, Lymphoma-, Central nervous system-, Lung-, Colorectal-Melanoma, Uteri, Renal cell-, Pancreatic-, Ovarian-, and Pleural Cancers comprising at least one nucleic acid sequence that selectively ligates to at least one of the gene expression products of te genes as set forth in the Figures for each of the respective cancers in question as read with the description herein.

Preferably, the kit also comprises an amount of the at least one nucleic acid sequence able to quantitatively determine the amount of the gene expression products present in a sample.

In another aspect, the present invention relates to a diagnostic kit for diagnosing a cancer selected from the group comprising Breast-, Prostate-, Bladder-, Leukemia-, Lymphoma-, Central nervous system-, Lung-, Colorectal-Melanoma, Uterine-, Renal cell-, Pancreatic-, Ovarian-, and Pleural Cancers comprising a ligand capable of selectively binding to a peptide expressed from a nucleic acid sequence expressed from at least one of the genes as set forth in the Figures for each of the respective cancers in question as read with the description herein.

Preferably, the ligand is an antibody or an immunomolecule, such as a fab fragment. In a preferred embodiment, the ligand is specifically capable of binding to the peptide in question. Preferably, the kit also comprises an amount of ligand able to quantitatively determine the amount of peptide present in a sample.

In another aspect, the present invention relates to a method for diagnosing whether a patient is suffering from a cancer selected from the group comprising Breast-, Prostate-, Bladder-, Leukemia-, Lymphoma-, Central nervous system-, Lunge-, Colorectal-Melanoma, Uterine, Renal call-, Pancreatic-, Ovarian-, and Pleural Cancers comprising the steps of:
a) isolating a sample from the patient,
b) determining whether the sample contains expression levels consistent with a disease profile of at least one gene in the as set forth in the Figures for each of the respective cancers in question as read with the description herein.

Preferably the sample is a tissue, more preferably a tissue suspected of being cancerous.

BRIEF DESCRIPTION OF THE FIGURE

Preferred forms of the method and system for disease profiling will now be described with reference to the accompanying figures in which.

DETAILED DESCRIPTION OF PREFERRED FORMS

Figure 1:
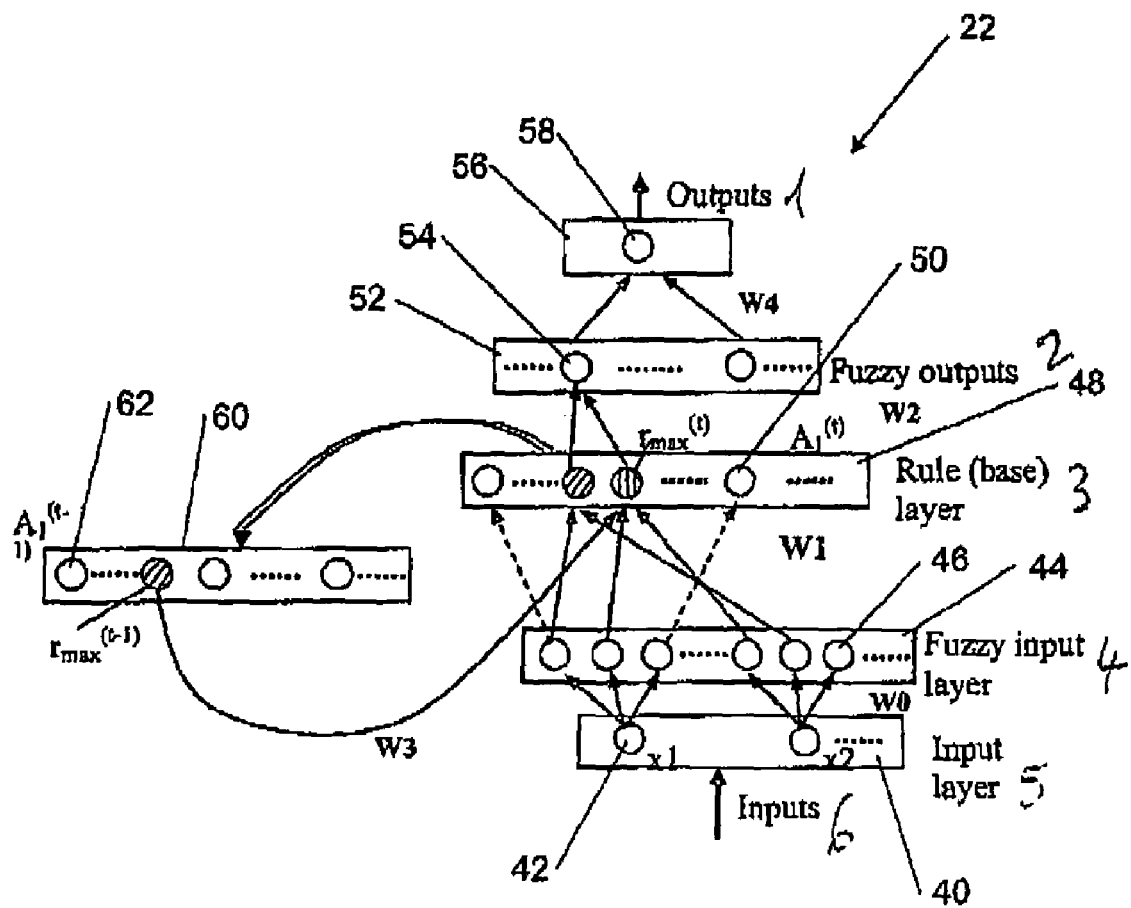
FIG. 1 is a schematic block diagram view of a neural network module useful in the invention.

In the present specification, "biological sample" means a sample including at least a nucleic acid molecule or a polypeptide molecule. Such samples may conveniently be sourced from cells. The cells may, in turn, be extracted from tissues. Preprocessing of samples may take place by, for example; extracting DNA, RNA and/or polypeptides from a raw sample using well-known techniques in the art. Other pre-processing may be conducted by, for example, predigesting the sample using DNAses, RNAses and proteinases.

A "condition" is a disease, disorder or trait selected from the group comprising cancer, a congenital disease and a hereditary disease. A "condition" also includes non-disease causing traits. A "predisposition to a condition" may also include a genetic predisposition to a condition. A non-limiting example of a non-disease causing trait is alopecia.

Evolving connectionist systems ("ECOS") are multi-modular, connectionist architectures that facilitate modelling of evolving processes and knowledge discovery (PCT, WO 01/78003)

An ECOS may consist of many evolving connectionist modules. An ECOS is a neural network system that operates continuously in time and adapts its structure and functionality through a continuous interaction with the environment and with other systems according to: (i) a set of parameters P that are subject to change during the system operation; (ii) an incoming continuous flow of information with unknown distribution; (iii) a goal (rationale) criteria (also subject to modification) that is applied to optimise the performance of the system over time.

The evolving connectionist systems have the following specific characteristics:

(1) They evolve in an open space, not necessarily of fixed dimensions.
(2) They learn in on-line, pattern mode, incremental learning, fast learning—possibly by one pass of data propagation.
(3) They learn in a life-long learning mode.
(4) They learn as both individual systems, and evolutionary population systems.
(5) They have evolving structures and use constructive learning.
(6) They learn locally and locally partition the problem space, thus allowing for a fast adaptation and tracing the evolving processes over time.

(7) They learn different kinds of knowledge, mostly combined memory based, statistical and symbolic knowledge.

There are two distinct phases of ECOS operation. During the first, the learning phase, data vectors are fed into the system one by one with their known output values. In the second phase (recall) a new vector is presented to the system and it calculates the output values for it.

There are different models of ECOS protected by (PCT, WO 01/78003 A1). One of them, evolving fuzzy networks (EFuNN) is presented in FIG. 1 and its algorithm given in FIG. 2. EFuNN can be used for both classification tasks and prediction tasks.

While "neural network module" may refer to any neural network satisfying the requirements of th aspects of the invention above, the use of an ECOS neural network is preferred. Particularly preferred is the neural network exemplified in PCT publication WO 01/78003 (incorporated herein by reference). The algorithm describing the neural network from WO 01178003 is set out below:

The EFuNN learning algorithm (from PTO WO 01/78003 A1).

Set initial values for the system parameters: number of membership functions; initial sensitivity thresholds (default Sj=0.9); error threshold E; aggregatice parameter Nagg— number of consecutive examples after each aggregation is performed; pruning parameters OLD an Pr; a value for m (in m-of-n mode); maximum radius limit Rmax; thresholds $T_1$ and $T_2$ for rule extraction.

Set the first rule node $r_0$ to memorize the first example (x,y):

$$W1(r_0)=x_f \text{ and } W2(r_0)=y_f; \tag{10}$$

Loop over presentations of new input-output pairs (x,y) is the same as the current vector in the input data space and its radius is set to the min-radius parameter, ad then go to step 1; otherwise;

3) if there is a rule node with a distance to the current input vector less then or equal to its radius and its class is the same as the class of the new vector, noting will be changed and go to step 1; otherwise.

4) if there is rule node with a distance to the input vector less then or equal to its radius and its class is different from those of the input vector, its influence field should be reduced, the radius of the new field is set to the larger value from the distance minus the min-radius, and the mini-radius.

5) if there is a rule node with a distance to the input vector less then or equal to the max-radius, and its class is the same to the vector's, enlarge the influence field by taking the distance as the new radius if only such enlarged field does not cover any other rule node which has the different class; otherwise, create a new nile node the same way as in step 2, and go to step 1.

The recall (classification phase of new input vectors) in ECF is performed in the following way:

1) if the new input vector lies within the field of one or more rule nodes associated with one class, the vector belongs to this class;

2) if the input vector lies within the fields of two or more rule nodes associated with different classes, the vector will belong to the class corresponding the closest ride node.

3) if the input vector does not lie within any field, then there are two cases: (1) one-of-n mode: the vector will belong to the class corresponding to closest rule node; (2) m-of-n mode: take m highest activated by the new vector rule nodes, and calculate the average distances from the vector

```
{
   Evaluate the local normalised fuzzy distance D between $x_f$ and the existing rule node connections W1
   (formulae (1))
   Calculate the activation A1 of the rule node layer. Find the closest rule node $r_k$ (or the closest m rule
   nodes in case of m-of-n mode) to the fuzzy input vector $x_f$ for which $A1(r_k) >= S_k$ (sensitivity
   threshold for the node $r_k$),
   if there is no such a nods, create a new rule node for $(x_f,y_f)$
      else
         Find the activation of the fuzzy output layer A2-W2.A1(1-D(W1,$x_f$))) and the normalised
         output error Err= ‖ y– y'‖ / Nout.
         ifErr > E
            create a new rule node to accommuodate the current example $(x_f,y_f)$
         else
            Update W1 $(r_k)$ and W2$(r_k)$ according to (2) and (3) (in case of m-of-n system
            update all the m rule nodes with the highest A1 activation).
   Apply aggregation procedure of rule nodes after each group of $N_{agg}$ examples are presented
   Update the Values for the rule node $r_k$ parameters $S_k$, $R_k$ Age$(r_k)$, TA $(r_k)$.
   Prune rule nodes if necessary, as defined by pruning parameters.
      Extract rules from the rule nodes (
   }
```

Another example of a particularly preferred neural network module for some aspects of the invention is an ECF.

Evolving classification function ("ECF"), can be used to classify data. The learning sequence of each iteration of ECF is described in the following steps:

1) if all vectors have been inputted, finish the current iteration; otherwise, input a vector from the data set and calculate the distances between the vector and all rule nodes already created;

2) if all distances are greater than a max-radius parameter, a new rule node is created, the position of the new rile node to the nodes with the same class; the vector will belong to the class corresponding the smallest average distance.

The above-described ECF for classification has several parameters that need to be optimized according to the data set used. These are:

1) maximum radius
2) minimum radius
3) number of membership functions (mf)
4) m-of-n value
5) number of iterations for the data presentation during learning phase.

These parameters can be optimized with the use of evolutionary computation methods, or other statistical methods.

On one embodiment, the invention employs an adaptive method for gene reduction, model creation and profiling. The methodology employs ECOS. The methodology is comprised of the following main phases:
(1) Train continuously an evolving connectionist system (ECOS) on incoming data thus creating a "mother" system that accommodates all available data;
(2) Extract features (genes) relevant to the output classes from the "mother" system;
(3) Create a model based on the selected features and the output classes.
(4) Extract profiles (rules)

Feature selection in the adaptive component of an ECOS is preferably performed through the extraction of rules from the ECOS created by supervised training on all available data. The ECOS training parameters are optimized so that the classification error is minimised and the ECOS models most closely the features present in the data Eat node in the hidden layer of the ECOS represents the center of a cluster of similar samples and can be expressed semantically as a rule. Each rule relates to the pattern of input feature levels for one or more samples belonging to a particular class from the data set. An example of what a rule might look like when attracted from the EFuNN is shown below:

IF VAR1 is LOW (0.80) and
VAR3 is HIGH (0.76) and
VAR12 is HIGH (0.91) and
VAR25 is LOW (0.80) and
VAR31 is LOW (0.87) and then CLASS_Z is VERY LIKELY (with a membership degree of 0.92), Accommodated Training Examples in this rule are 10 out of 50, Radius of the cluster for this rule is 0.15.

The rules are then analysed in order to identify a set of variables that are significant in distinguishing between classes. This is achieved by ranking each variable according to its importance in the rules for each class wing a standard signal-to-noise ration method as used in (Ramaswami et al; Dudoit et al)).

Using this method each input variable is assigned a value between −1 and 0 for ah class. For each class, variables are then selected if their rank value is above a set threshold value. This value is altered in order to select an optimal set of input features. Any variables that are selected through more than one class are only included once in the feature (gene) set thus representing a reduced gene set.

Once the feature selection (gene selection) phase is complete, the original data set is minimised by removing any features not present in the feature set. This new data is then used to train anew ECOS. With the reduced feature space the time for training will be significantly reduced. The perforce of the ECOS should be evaluated and training parameters modified so that the classification error is minimized and the generalization ability of the model is maximized.

The invention provides an information system which can integrate and interpret complex gene expression data and which can be adapted to the diagnostic evaluation, prognostic assessment neuro-computing management of patients. The method is based on knowledge-based neuro-computing which uses the learning ability of a supervised learning neural network to learn patters from input-output data pairs and then ert rules from the structure.

Once a profile for a particular disease is extracted, the genes used in the profile may be used as input variables in a new ECOS model trained and tested in a leave-one-out method (see Dudoit et all, Shipp et al) on all available data to evaluate accuracy.

We have formed that ECOS describe in WO 01/78003 are particularly suited for complex disease profiling based on a variety of information sources, including gene expression data.

In one form, the invention can be applied to develop new methods fir disease classification, outcome of treatment prognosis and drug response prognosis. Disease profiles can also be extracted through the method described above. Profiles extracted from the network may define tumor subgroups which can be interpreted by determination of a function of the genes that constitute the rules. These genes will correspond to over-expressed and under-expressed genes that contribute to tumorigenesis, or are a consequence of tumorigenesis. Different rules would be extracted to include different genes contributing to the same functional unit for example signaling pathway or cell adhesion complex, or different genes from redundant functional units, for example parallel signaling pathways that lead to the same phenotypic outcome.

These general functional units would include the evasion of apoptosis, growth signaling, angiogenesis, tissue invasion/metastasis and replicative potential.

Analysis of the identity and function of genes in these rules would therefore be predicted to identify the functional units that are critically perturbed in the tumors and the consequences of these perturbed functions.

The genes which form the rules most correspond to transcripts that are expressed in the tumor tissue-specific patterns. Those may be tissue-specific genes that are over-expressed in the tumor tissue but do not contribute to the disease progression, for example insulin in an insulinoma or certain differentiation markers, or over-expressed and under-expressed genes that play a role in tumorigenesis but in a tumor specific pattern these genes would be a subset of those identified above, namely genes will exclude genes which contribute to functional units common to multiple cancers.

In one form of the invention the input data comprises raw gene expression data. The input data is first filtered as described above using a suitable filtering, normalisation or log transformation process. A standard statistical test, for example a T test or other correlation could be applied to this pre-processed data and the genes obtained from this data that best distinguish the output classes. $N_1$ genes could be selected from an initial set of N where $N_1$ is less than N that are above a chosen threshold. Each gene could also be ranked.

The input data could comprise the $N_1$ gene inputs as the individual expression values of the N selected genes, such as those mentioned above, The outputs could be, for example, 14 different types of cancer. The model or models would be trained on this input and output data as described above with reference to FIG. 2. The model is then tested on a reduced input data set of features $N_1$.

After training, each feature, for example a gene belonging to a membership function defining a high value $G_h$ is ranked for each class CI based on calculated values $G_h$, I as follows:

$$G_h, I = (G_h, mi - G_h, ma)(G_h, mr - G_h, ma)$$

$G_h$, mi is the mean value for gene G is high for all rule nodes from the trained network that support class that CI, $G_h$, ma is the mean value for gene G is high for all rule nodes from the trained network across output classes, and $G_h$, mr is the measure value for gene G is high for all rule nodes from the trained network that support other classes than class CI.

A threshold $G_{thr}$ is applied and a new set of features, in this case genes, is selected for each class includes all genes that have at least one membership degree above th threshold. The features of all classes are combined together to form a new e set of $N_2$ genes.

Rules are then extracted from the model, each rule representing a profile of a group or cluster from the N-dimensional gene expression space.

In some cases there will be new input data available and th structure of ECOS provides means for the addition of new data, therefore updating the model with new input data with the possibility of gaining improved accuracy.

Early Diagnostic Applications

Identification of specific antigens in body fluids including, for example, blood, urine, peritoneal washes and stool extracts can provide a valuable approach for the early diagnosis of disease and other conditions, leading to early treatment and improved prognosis. Specific antigens also can provide a means for monitoring disease or condition progression, enabling the efficacy of surgical, radiotherapeutic and chemotherapeutic treatments to be tracked. However, or a number of diseases and conditions, the available markers suffer from insufficient sensitivity and specificity.

In the case of a murder of diseases and conditions, proteins can be present in body fluids at evaluated levels compared to individuals without malignant disease, and can be sufficiently stable to enable immunodetection. Body fluids include blood, urine, sputum, semen, gastric fluids and stool. Where such body fluids are not useful, biopsies of suspect tissues may be used. Overexpression or underexpression can also be detected by either nucleic add detection or protein detection techniques in fluids if they contain cells, or cell lysates that arm released from suspect tissues.

Proteins of interest can also be detected in body fluids. For example, immuno-detection techniques using monoclonal or polyclonal antibodies raised against either whole proteins peptides of interest. Peptides of interest can be either synthetic or expressed in in vitro or in vivo systems. Immunodetection techniques can include, but not be limited to, ELISA/EIA radioimmunoassay, nephelometry, immunoturbidometric assays, chemiluminescence, immunofluorescence (by microscopy or flow cytometry), immunohistochemistry and Western blotting. It can be readily appreciated that other methods for detecting proteins can be used.

Kits

Based on the discoveries of this invention, several types of test kits can be produced. First, kits can be that have a detection device pre-loaded with a detection molecule (or "capture reagent"). In embodiments for detection of mRNA, such devices can comprise a substrate (e.g., glass, silicon, quartz, metal etc) on which oligonucleotides as capture reagents that hybridize with the mRNA to be detected. In some embodiments, direct detection of mRNA can be accomplished by hybridizing mRNA (labeled with cy3, cy5, radiolabel or other label) to the oligonucleotides on the substrate. In other embodiments, detection of mRNA can be accomplished by first making complementary DNA (cDNA) to the desired mRNA. Then, labeled cDNA can be hybridized to the oligonucleotides on the substrate and detected.

Regardless of the detection method employed, comparison of test expression with a standard measure of expression is desirable. For example, RNA expression can be standardized to total cellular DNA, to expression of constitutively expressed RNAs (for example, ribosomal RNA) or to other relatively constant markers.

Antibodies can also be used in kits as capture reagents. In some embodiments, a substrate (e.g., a multilevel plate) can have a specific capture reagent attached thereto. In some embodiments, a kit can have a blocking reagent included. Blocking reagents can be used to reduce non-specific binding. For example non-specific oligonucleotide binding can reduced using access DNA from any convenient source that does not contain oligonucleotides for detection, such as salmon sperm DNA. Non-specific antibody binding can be reduced using excess of a blocking protein such as serum albumin. It can be appreciated that numerous methods for detecting oligonucleotides and proteins are known in the art, and any strategy that can specifically detect associated molecules can be used and be considered within the scope of this invention.

In embodiments relying upon antibody detection, proteins or peptides of interest can be expressed on a per cell basis, or on the basis of total cellular, tissue, or fluid protein, fluid volume, tissue mass (weight). Additionally, XXX in serum can be expressed on the basis of a relatively high-abundance serum protein such as albumin.

In addition to a substrate, a test kit cam comprise capture reagents (such as probes), washing solutions (e.g., SSC, other salts, buffers, detergents and the like), as well as detection moieties (e.g., cy3, cy5, radiolabels, and the like). Kits can also include instructions for use and a package.

Methods for Making Antibodies to Proteins in Profile

To make antibodies the protein; any method known in the art can be used. For example, polyclonal antisera can be made by injecting isolated proteins, peptides or mixtures of proteins and peptides into a suitable animal, such as a rabbit. In some embodiments, an adjuvant can be used to augment the immune response. After suitable booster injections, serum can be collected and either used as serum, or, in alternative embodiments, IgG fractions can be produced from the serum.

In alternative embodiments, monoclonal antibodies can be made against the proteins or peptides using standard methods known in the art. Briefly, an isolated protein or peptide preparation is injected in to a suitable animal (e.g., a mouse), and an immune response is elicited. The spleen of the animal is removed, and splenocytes can be fused with myeloma cells to produce hybridomas. Hybridomas producing antibodies directed towards the target proteins or peptides cam be selected and cell cultures expanded to produce desired amounts of monoclonal antibodies. Antibodies can be further selected that have desired affinity and cell lines can be selected that have desirable growth characteristics and antibody production.

Peptides can be made from intact protein isolated from a tissue of interest (e.g., gastric tumor tissue) or can be chemically synthesized. In other embodiments, protein can be made using recombinant methods from cDNA specific for full-length target proteins or oligonucleotides encoding (in frame) a portion of the target proteins.

The antibody kit would consist of antibodies raised against the minimum number of proteins that characterize the profile. It could also include all the reagents for carrying out the assay.

RNA Based Kits

Kits can be made that have a detection device pre-loaded with a detection molecule (or "capture reagent"). In embodiments for detection of mRNA from genes within a genetic profile, such devices can comprise a substrate (e.g., glass, silicon, quart, metal, etc) on which oligonucleotides as capture reagents that hybridize with the mRNAs to be detected. In some embodiments, direct quantitative detection of mRNA call be accomplished by hybridizing mRNAs (labeled with cy3, cy5, radiolabeled or other label) to the oligonucleotides on the substrate. In other embodiments, detection of mRNAs can be accomplished by first making complementary DNA (cDNA) to the desired mRNAs. Then, labeled cDNAs can be hybridized to the oligonucleotides on the substrate and detected. cDNAs can also be detected using the Applied Biosystems Taqman™ procedure in which specific fluorescently-labelled oligonucleotide probes are hybridized to the target cDNA as it is amplified in a real-time PCR assay. Other quantitative detection methods including, but not limited to, molecular beacons and SyBr green labeling of PCR product, can also be used.

In one technique useful herein, relevant RNA can be detected by RT-PCP using oligonucleotide primers specific for conserved sequences within the gene or genes identified by methods of the present invention. Total RNA can be extracted from body fluid by standard techniques, converted to cDNA using reverse transcripts and them amplified using PCR. Desirable PCR primers flank intronic DNA to prevent the PCR amplification of genomic DNA. Results would be detected any conventional method, for example, either by gel electrophoresis or by quantitative real-time PCR techniques. Real-time PCR can be carried out using either fluorescently-labelled Taqman™ probes or direct binding of fluorescent dyes such as Sybr Green to the PCR product. However, it can be appreciated that other methods detecting nucleic acids of interest can be used.

In addition to a substrate, a test kit can comprise capture reagents (such as probes), washing solutions (e.g., SSC, other salts, buffers, detergents and the like), as well as detection moieties (e.g., cy3, cy5, radiolabels, and the like). Kits can also include instructions for use and a package.

Drug Target Validation

Once a gene set is identified by a method of the invention, the individual genes can be developed as drug targets following validation as described below. The drug target is typically a protein that is over-expressed within a diseased or malfunctioning cell. Drug candidates would typically then be manufactured against the drug targets. Monoclonal antibodies produced against the protein arid synthetic chemicals that bind the protein. The invention therefore extends to methods of identifying drug targets and to drug candidates.

One method of determining the presence of a drug target is to stably transfect a gene identified as implicated in a condition or disease by a method of the invention into cancer lines with inducible promoter. The protein expressed by the gene is then expressed and the effect of over expression on the cell line's viability is determined. The expression of the gene in cell lines is knocked out using either small interfering RNAs (siRNAs) or antibodies raised against the protein. The effect on cell viability is determined. If the gene in question has a desired effect on the cell either by killing the cell or by causing the cell to revert to a normal form then it is a drug target.

Disease Management Markers

The methods of the present invention enable the creation of disease management markers. Such markers permit a practitioner to determine whether a disease is present, and if it is how, it is responding to treatment. Profiles identified by a method of the invention that correspond to a specific disease characteristic would be developed as disease management markers as follows:

Detection kits for Disease management markers would typically consist of a panel of antibodies raised against the gene profile identified by EFuNN or a kit capable of testing expression at the RNA level. The present invention extends to such kits.

An antibody kit can be developed using the genes identified in the methods of the present invention that are over or under-expressed in a patient with a specific disease or condition. Antibodies or other immunomolecules against the proteins encoded by the identified genes are manufactured by standard techniques in the art. Biopsy samples of diseased or abnormal would be taken from a patient and then analysed using the antibodies or immunomolecules by immunodetection techniques including but not be limited to, ELISA/EIA, radioimmunoassay, nephelometry, immunoturbidometric assays, chemiluminescence, immunofluorescence (by microscopy or flow cytometry), immunohistochemistry and Western blotting for levels of the proteins that are over-or under-expressed in the diseased tissue. The presence of abnormal levels of the proteins in question are indicative of the presence of the specific disease or condition.

Using similar techniques, a patient with the specific disease or conditions can be monitored to determine whether treatment is having the desired effect.

It an alternative embodiment, a RNA based assay may be employed. Total RNA or mRNA would be exacted from the biopsy sample using standard techniques, then applied in a standard nucleic acid kit by ligating the RNA to one or more antisense markers indicative of the presence of a gene identified by a method of the present invention as over- or under-expressed in a specific disease or condition and determining the level of bound RNA. The level of bound RNA in a sample would be indicative of the absence or presence of the specific disease or condition. Using this technique, a patient with the specific disease or condition can be monitored to determine whether treatment is having the desired effect.

Methods for Making Antibodies to Proteins in Profile

To make antibodies against the proteins, any method known in the art can be used. For example, polyclonal antisera can be made by injecting isolated proteins, peptides or mixtures of proteins and peptides into a suitable animal, such as a rabbit. In some embodiments, an adjuvant can be used to augment the immune response. After suitable booster injections, serum can be collected and either used as se or, in alternative embodiments, IgG fractions can be produced torn the serum.

In alternative embodiments, monoclonal antibodies can be made against the proteins or peptides standard methods known in the art. Briefly, an isolated protein or peptide preparation is injected in to a suitable animal (e.g., a mouse), and an immune response is elicited. The spleen of the animal is removed, and splenocytes can be fused with myeloma cells to produce hybridomas. Hybridomas producing antibodies directed towards the target proteins or peptides can be selected and cell cultures expanded to produce desired amount of monoclonal antibodies. Antibodies can be further selected that have desire affinity and cell lines can be selected that have desirable growth characteristics and antibody production.

Peptides can be made from intact protein isolated from a tissue of interest (e.g. gastric tumor tissue) or can be chemically synthesized. In other embodiments, protein can be made using recombinant methods from cDNA specific for full-length target proteins or oligonucleotides encoding (in frame) a portion of the target proteins.

The antibody kit would consist of antibodies raised against the minimum number of protein that characterize the profile. It could also include all the reagents for carrying out the assay.

RNA Based Kits

Kits can be made that have a detection device pre-loaded with a detection molecule (or "capture reagent"). In embodiments for detection of mRNA from genes within a genetic profile, such devices can comprise a substrate (e.g., glass, silicon, quartz, metal, etc) on which oligonucleotides as capture reagents that hybridize with the mRNAs to be detected. In some embodiments, direct quantitative detection of mRNA can be accomplished by hybridizing mRNAs (labeled with cy3, Cy5, radiolabel or other label) to the oligonucleotides on the substrate. In other embodiments, detection of mRNAs can be accomplished by first making complementary DNA (cDNA) to the desired mRNAs. Then, labeled cDNAs can be hybridized to the oligonucleotides on the substrate and detected.

cDNAs can also be detected using the Applied Biosystems Taqman™ procedure in which specific fluorescently-labelled oligonucleotide probes are hybridized to the target cDNA as it is amplified in a real-time PCR assay. Other quantitative detection methods including, but not limited to, molecular beacons and SyBr green label of PCR product, can also be used.

In addition to a substrate, a test kit can comprise capture reagents (such as probes), washing solutions (e.g., SSC, other salts, buffers, detergents and the like), as well as detection moieties (e.g., cy3, cy5, radiolabels, and the like). Kits can also include instructions for use and a package.

The invention will be described below with reference to non-limiting examples:

EXAMPLE 1

FIG. 1 shows a neural network module 22. The preferred structure is a fuzzy neural network which is a connectionist structure which implements fuzzy rules. The neural network module 22 includes input layer 40 having one or more input nodes 42 arranged to receive input data. This input data will depend on the particular application to which the neural network module or modules are directed.

The neural network module also includes output layer 56 having one or more output nodes 58. The output nodes represent the real values of the output variables.

The input nodes and output nodes are configured depending on the type of information to be retrieved from the system. In one application involving gene expression profiling and classification of disease, the input data is a set of relevant variables, such as gene expression data, and the output variables are categories of diseases or prognostic outcomes over a time scale.

In another configuration for disease prognostic profile development and disease prognosis over a time scale, the input data comprises individual expression values of selected genes and the output data includes different types of disease, such as different types of cancer.

In a further configuration in relation to drug response prognosis and profile development, the inputs are configured as gene on data for a particular patient group given a particular treatment regime and the output data is prognosis.

The neural network module 22 may further comprise a fuzzy input layer 44 having one or more fuzzy input nodes 46. The fuzzy input nodes 46 transform data from the input nodes 42 for the further use of the system. Each of the fuzzy input nodes 46 could have a different membership fraction attached to it for example a triangular membership function, Gaussion function or any other known function suitable for the purpose. The main purpose of the fuzzy input nodes 46 is to transform the input values from the input nodes 42 into membership degrees to which the values belong to the membership function.

The neural network module 22 may further comprise a fuzzy output layer 42 having one or more fuzzy output nodes 54. Each fuzzy node 54 represents a fuzzy quantisation of the output variables, similar to the fuzzy input nodes 46 of the fizzy input layer 54. Preferably, a weighted sum input function and saturated linear activation function are used for the nodes to calculate the membership degrees to which the output vector associated with the presented input vector belongs to each of the output membership functions.

The neural network module 22 may also include a short term memory layer 60 having one or more memory nodes 62. The purpose of the short term memory layer 60 is to memorise structurally temporal relationships of the input data. The short term memory layer is preferably arranged to receive information form and send information to the rule base layer 48.

As more particularly described in WO 01/78003, each rule node 50 represents an association between a hyper sphere from the fuzzy input space and a hyper sphere from the fuzzy output space. Each rule node $r_j$ has a sensitivity threshold parameter $S_j$ which defines the minimum activation threshold of the rule node $r_j$ to a new input vector x from a now example or input (x, y) in order for the sample to be considered for association with this rule node. A new input vector x activates a rule node if x satisfies the minimum activation threshold and is subsequently considered for association with the rule node. The radius of the input hypersphere is defied as $R_j=1-S_j$, $S_j$ being the sensitivity threshold parameter.

Fuzzy logic rules and other types of knowledge are able to be extracted from the trained neural network or combination of neural networks in an easily accessible form. One example of a fuzzy rule extracted from a train network is:
R1: IF [gene 1 is high to a degree of 0.9] and [gene 3 is High to a degree of 0.9] and [gene 8 is Low to a degree of 0.8] {radius of the receptive field=0.109}THEN Disease A {accommodated examples=15 out of 24}

These types of rules represent relationships between the input data and the output data. They provide a profile from which knowledge can be gained about the classification or the prognostic process of a disease. The rules point to profiles of genes and clinical information which is strongly associated with a specific disease, for example different types of cancer, and can be used for the development of new tests and treatments.

EXAMPLE 2

Figure 2:
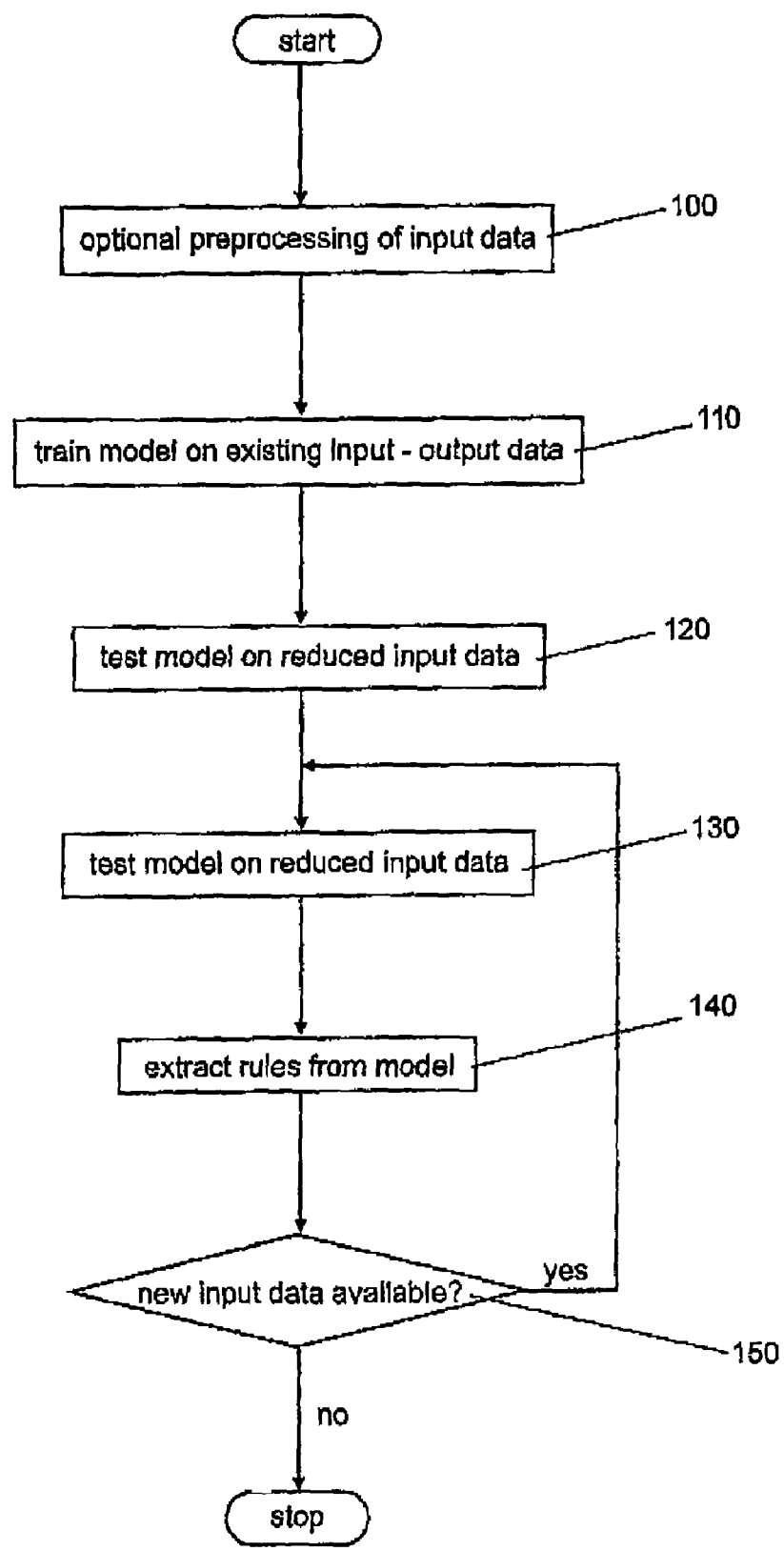
FIG. 2 is a flow chart illustrate a preferred method of the invention.
Figure 3:
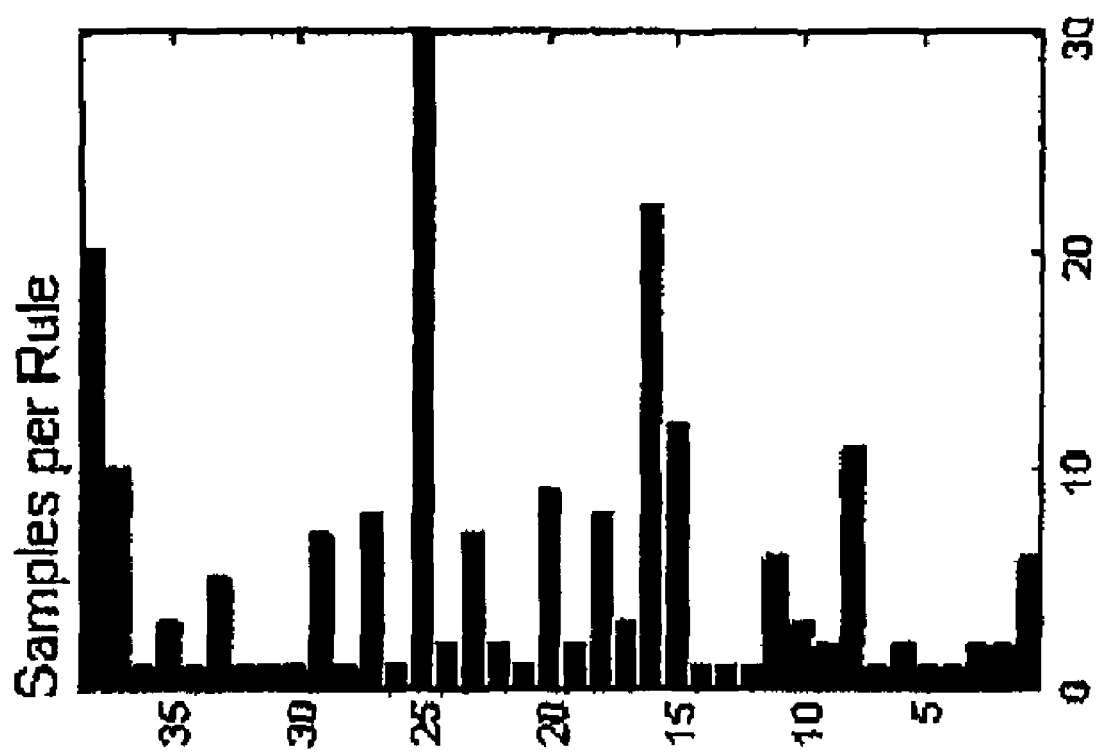
FIG. 3 shows rules for each cancer class extracted from a trained EFuNN.

FIG. 2 illustrates one method of disease profiling.

The input data optionally has preprocessing 100 performed on it. Such preprocessing includes filtering, correlation evaluation, normalisation, log transformation and/or noise reduction.

Input data and desired output data is used to train 110 the model. The training is performed by a sed learning algorithm, for example one of the supped learning algorithms described in WO 01/78003.

The model is tested 120 on reduced input data. In this example, the input data comprises 198 tumor samples and a separate model could be trained for each tumor sample, resulting in 198 models. Each model is trained on a reduced input data set for example 197 of the 198 samples and then tested on the sample not included in he reduced input data set. The error could then be evaluated and an average classification error calculated.

Table 1 sets out sample results from testing on reduced input data. It shows two different neural network models having different parameter values, trained on 139 selected genes out of 16,036 micro array gene expression data with the use of correlation statistic analysis to evaluate the relation between genes and classes for 14 classes of cancer data. The results show that the neural network of the invention is effective in reducing the genes linked to a particular condition. The results also show that a high degree of accuracy may be obtained predicting cancer outcome and cancer type.

Referring back to FIG. 2, following testing of the model or models on reduced input data, the reduced input data set that gives the best accuracy is chosen for a final classification system development and for extracting the profiles.

Described below are techniques and a methodology based on adaptive, learning, evolving connectionist systems (ECOS) for modelling, prognosis and rule extraction on the same gene expression data as in shipp et al but with the addition of clinical information that is available for the patients—the length of survival and the IPI (International Prognostic Index) number. Two experiments are presented.

In the first one, the same set of 11 genes as in Shipp et al is used to evolve a prognostic model. Using cross-validation (leave-one-out method) on the whole set of 58 samples (32 cured, and 26 fatal), 90% prediction rate (93% versus 14%, respectively) was obtained. The experiment employs evolving fuzzy neural networks (EFuNN) having the following parameters values: 3 membership functions for the input variables and no fuzzy representation for the output variables; max radius=1; 1 iteration of training.

TABLE 1

| Number of membership functions MF | Errthr - error threashold | Aggregation after every number of examples | Activation function: 1-linear; 2-RBF | Average Number of Rules | Leave-one-out method accuracy |
|---|---|---|---|---|---|
| 2 | 0.9 | — | 1 | 37.9 | 79.3 |
| 1 | 0.9 | 200 | 2 | 48.8 | 81.9 |

The model is then trained 130 based on the selected reduced input data as will be more particularly described in different applications below. Various rules may then be extracted 140 from the model. If there is new input data available 150, this new input data can then be used to further train the model or models.

Figure 4A:
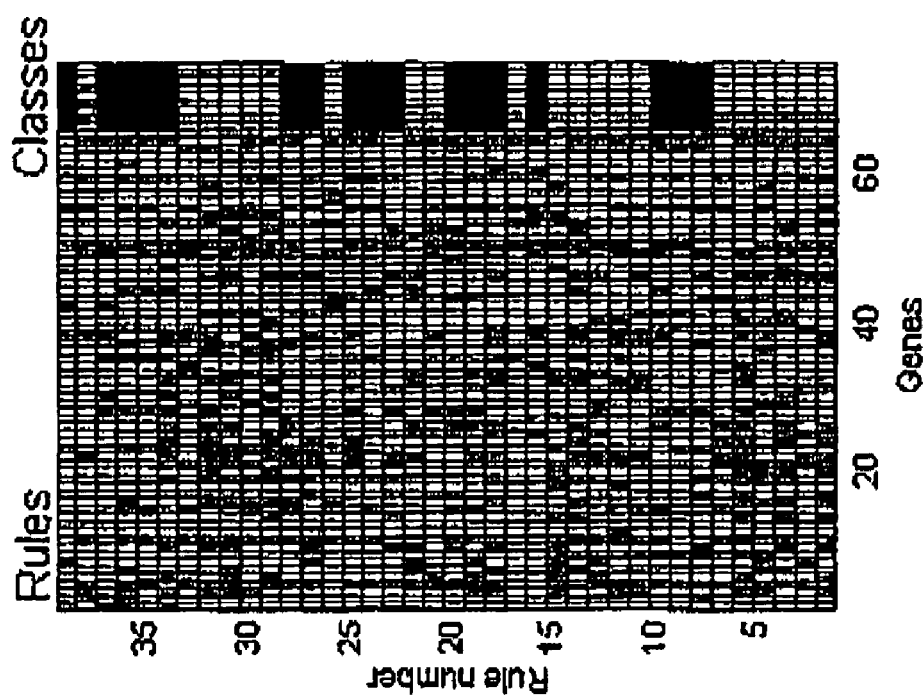
FIG. 4a shows gene expression level of genes for each of the genes identified as relevant by the EFuNN. Shaded areas indicate areas of underexpression.
Figure 4B:
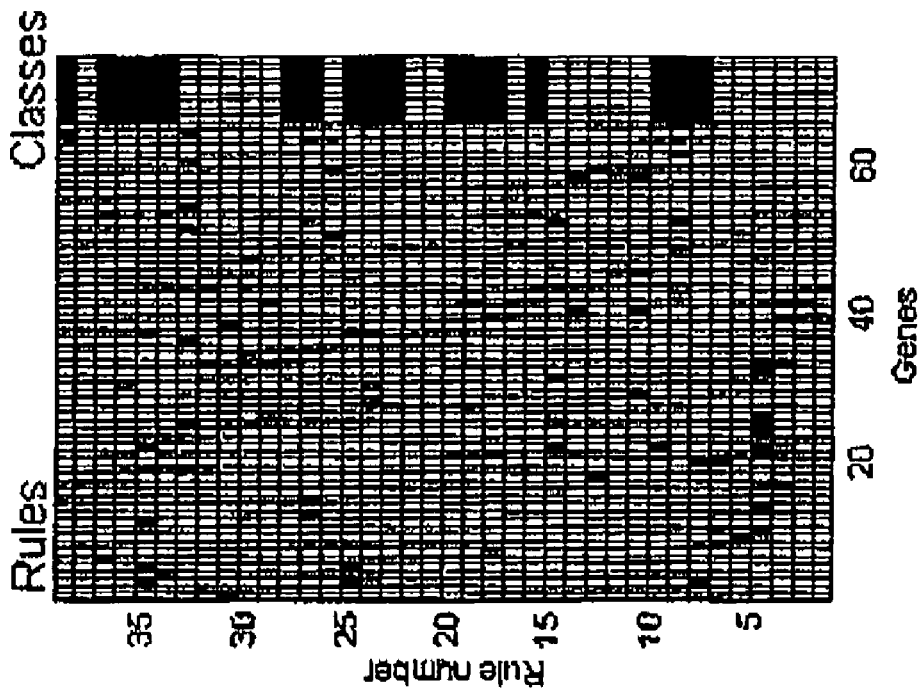
FIG. 4b shows gene expression level of genes for each of the genes identified as relevant by the EFuNN. Shaded areas indicate areas of overexpression.

FIG. 4 illustrates a set of 38 rules 200 over 60 genes 210. Each group of samples representing a class of cancer is represented by at least one rule and in many cases by several rules, each rule representing samples of a distinct cluster. A rule represents a profile of the input features, for example genes, that is characteristic for a cluster.

After the model was evolved from the data, each cluster of data that form a sub-class or a prototype is subsequently mapped with clinical information—the length of survival represented in months trough a fuzzy representation—short (1, less than 12 months), medium (2, between 20 and 40 months), long (between 40 and 60 months). Rules (profiles) of gene expression that characteristic each of these prototypes are extracted. The profiles identify different patterns of gene expression for each outcome class and each length of survival category.

The results can be visualised as in Table 2.

TABLE 2

| Name | Gene 1 Dystrophin related protein | Gene 2 Protein kinase C gamma | Gene 3 MINOR/NOR1 | Gene 4 PDE4B | Gene5 Protein kinase C beta-1 | Gene6 Zink-finger protein C2H2-150 |
|---|---|---|---|---|---|---|
| Class Cured | 0 | 58 | 58 | 58 | 58 | 43 |
| Class Fatal | 58 | 4 | 54 | 23 | 1 | 57 |

To find a common pattern between all clusters of the same class, an aggregation procedure is applied that results in a single profile for each class, depending on a threshold $C_{thr}$ used to select genes that have a higher value than this threshold value for any of their membership degrees. These higher values could include a high expression value or a low expression value.

A profile of class CI will include gene G is high, $G_h$, with a value of $G_h$, I, if $G_h$ appears in all rule nodes j that support class CI above the threshold $C_{thr}$, and the value $G_h$, I is calculated as the mean of all $G_h$ values across these rule nodes.

Figure 34A:
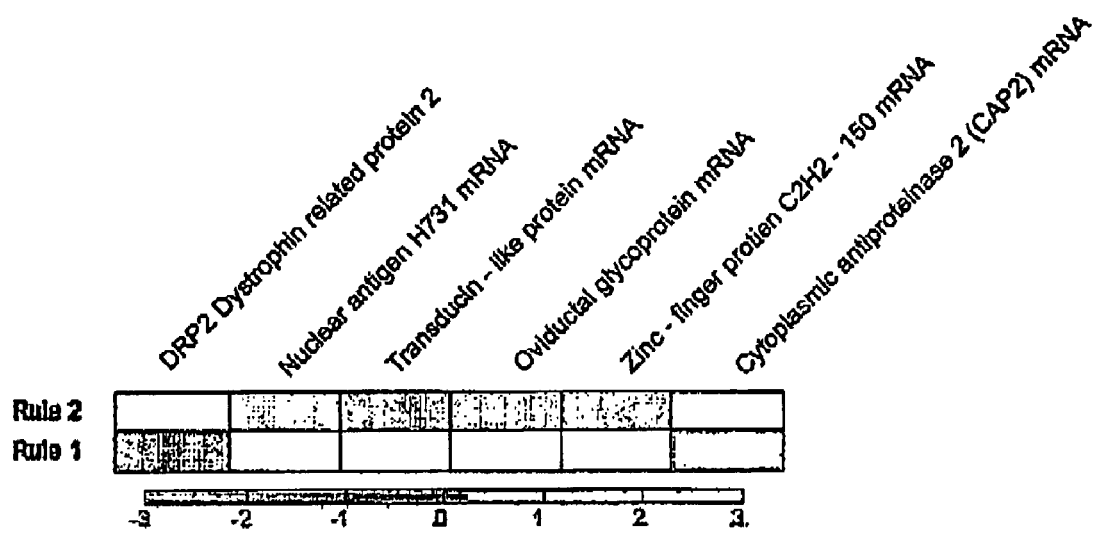
FIGS. 34a and 34b show prognostic outcomes of various cancer types using methods of the invention highlighting and cured conditions respectively.
Figure 34B:
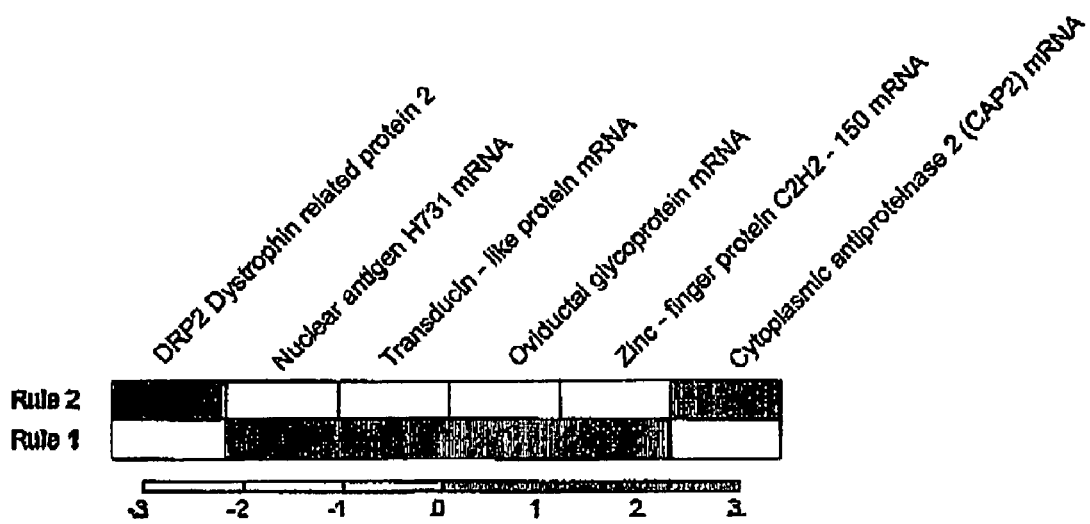

FIG. 34a shows in greyscale clusters of the fatal class, while FIG. 34b shows in greyscale clusters of the cured class. It can be seen that fatal cases of category 2 and 3 are closer in terms of gene expression profile to some of the cured. There is a significant difference between some of the fatal cases of category 1 and the fatal cases of category 2 and 3, which can be detected through gene expression and can be correctly predicted by the model. In addition to predicting a new case, the model can give as a result the highly matched prototype which will indicate a prognosis about the survival time for the new case.

As an example, one of the extracted rules from the trained EFuNN that defines a profile of the class fatal, category 1, is given below:

Rule 4:IF G3 is (Low 0.83) and G4 is (High 0.83) and G8 is (Medium 0.91) and G9 is (Low 0.83) and G11 is (Low 0.83) THEN Class is [fatal], where G1, etc are the genes listed in the same order as in Shipp et al (incorporated herein in full by reference).

In a second experiment, the same raw Affymetrix gene expression data of 6,817 genes for 58 patents as in Shipp et al is used, but separate models for each IPI class are created with the use of the same EFuNN technique with different parameter values. For each model, 5 genes are selected out of the initial 6,817 using the same signal to noise ratio analysis as in Shipp et al. The accuracy of the prognosis (cured vs fatal) four each IPI class model is as follows: for IPI=1 (low), 91.9±3.9; for IPI=2 (low intermediate), 96.4±5.7, for IPI=3 (high intermediate), 90.4±6.1; IPI=4 the prognosis is 100% as all classes belong to the class 'fatal'.

The samples were stratified according to their IPI:

IPI=low: 26 samples, of which 19 belong to the cured class and 7 to the fatal class.

IPI=low intermediate: 11 samples, of which 7 belong to the cured class and 4 to the fatal class.

IPI=high intermediate: 17 samples, of which 4 belong to the cured class and 13 to the fatal class.

IPI=high: 2 samples, of which 2 belong to the fatal class. No further classification by microarray data necessary.

IPI=unknown: 2 samples. These samples were not considered here.

For each of the 3 IPI categories, gene selection and prognosis was performed on a N-cross validation basis. First, 5 genes were selected for each IPI in each cross validation run. Classification was performed by EFuNN with the following parameter values: membership functions MF=2, error threshold Errth=0.1, no aggregation applied; Euclidean distance for measuring the similarity between input vectors; radial basis activation function for the rule nodes in the EFuNN model; 3 iterations over the training data set in each cross validation model. Running 30 N-cross validation procedures for each IPI group, the classification performance was assessed as shown in Table 3.

TABLE 3

Test accuracy in the N-cross validation experiments for the three IPI models

| IPI | Low | Low intermediate | High intermediate |
|---|---|---|---|
| Original group | 91.9 ± 3.9 | 96.4 ± 5.7 | 90.4 ± 6.1 |

As a baseline, groups with number of samples and the same class percentage with random IPI selection were formed. In this case the accuracy is lower and variation is higher, e.g., the variation for each of the three models is respectively:±6.4, ±9.9, ±6.5.

After the cross-validation of the EFuNN models, all examples were used to build the final prognostic models with the use of reduced gene set of 5 genes as defined in the previous step (table 4). Rules were extracted from the trained EFuNNs, each rule representing a profile of a group (cluster) of samples from the 5 dimensional space. Gene expression profiles can be used not only to predict the outcome of DLBCL patient treatment in one of the 3 IPI categories in a clinical environment, but to direct research of pharmaceutical companies towards new drug targets.

TABLE 4

Selected genes in the cross validation EFuNN modelling for each of the IPI categories

| Category | A set of selected genes |
|---|---|
| IPI = 1 (low) | 'KIAA0278 gene, partial cds' 26 |
| | 'Gene encoding prepro form of corticotropin releasing factor' 25 |
| | 'DBH Dopamine beta-hydroxylase (dopamine beta-monooxygenase)' 25 |
| | 'SP4 Sp4 transcription factor' 14 |
| | 'CCAAT BOX-BINDING TRANSCRIPTION FACTOR 1' 14 |
| IPI = 2 (low intermediate) | 'LIM domain protein CLP-36 mRNA' 10 |
| | 'CES2 Carboxylestease 2 (liver)' 9 |
| | 'KIAA0197 gene, partial cds' 7 |
| | 'LYZ Lysozyme' 3 |
| | 'ApM2 mRNA for GS2374 (unknown product specific to adipose tissue)' 2 |
| IPI = 3 (high intermediate) | 'HPrp18 mRNA' 15 |
| | 'KIAA0036 gene' 15 |
| | 'D-aspartate oxidase' 15 |
| | 'Partial mRNA for pyrophosphatase' 12 |
| | 'JNK activating kinase (JNKK1) mRNA' 5 |

EXAMPLE 3

The gene expression database published by (Ramaswamy et al.) aud publicly available from (http://www-genome.wi.mit.edu/MPR/GCM.html) is used in this example. This database is incorporated herein by reference. This database contains gene expression values for 90 normal tissue samples and 218 tumor samples from 14 common tumor types. Each sample has the expression level of 16,063 genes and expressed sequence tags (ESTs). 20 of the tumor samples were shown by Ramaswamy et al. to be poorly differentiated resulting in unsatisfactory classification. As we intend to identify patterns in gene expression values that differentiate between tumor types, we used the tumor samples from the database excluding the poorly differentiated samples.

A system to identify patterns (profiles) of gene expression values in each of the 14 tumor classes considered here was developed by applying the feature selection method above and minimised the feature space of the case study data from (Ramaswami et al) from 16,063 to 399 genes. This data set was then used to train an to EFuNN to model patterns of gene expression in each of the 14 tumor classes. Rules were extracted from the EFuNN that describe the expression levels of genes for a particular class. A class can be represented by more than one rule, but each rule describes only one class.

A pattern for each tumor class was then generated by combining all tie rules relating to that class. A gene is included in the pattern if the membership degree of its expression level (HIGH/LOW) is above a given threshold in all rules relating to that particular class. The threshold gives an indication of the characteristics of the features in the pattern. In this instance the threshold indicates the importance of the genes in the pattern. For example if gene g is present in the profile of Breast Adenocarcinoma when the threshold is 0.9, it is likely that this is an important gene for this class. That is, the membership degree of this gene in the rules extracted from the EFuNN is above 0.9 in all rules related to this class. In some cases the threshold must be set relatively low. This does not mean that the feature (gene) is not important, just that it is not a strong feature in this pattern even though it is common to all rules related to that class.

Figure 5A:
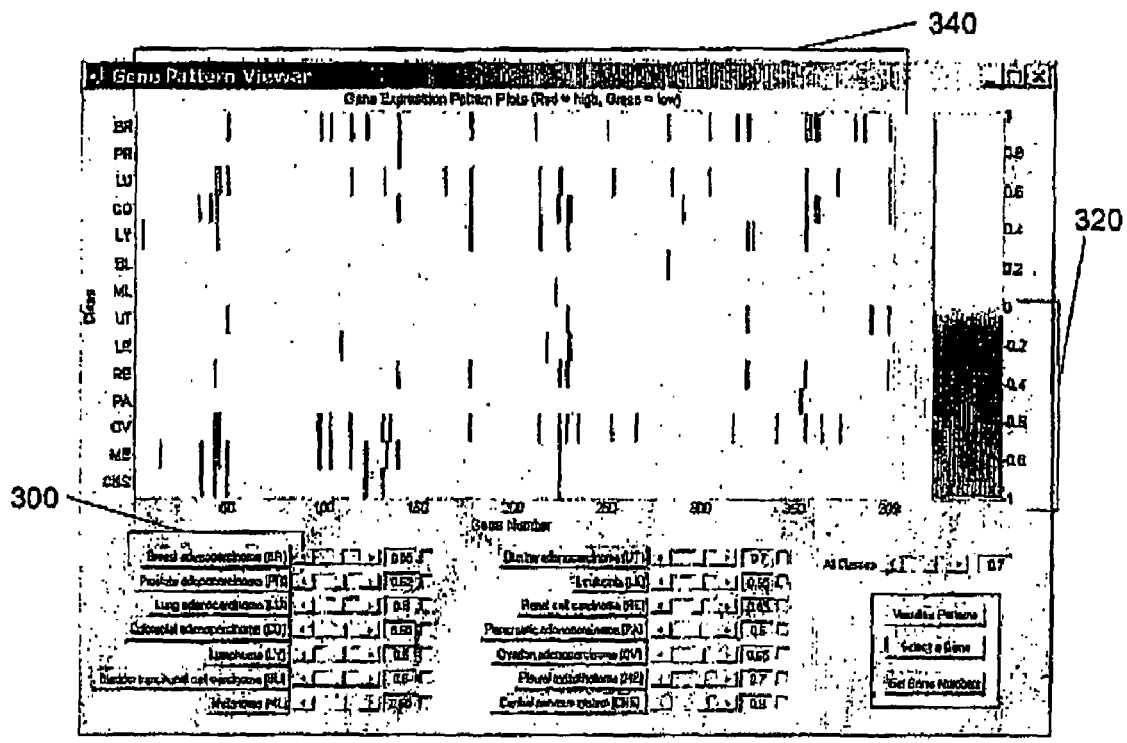
FIG. 5a shows class profiles for 14 types of cancer extracted through applying the methods of the invention highlighting genes that are underexpressed.
Figure 5B:
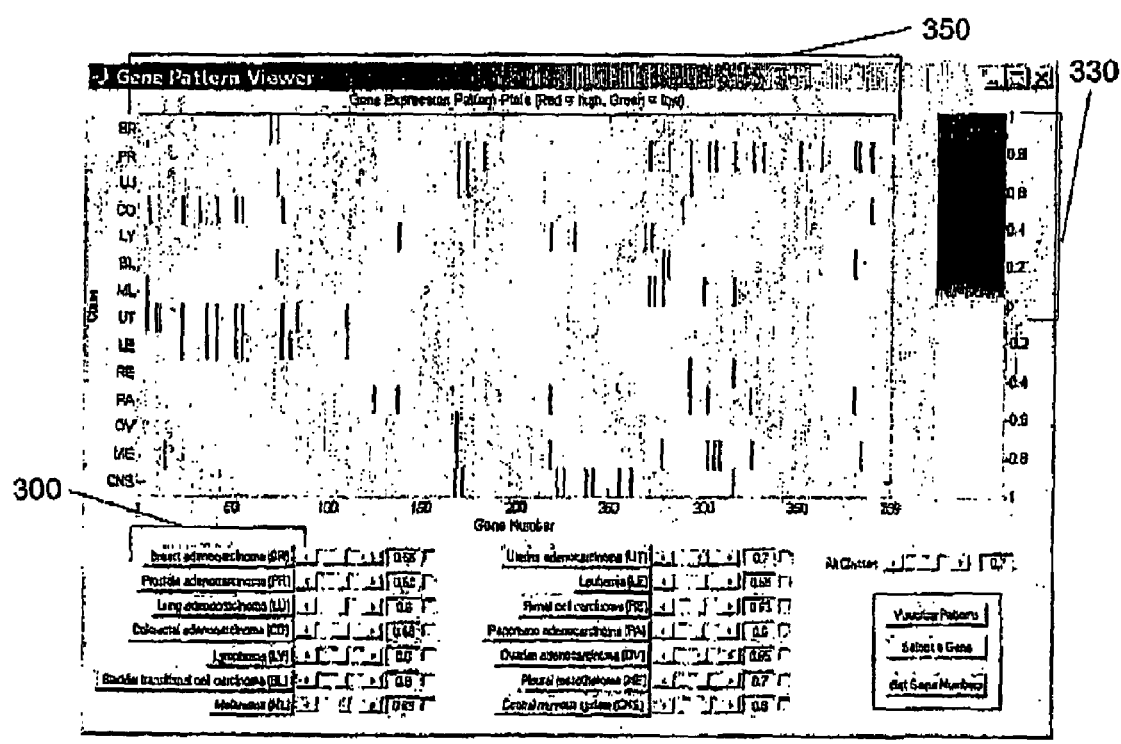
FIG. 5b shows class profiles for the 14 types of cancer in FIG. 5a highlighting genes that are overexpressed.

The graphical representation is given in FIGS. 5a and 5b. Class profiles of different types of cancer 300 are extracted. The profiles of each class can be modified through a threshold $C_{thr}$ defining a membership degree above which a gene should be either over-expressed or under-expressed in order to appear in the is profile.

A graduated scale 320 indicates levels of underexpression of genes shown in greyscale in the left top large pane 340, whereas the other graduated scale 330 indicates levels of overexpression of genes in the left top large pane 350. The profiles of each class can be modified through a threshold $C_{thr}$ tuned for each individual class that defines the membership degree above which a gene should be either over-expressed or under-expressed in all rules of this class in order for this gene to appear in the profile. Each Class of cancer is represented by only one pat that resents the common genes in all tissue samples of Ibis class either under-expressed, or over-expressed. In addition to this combined class patterns, for each class several subgroups (clusters) can be identified by the method and the characteristic pattern of each sub group of the same class can be extracted. In the tables below, lint th class profiles are extracted, and second for each class—the sub-group profiles are extracted too for a defined threshold that can be modified. Through lowering threshold, more detailed profiles are extracted.

A pattern is shown on the graph for each of the 14 tumor classes. A line represents in pane 350 a high expression level for a gene and a line in pane 340 represents a low expression level for a gene. The relative strength of these colours represents the average membership degree for a gene, indicating the strength of the gene's participation in the rule. The graphical interface also allows the user to view the individual rules, as shown in figures (b) afterwards. This allows a visual interpretation of the rules that make up a particular pattern. This may be useful, especially when a pattern appears not to show any common genes. When viewing the individual rules it may be possible to identify genes of interest that do not necessarily appear in all the rules.

Accuracy was evaluated in the case of lymphoma, when the used threshold is 0.6, there are 13 genes selected. The accuracy of the model is 97%. In order to select a minimum number of genes, different models are created out of the 13 genes, starting from 1 gene and their accuracy is evaluated, so that the ratio (Number of Genes)/Accuracy is optimized. For example, sing gene D64142 gives and accuracy of 64%, but adding two other genes brings the accuracy (confidence) to 95%.

It is not the intention to limit the scope of the invention to the abovementioned examples only. As would be appreciated by a skilled person in the ark many variations aro possible without departing fm the scope of the invention (as set out in the accompanying claims).

Figure 6:
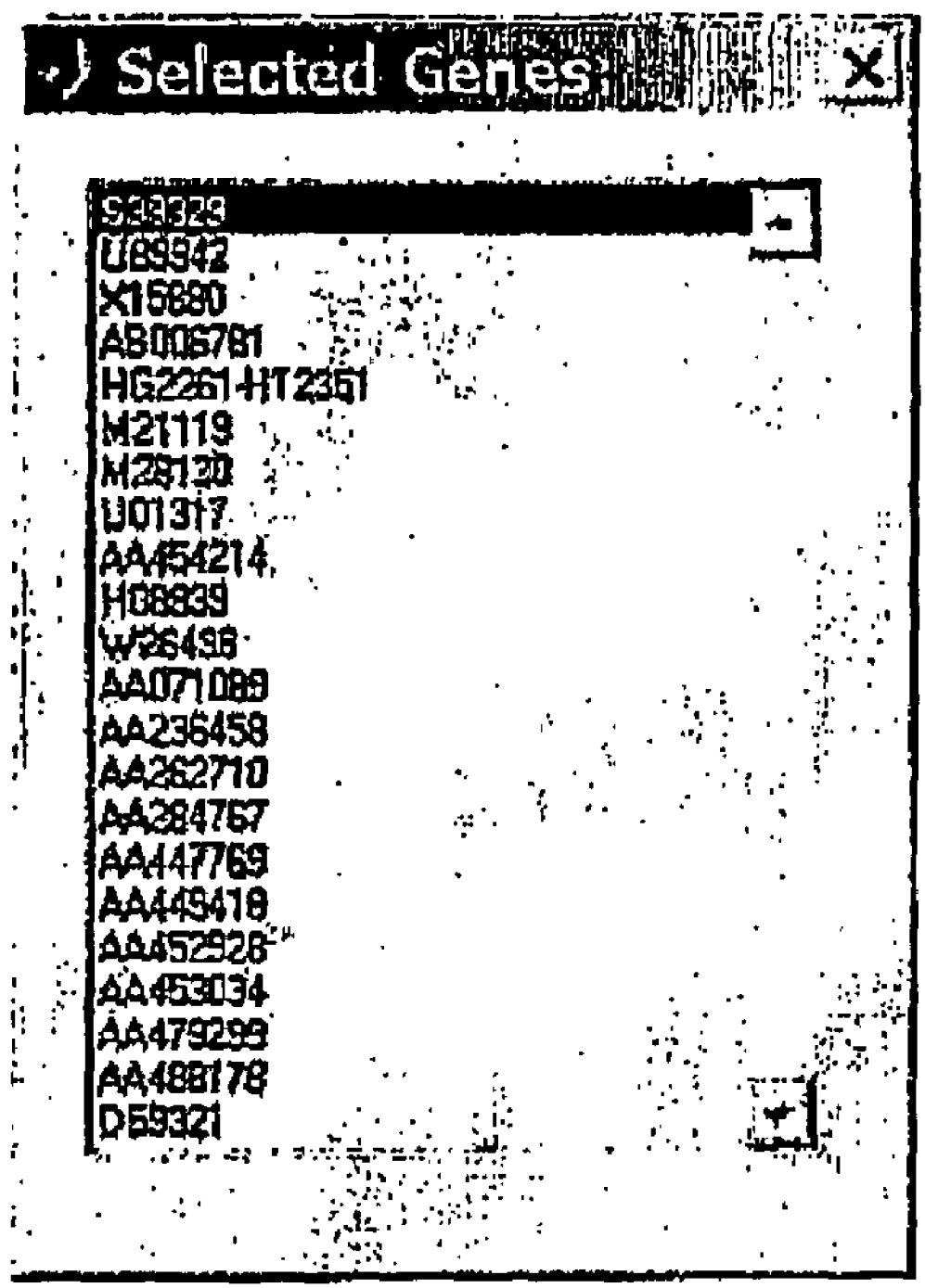
FIG. 6 shows a gene expression class profile of Breast adenocarcinoma genes.
Figure 7A:
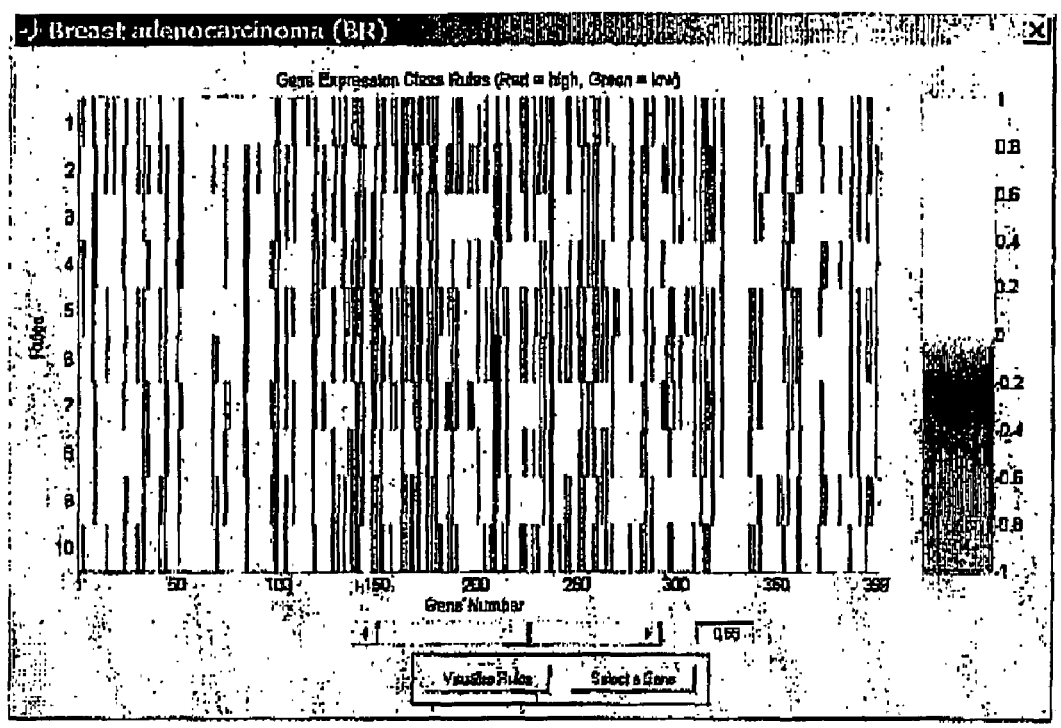
FIG. 7a shows 10 gene expression subgroup profiles for Breast adenocarcinoma highlighting underexpressed genes.
Figure 7B:
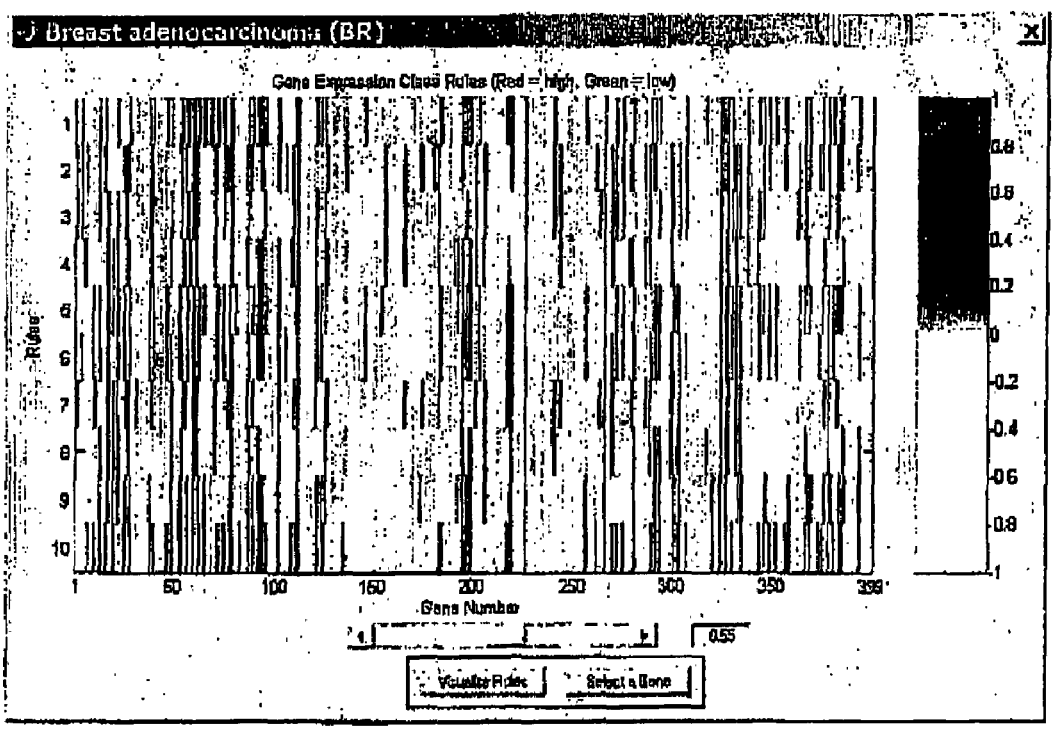
FIG. 7b shows 10 gene expression subgroup profiles for Breast adenocarcinoma highlighting overexpressed genes.

FIG. 6 shows a gene expression class profile of Breast adenocarcinoma gene as opposed to the profiles of the other 13 types of cancer considered here. The genes are represented by their GenBank accession number, which is a unique number corresponding to the gene name. Genes numbered on the list with the following order numbers are over-expressed: 2,3. The rest of the genes are under-expressed. Minimum level of fuzzy membership degree of over-, or under expression is 0.55. FIG. 7a shows the 10 gene expression subgroup profiles for Breast adenocarcinoma highlighting underexpressed genes. FIG. 7b shows the same data but highlighting overexpressed genes.

Figure 8:
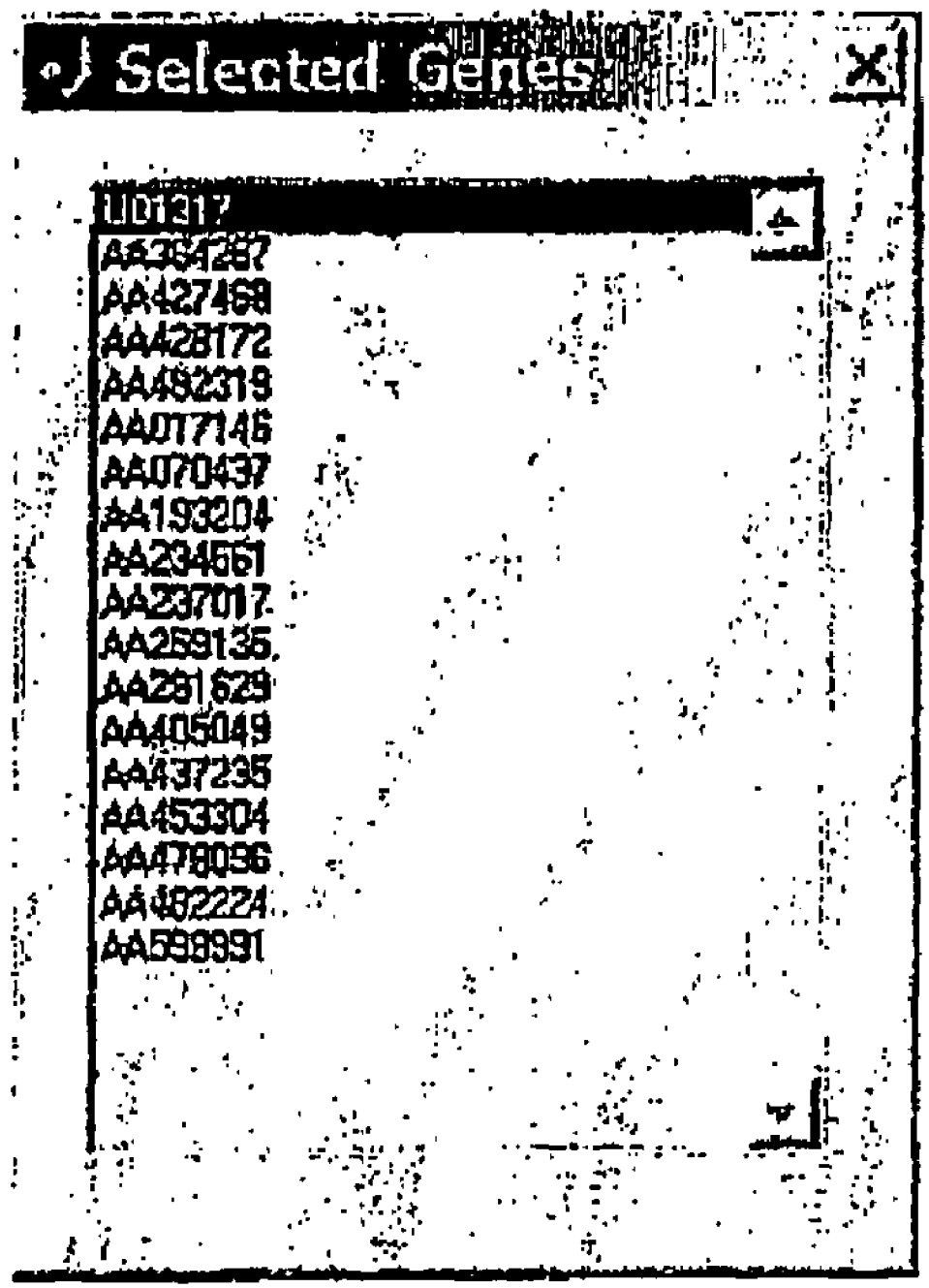
FIG. 8 shows a gene expression profile of prostate cancer genes.
Figure 9A:
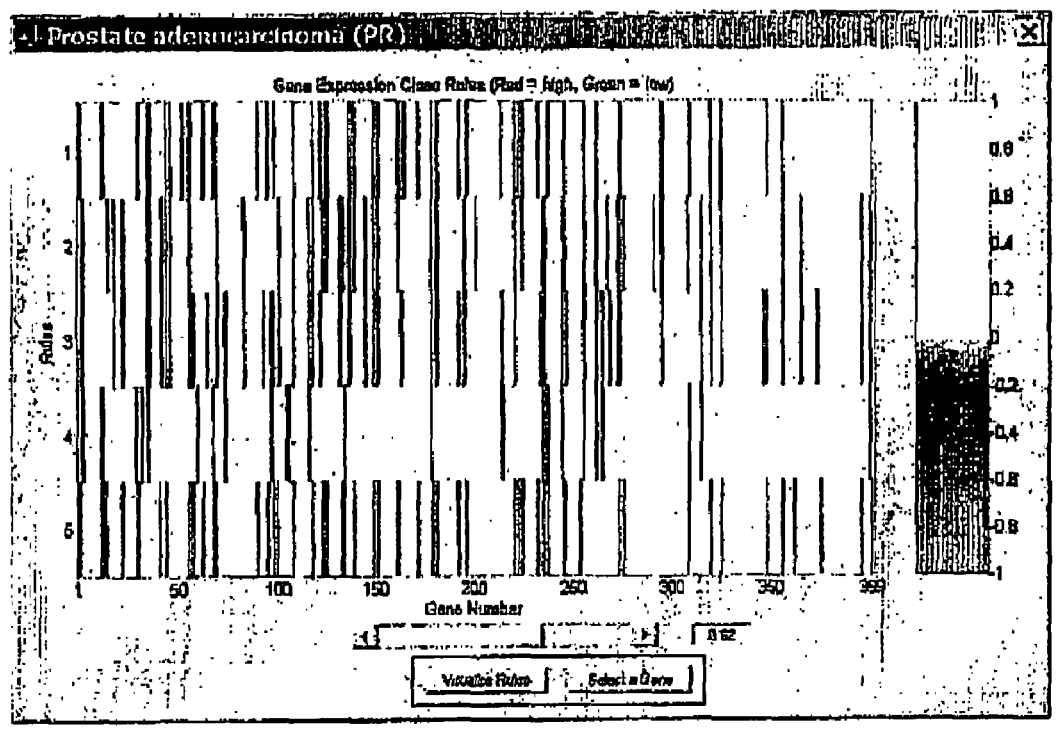
FIG. 9a shows 5 gene expression subgroup profiles for prostate cancer highlighting underexpressed genes.
Figure 9B:
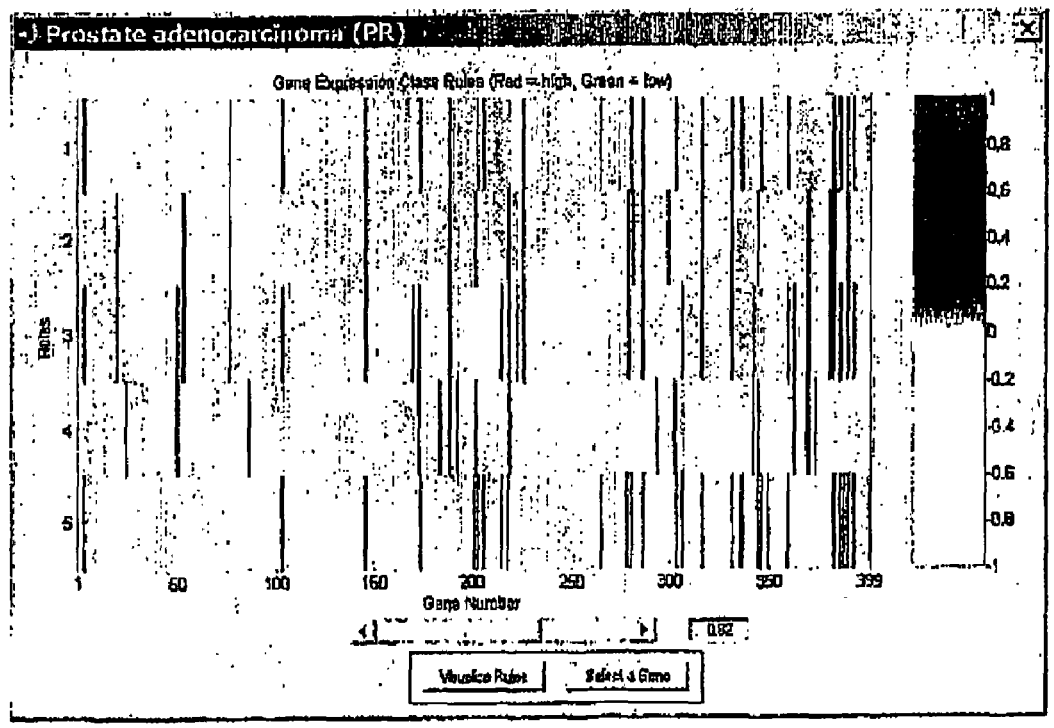
FIG. 9b shows 5 gene expression subgroup profiles for prostate cancer highlighting overexpressed genes.

FIG. 8 shows a gene expression profile of prostate cancer genes as opposed to the profiles of the other 13 types of cancer considered here. The genes are represented by their GenBank accession number. Genes numbered on the list with te following order numbers are underexpressed. The rest of the genes are overexpressed. The minimum level of fuzzy membership degree of over-, or under expression is 0.62. FIGS. 9a and 9b show the 5 gene expression on subgroup profiles for prostate cancer highlighting underexpressed and overexpressed genes respectively.

Figure 10:
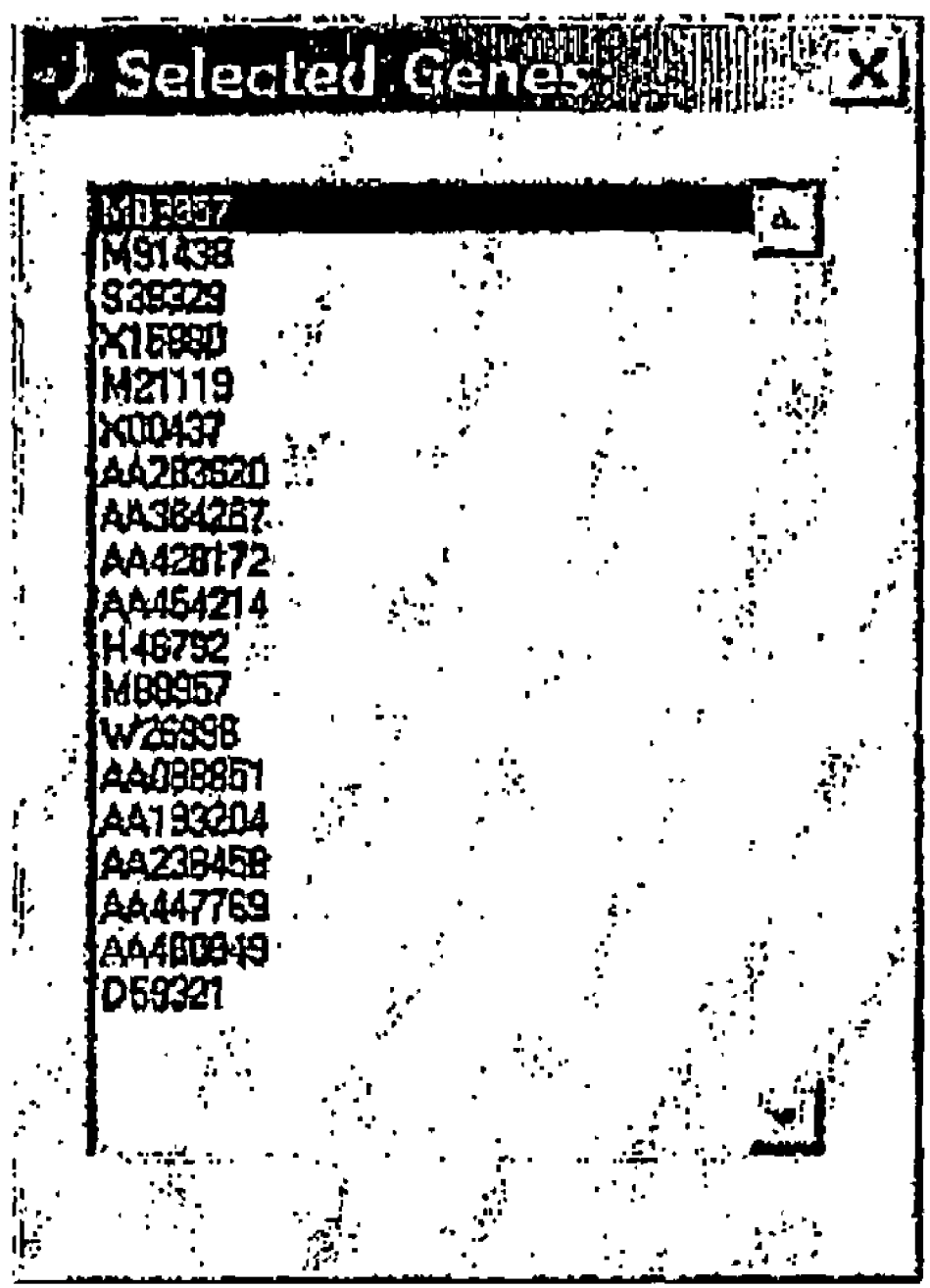
FIG. 10 shows the gene expression profile of lung adenocarcinoma genes.
Figure 11A:
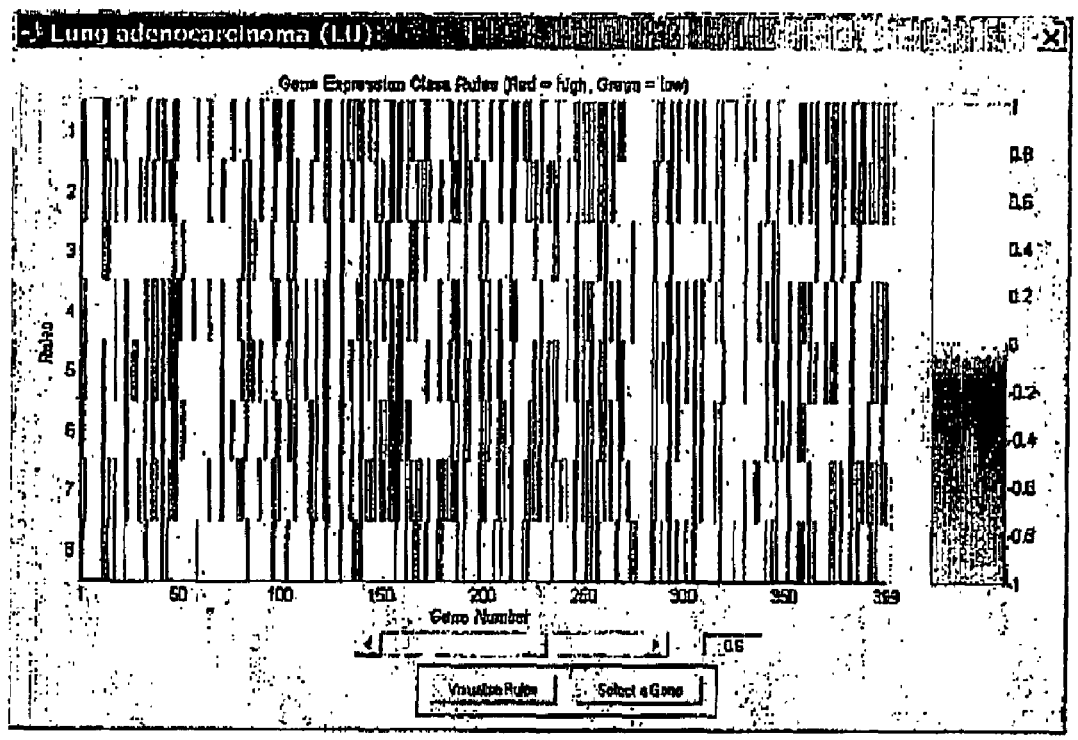
FIG. 11a shows 8 gene expression subgroup profiles for Lung adenocarcinoma highlighting underexpressed genes.
Figure 11B:
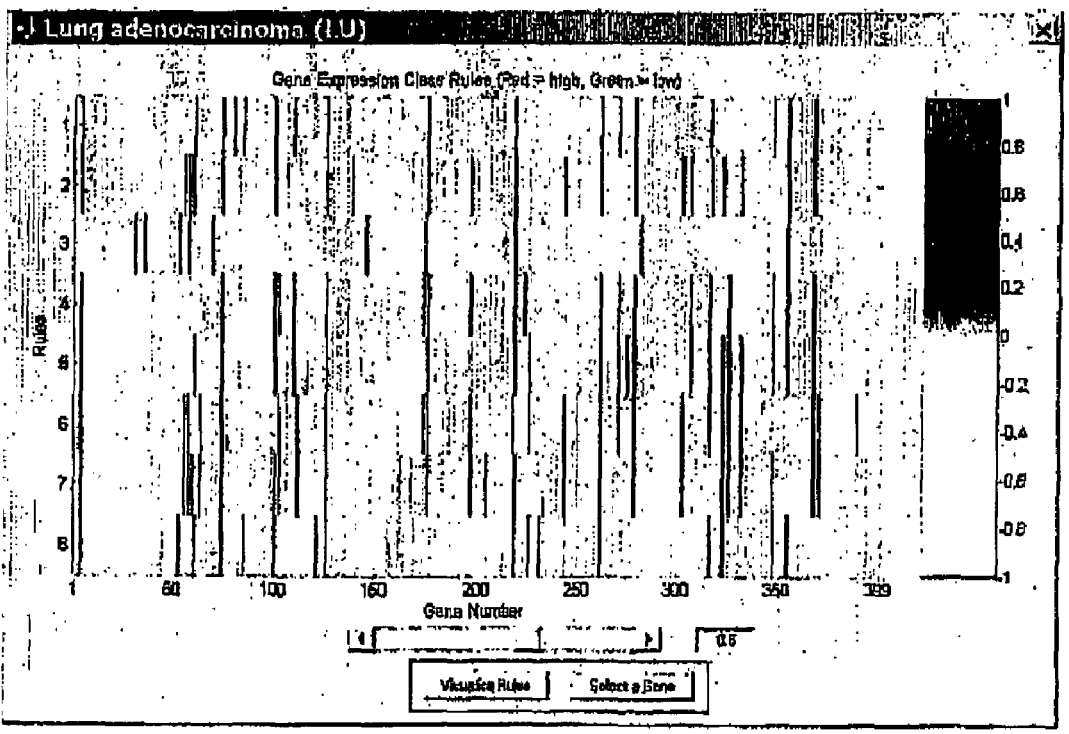
FIG. 11b shows 8 gene expression subgroup profiles for Lung adenocarcinoma highlighting overexpressed genes.

FIG. 10 shows the gene expression profile of Lung adenocarcinoma genes as opposed to the profiles of the other 13 types of cancer considered here. The genes are represented by their GenBank accession number. Genes numbered on the list with the following order numbers are under expressed: 4,8,9,15. The rest of the genes are over-expressed. The minimum level of fuzzy membership degree of over-, or under expression is 0.6. FIGS. 11a and 11b show 8 gene expression subgroup profiles for lung adenocarcinoma highlighting underexpressed and overexpressed genes respectively.

Figure 12:
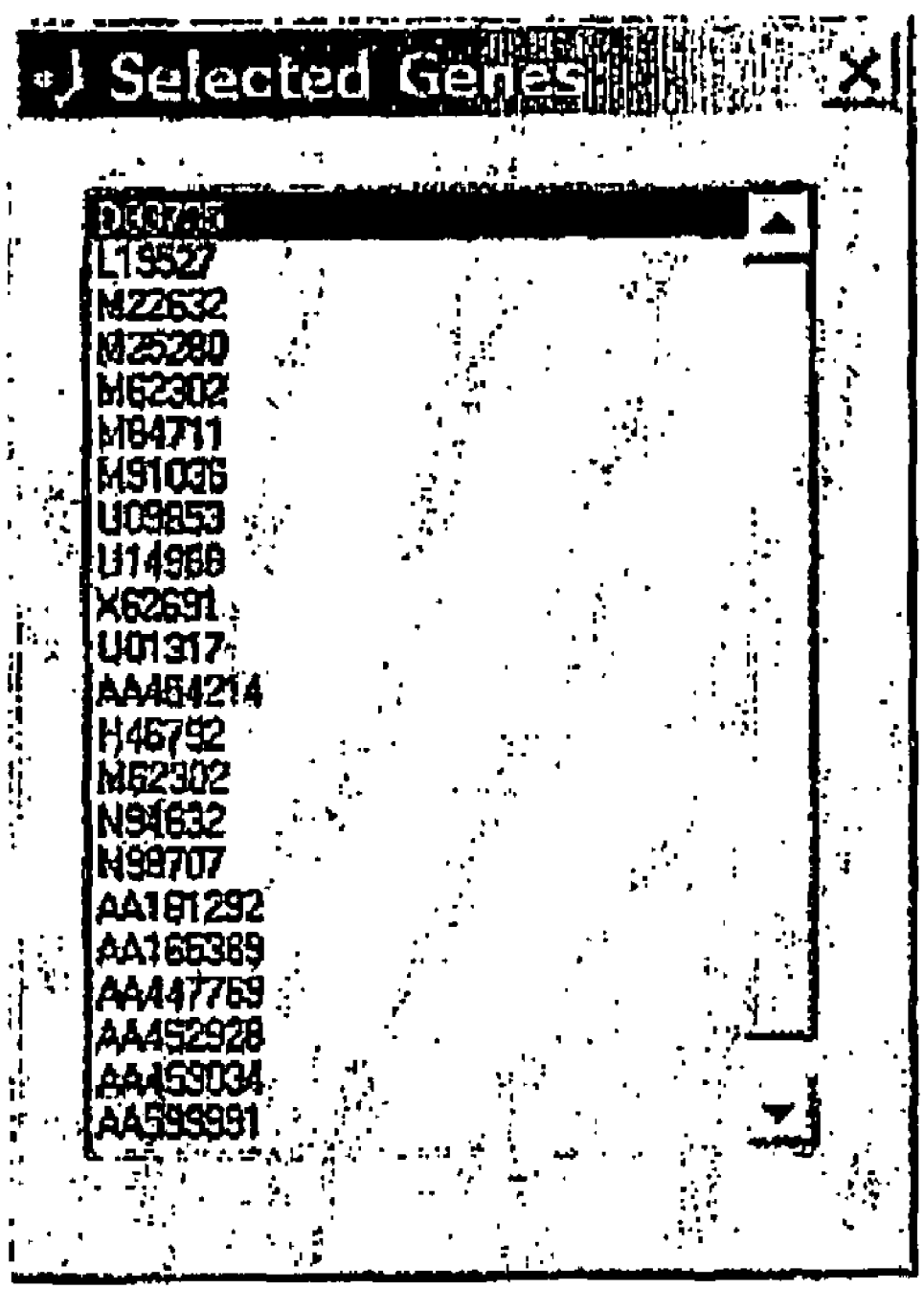
FIG. 12 shows the gene expression profile for Colorectal adenocarcinoma genes.
Figure 13A:
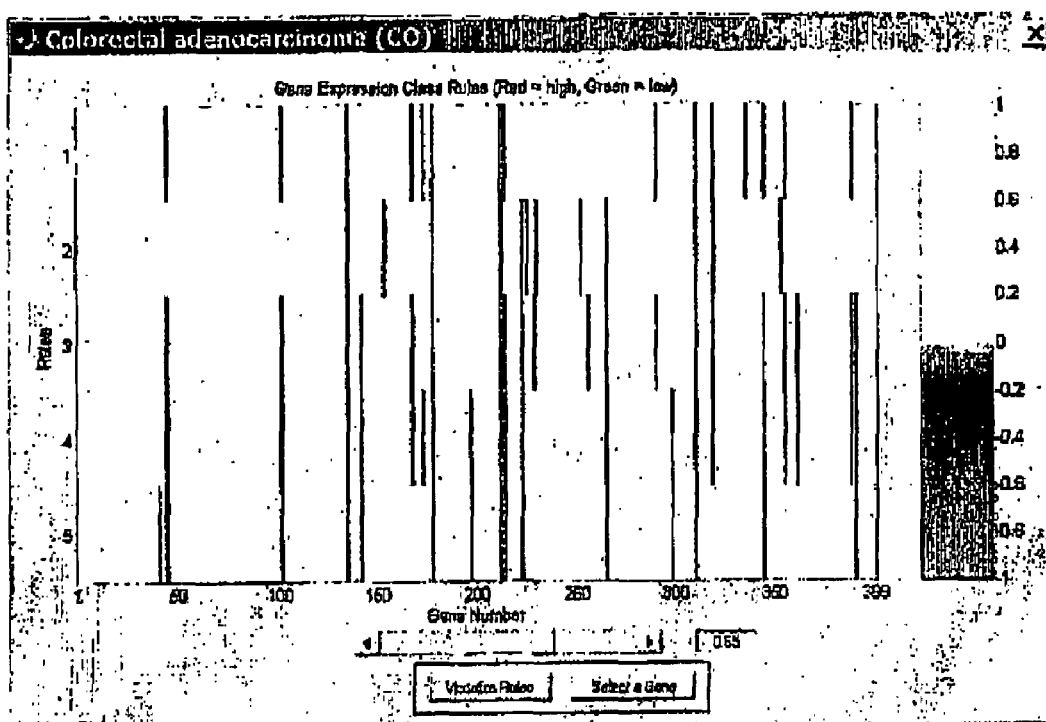
FIGS. 13a and 13b show the 5 gene expression subgroup profiles for Colorectal adenocarcinoma highlighting underexpression and overexpression respectively.
Figure 13B:
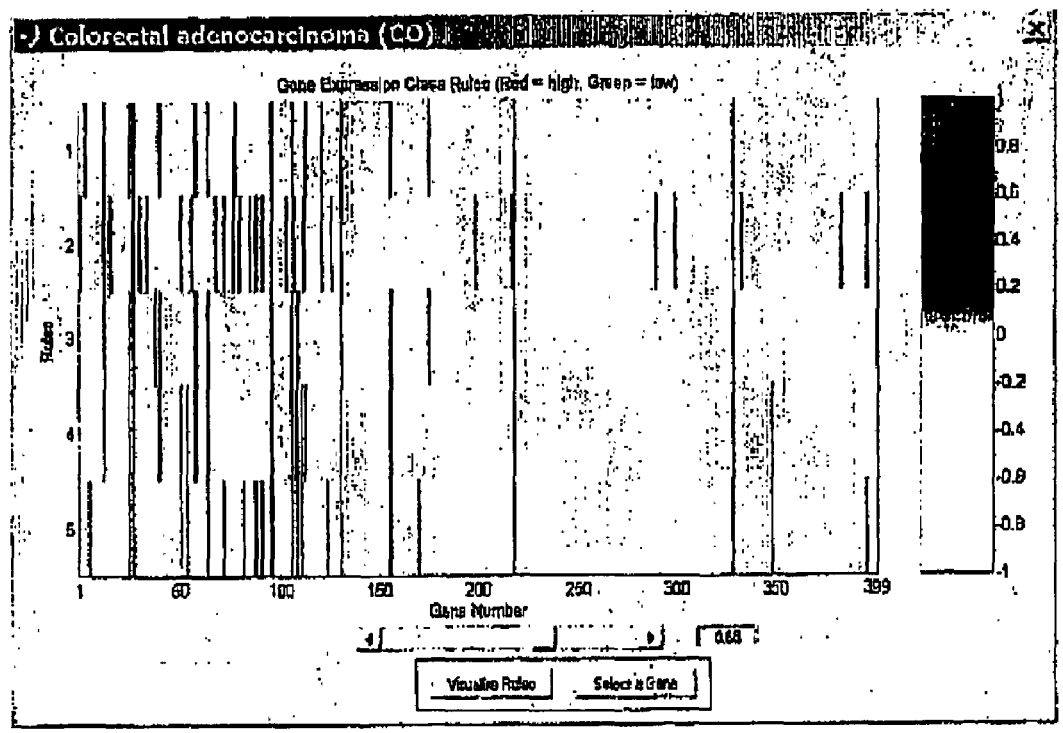

FIG. 12 shows the gene expression profile for colorectal adenocarcinoma genes as opposed to the profiles of the otter 13 types of cancer considered here be genes are represented by their GenBank accession number. Genes numbered on the list with the following order members are over-expressed: 1,2,3,6,8,9,10,17,22. The rest of the genes are under-expressed. The level of fuzzy member degree of over-, or under expression is 0.65. FIGS. 13a and 13b show the 5 gene expression subgroup profiles for Colorectal adenocarcinoma highlighting underexpressed and overexpressed genes respectively.

Figure 14:
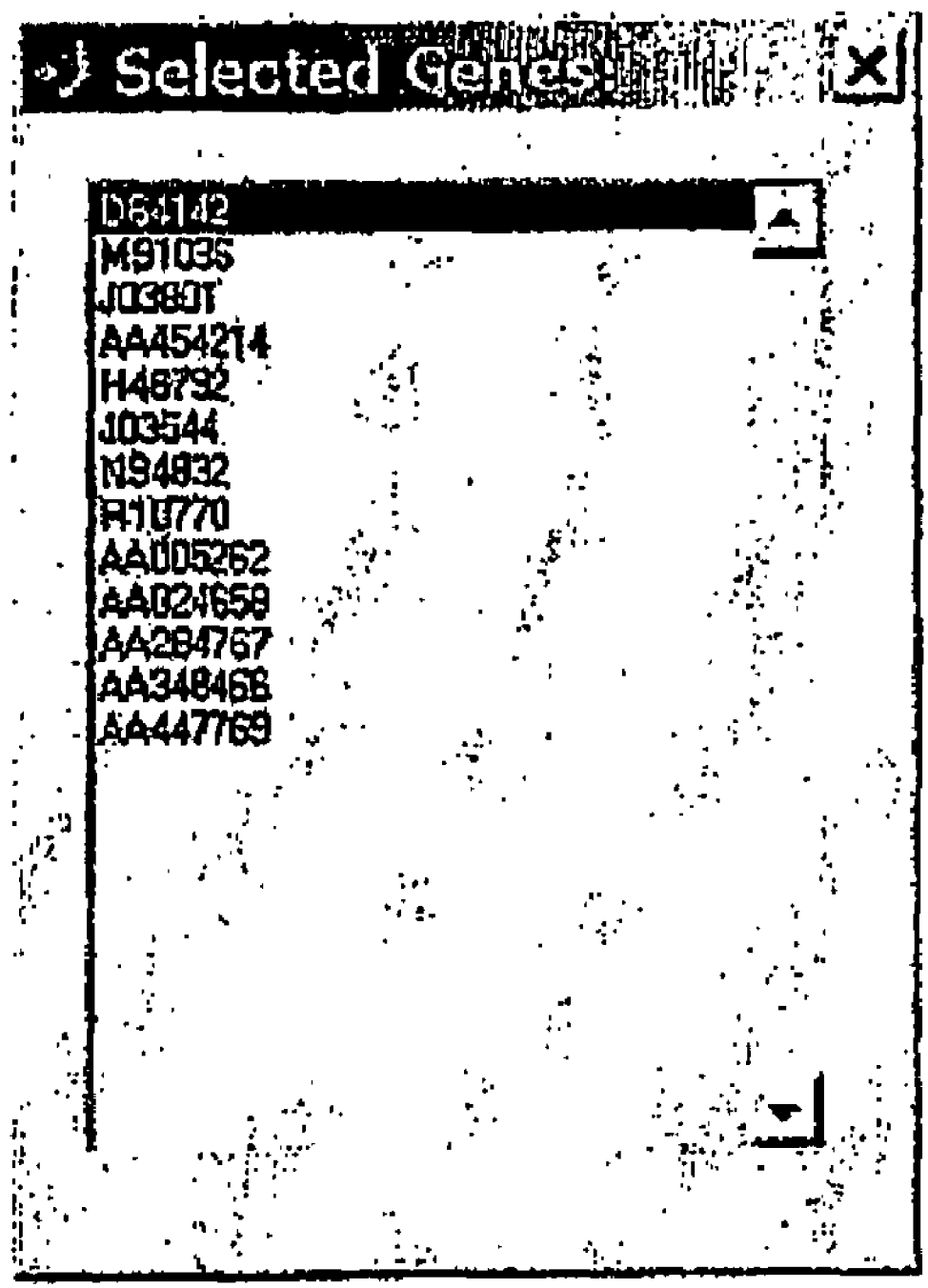
FIG. 14 shows the gene expression profile for Lymphoma genes.
Figure 15A:
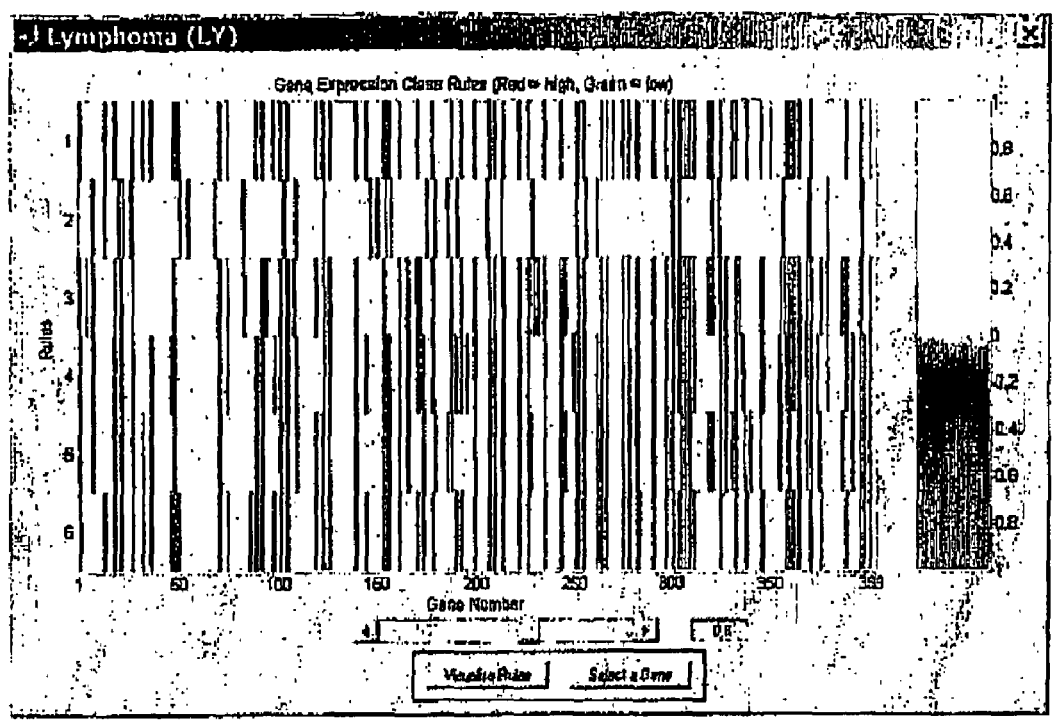
FIGS. 15a and 15b show the 6 gene expression subgroup profiles for Lymphoma highlighting underexpression and overexpression respectively.
Figure 15B:
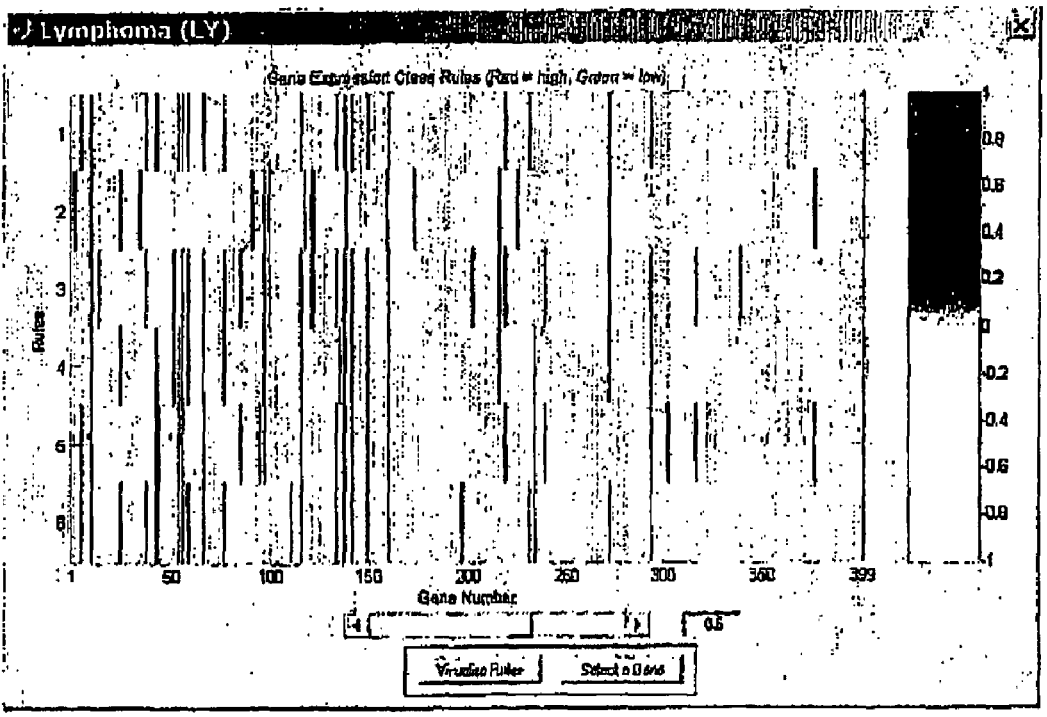

FIG. 14 shows the gene expression profile for Lymphoma genes as opposed to the profiles of the other 13 types of cancer considered here. The genes are represented by their GenBank accession number. Genes numbered on the list with tile following order numbers are over pressed: 3,6,8, 9,10. The rest of the genes are under-expressed. The minimum level of fuzzy membership degree of over-, or under expression is 0.6. FIGS. 15a and 15b show the 6 gene expression subgroup profiles for lymphoma highlighting underexpressed and overexpressed genes respectively.

Figure 16:
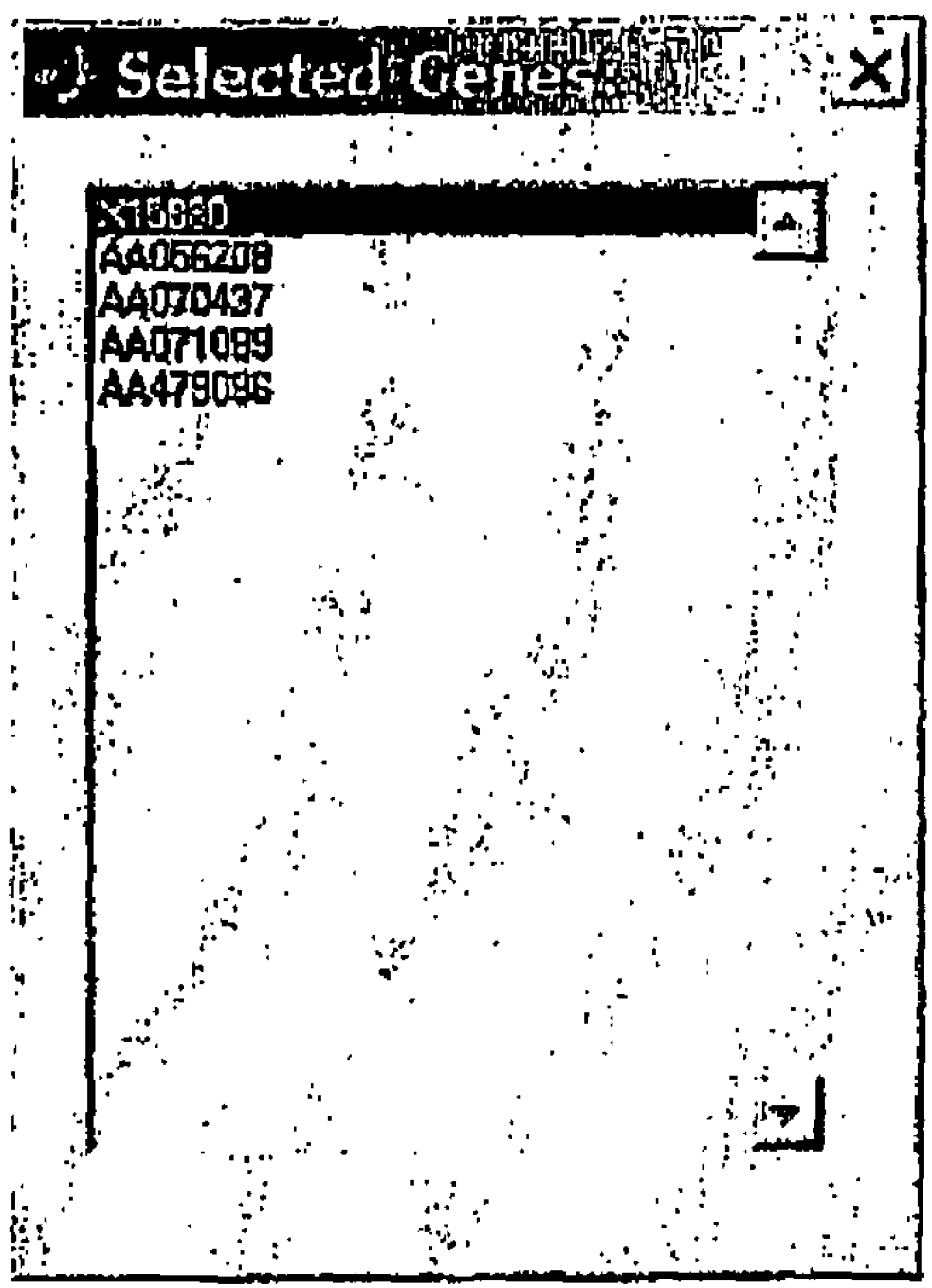
FIG. 16 shows the gene expression profile for Bladder transitional cell carcinoma genes.
Figure 17A:
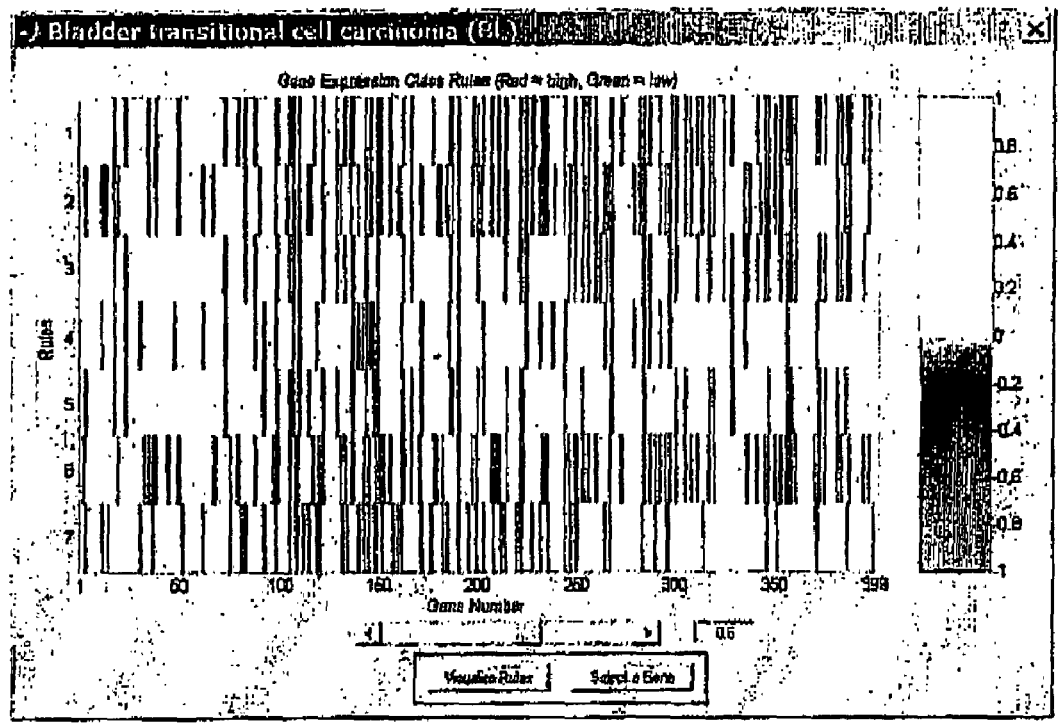
FIGS. 17a and 17b show the 7 gene expression subgroup profiles for Bladder transitional cell carcinoma highlighting underexpression and overexpression respectively.
Figure 17B:
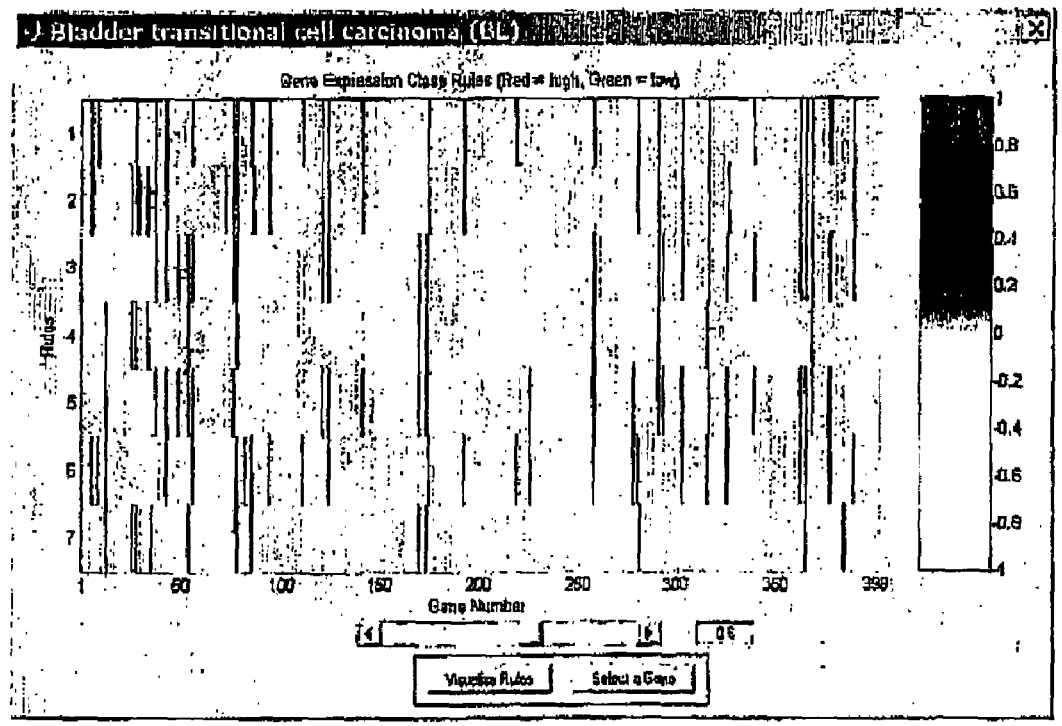

FIG. 16 shows the gene expression profile for Bladder transitional cell carcinoma genes as opposed to the profiles of the other 13 types of cancer considered here. The genes are represented by the GenBank accession number. Genes numbered on the list with the follow order numbers are over-expressed: 1,2,3,5. The rest of the genes are under-expressed, The minimum level of fuzzy membership degree of over-, or under expression is 0.6. FIGS. 17a and 17b show the 7 gene expression subgroup profiles for Bladder transitional cell carcinoma highlighting underexpressed and over-expressed genes respectively.

Figure 18:
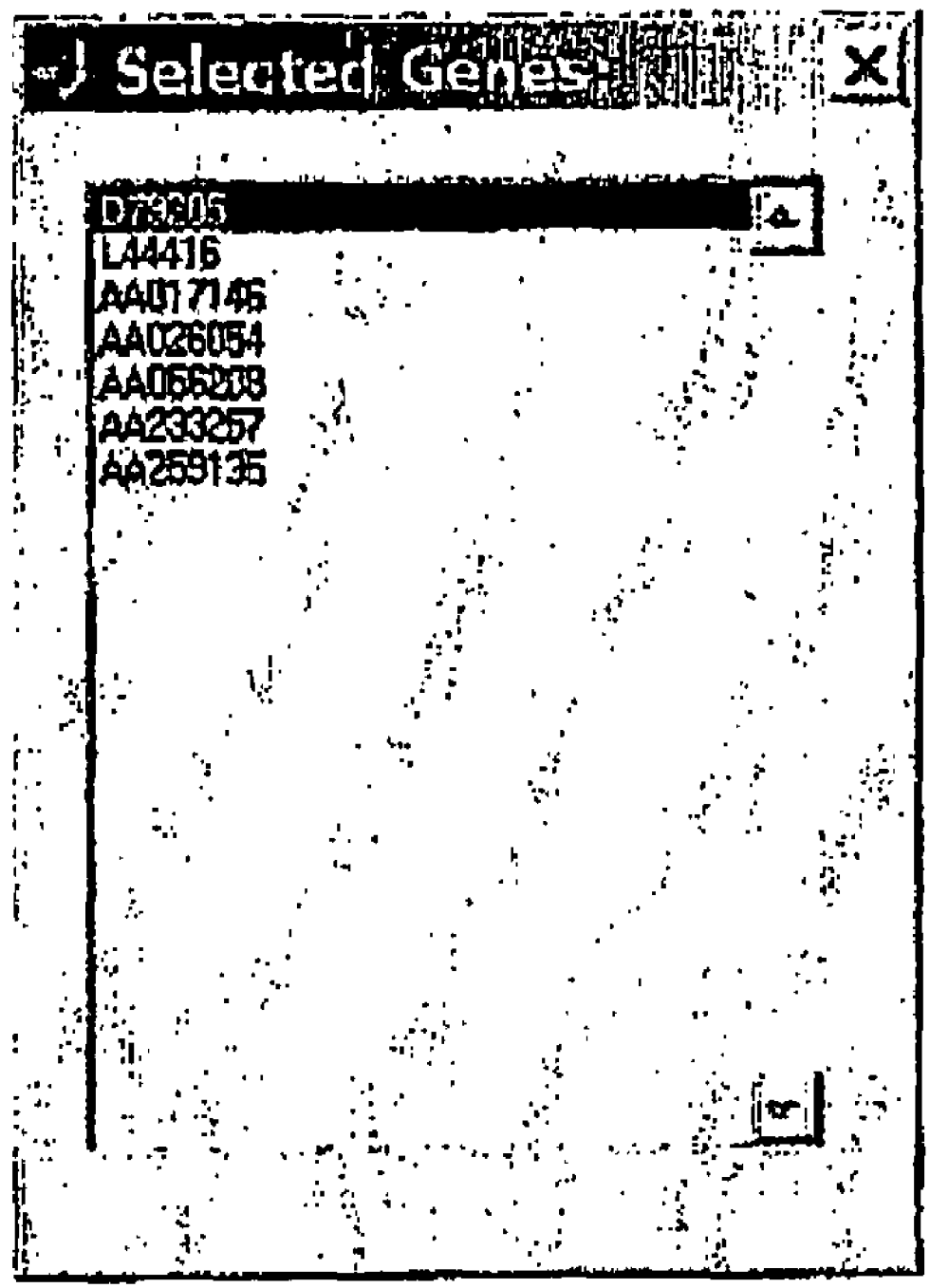
FIG. 18 shows the gene expression profile for Melanoma genes.
Figure 19A:
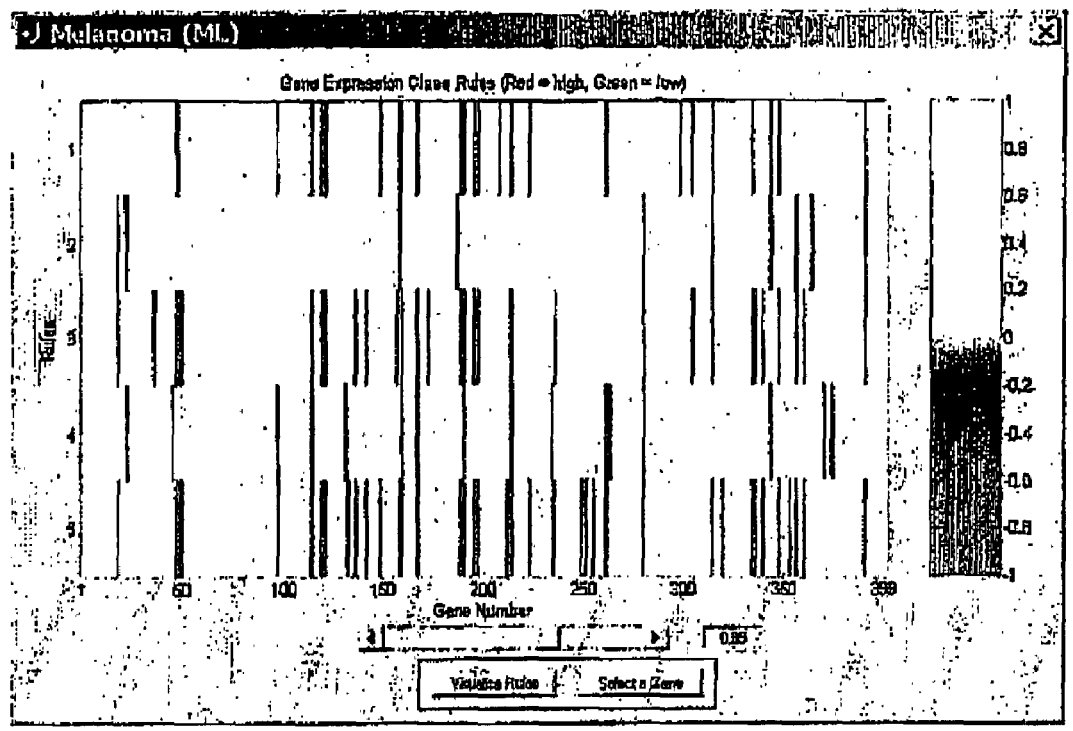
FIGS. 19a and 19b show the 5 gene expression subgroup profiles for Melanoma highlighting underexpression and overexpression respectively.
Figure 19B:
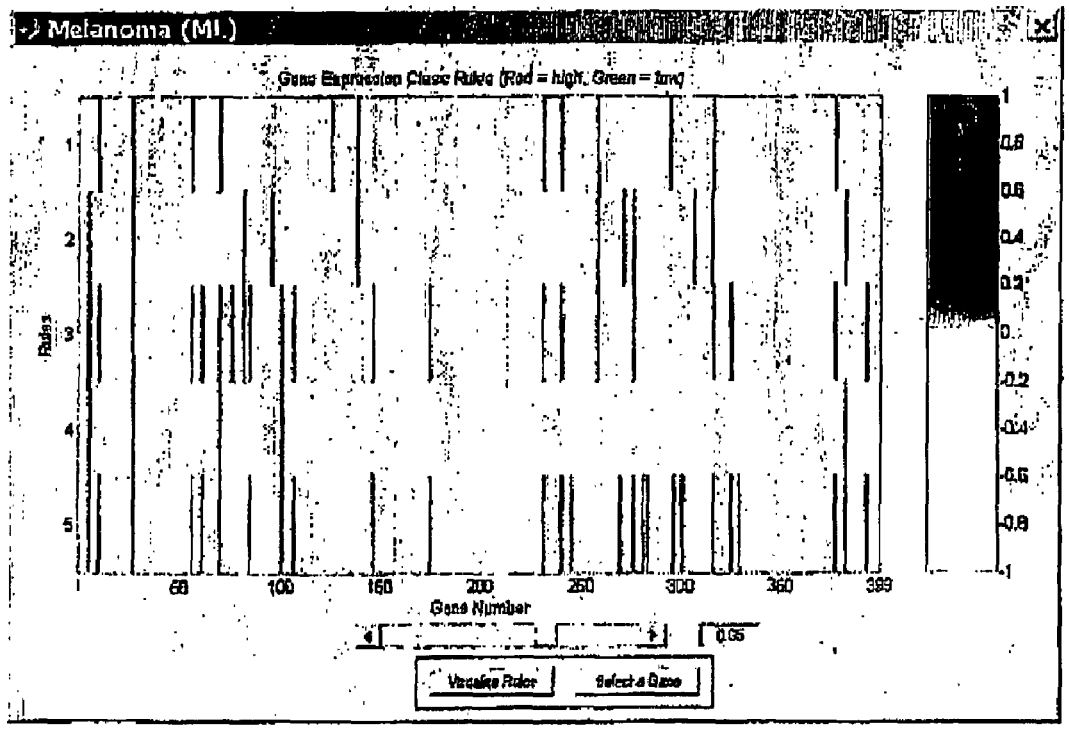

FIG. 18 shows the gene expression profile for Melanoma genes as opposed to the profiles of the other 13 types of cancer considered here. The genes are represented by their GenBank accession number. Genes numbered on the list with the following order numbers are overexpressed: 1,3,4, 5,6,7. Gene 2 is under-expressed. The minimum level of fuzzy membership degree of over-, a under expression is 0.65. FIGS. 19a and 19b show the 5 gene expression subgroup profiles for Melanoma highlighting underexpressed and overexpressed genes respectively.

Figure 20:
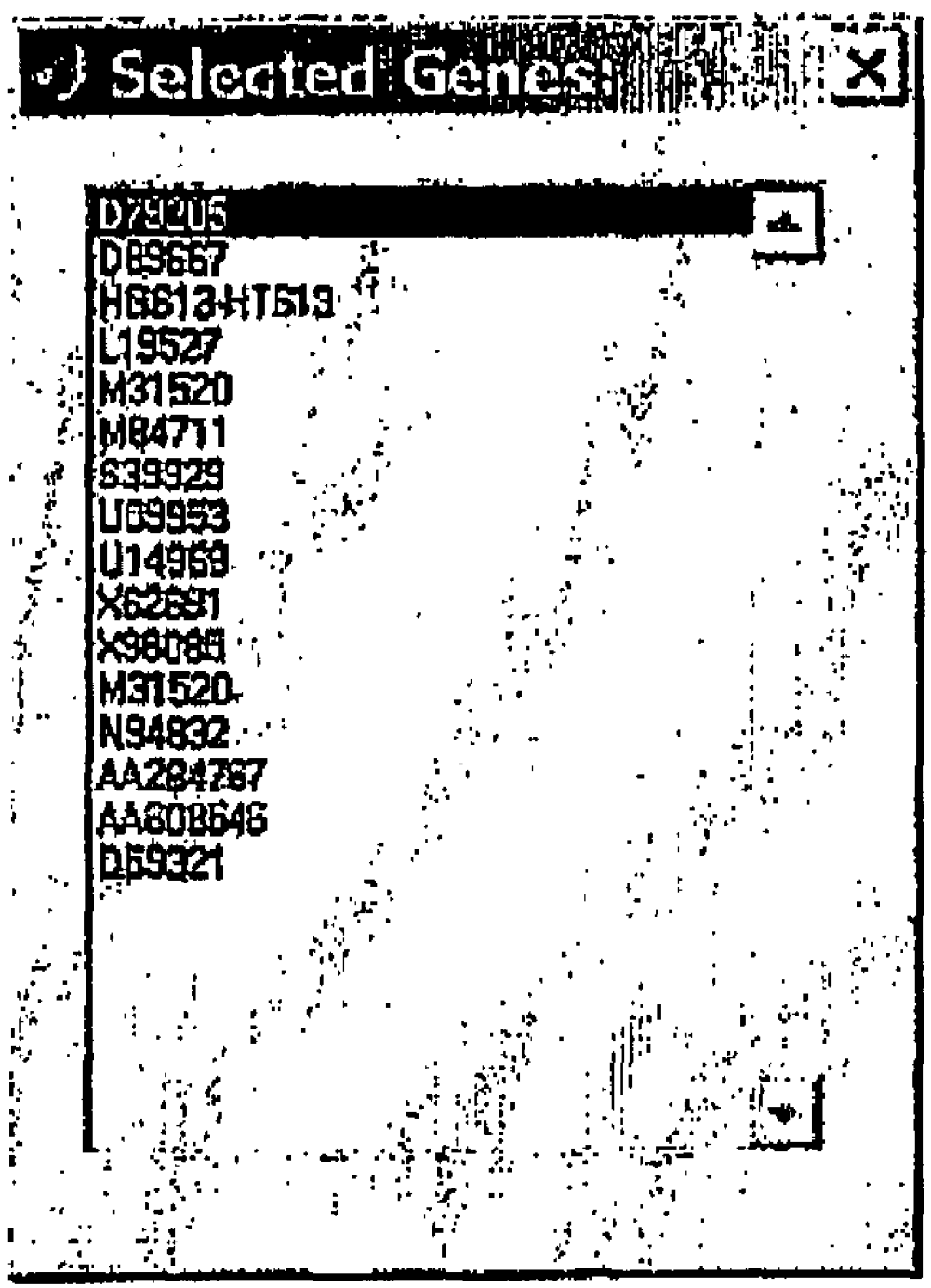
FIG. 20 shows the gene expression profile for Uterine adenocarcinoma genes.
Figure 21A:
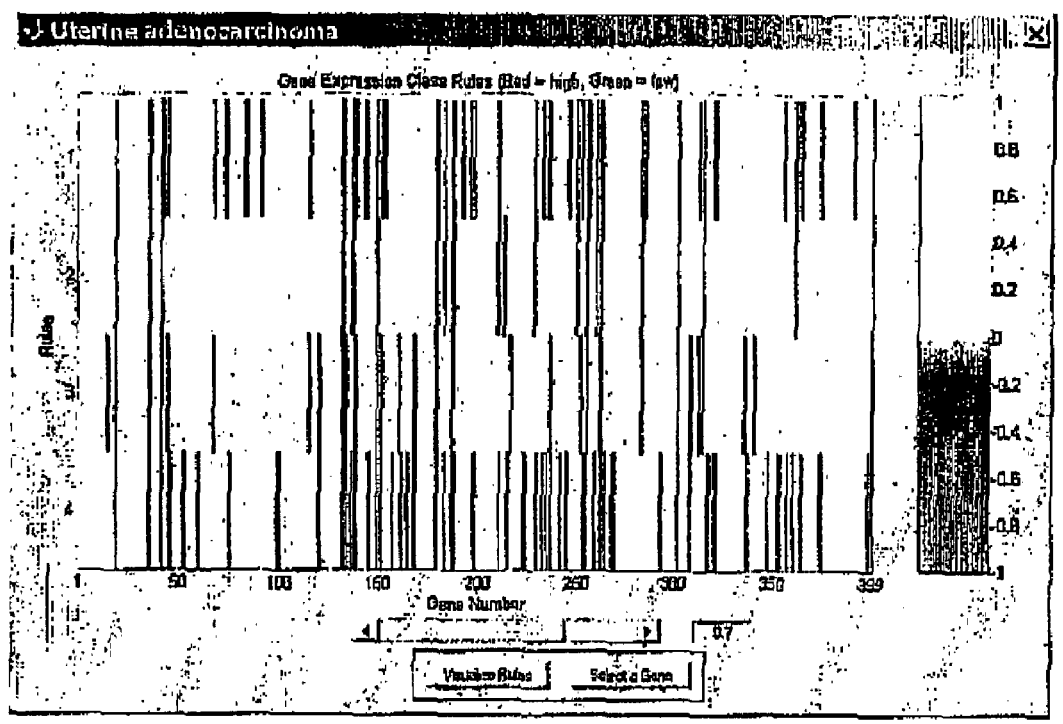
FIGS. 21a and 21b show the 4 gene expression subgroup profiles for Uterine adenocarcinoma highlighting underexpression and overexpression respectively.
Figure 21B:
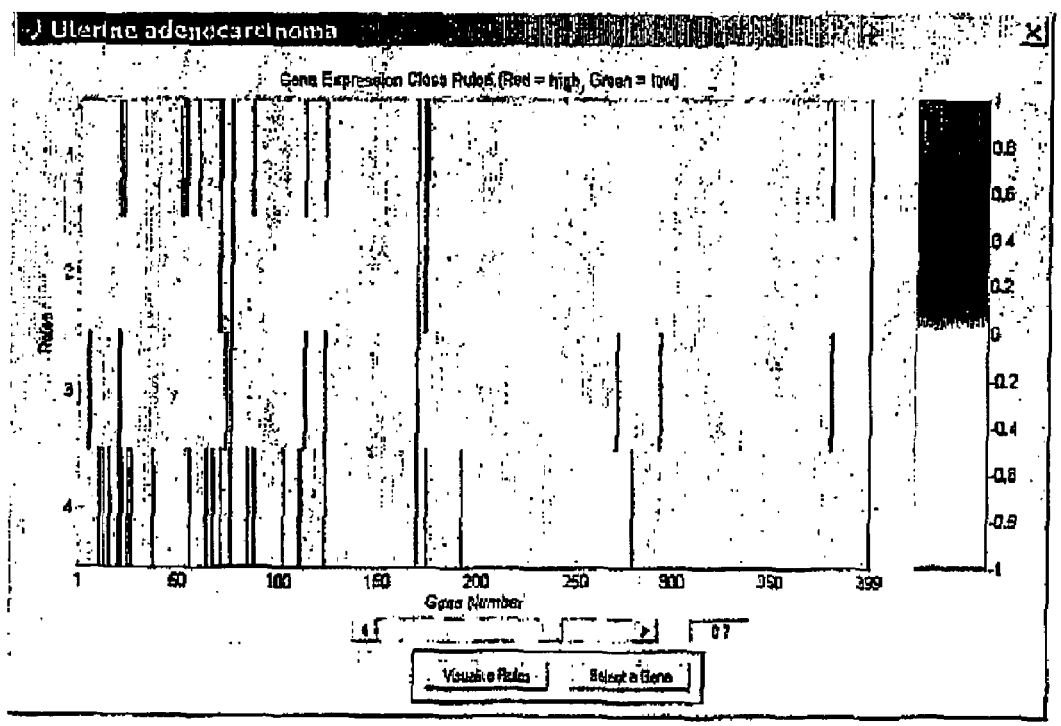

FIG. 20 shows the gene expression profile for Uterine adinocarcinoma genes as opposed to the profiles of the other 13 types of cancer considered here. The genes are represented by their GeneBank accession number. Genes numbered on the list with the following order numbers are overexpressed 1,2,3,5,6,8,9,10. Te rest of the genes on the list below are under-expressed. The minimum level of fuzzy member degree of over-, or under expression is 0.65. FIGS. 21a and 21b show the 4 gene expression subgroup profiles for Uterine adenocarcinoma highlighting underexpressed and overexpressed genes respectively. The minimum level of fuzzy membership degree of over-, or under expression in 0.7.

Figure 22:
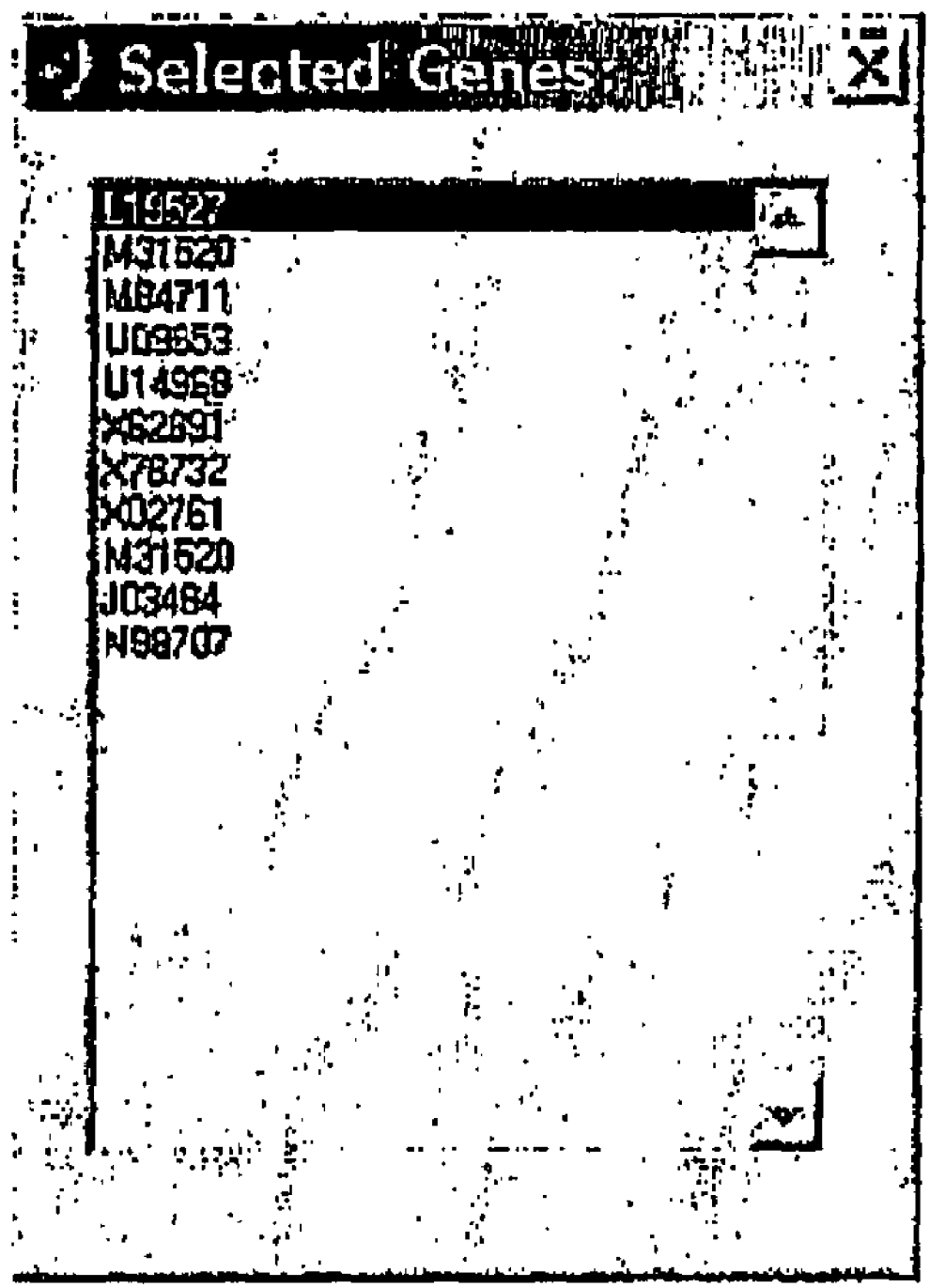
FIG. 22 shows the gene expression profile for Leukemia genes.
Figure 23A:
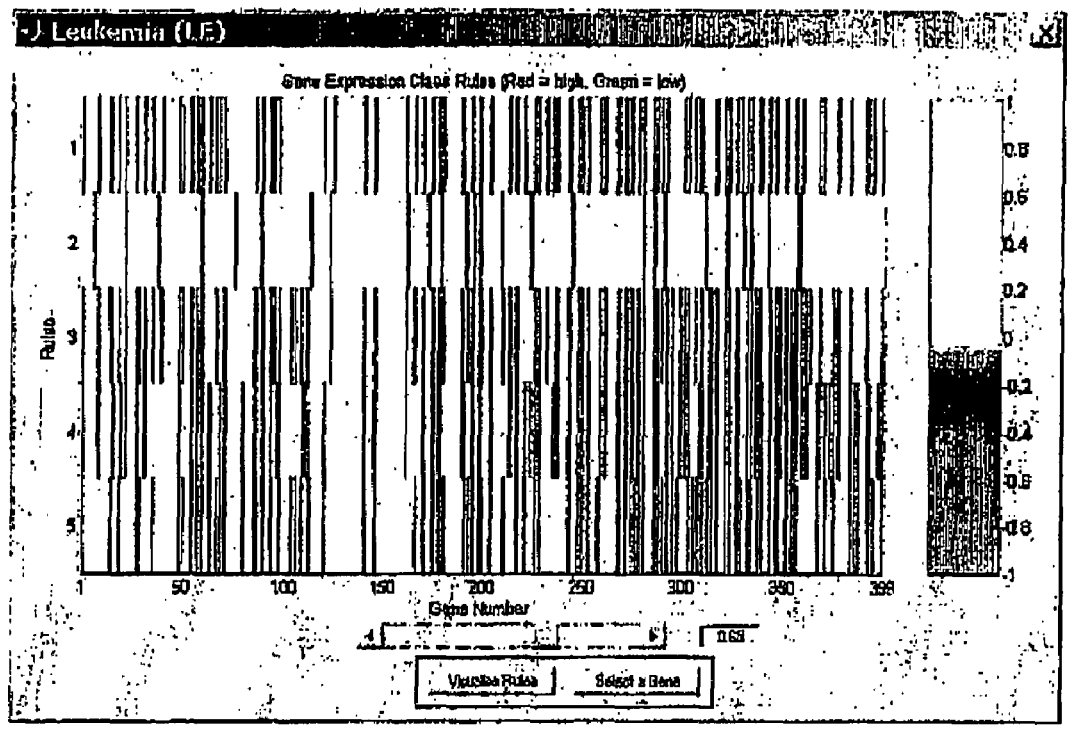
FIGS. 23a and 23b show the 5 gene expression subgroup profiles for Leukemia highlighting underexpression and overexpression respectively.
Figure 23B:
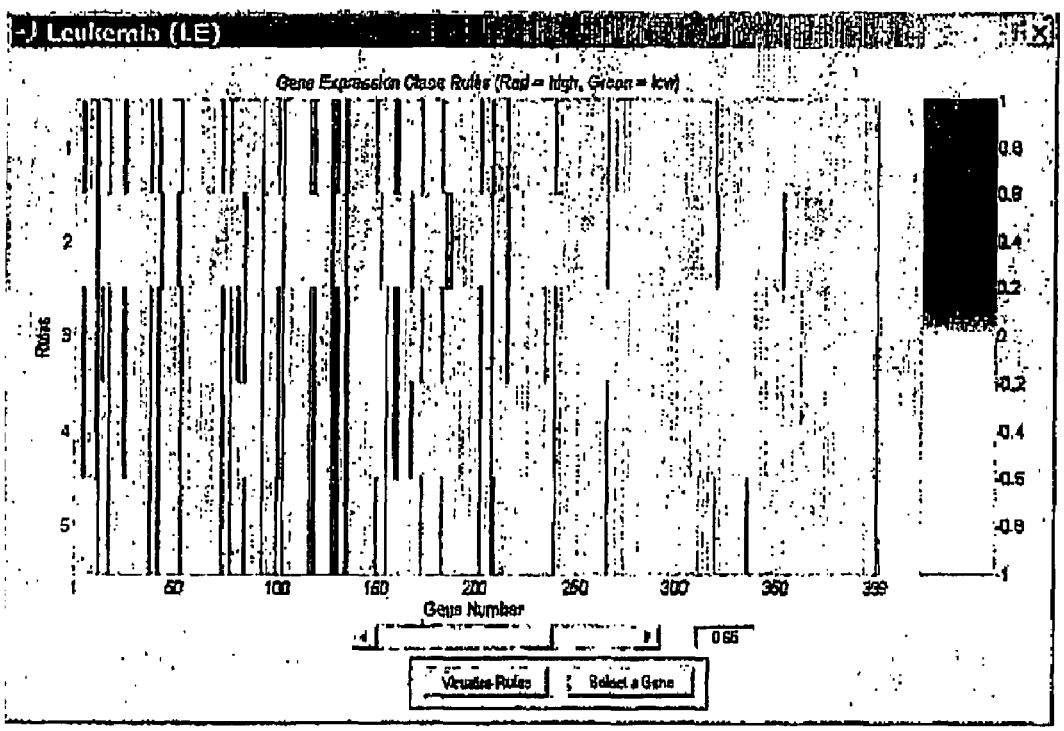

FIG. 22 shows the gene expression profile for leukemia genes as opposed to the profiles of the other 13 types of cancer considered here. The genes am represented by their GeneBank accession number. Gene numbered on the list with the following order numbers are overexpressed: 1,2,3,4,5,6,7,9. The rest of the genes on the list below are under-expressed. The minimum level of fuzzy membership degree of over-, or under expression is 0.65. FIGS. 23a and 23b show the 5 gene expression subgroup profiles for leukemia highlighting underexpressed and overexpressed genes respectively.

Figure 24:
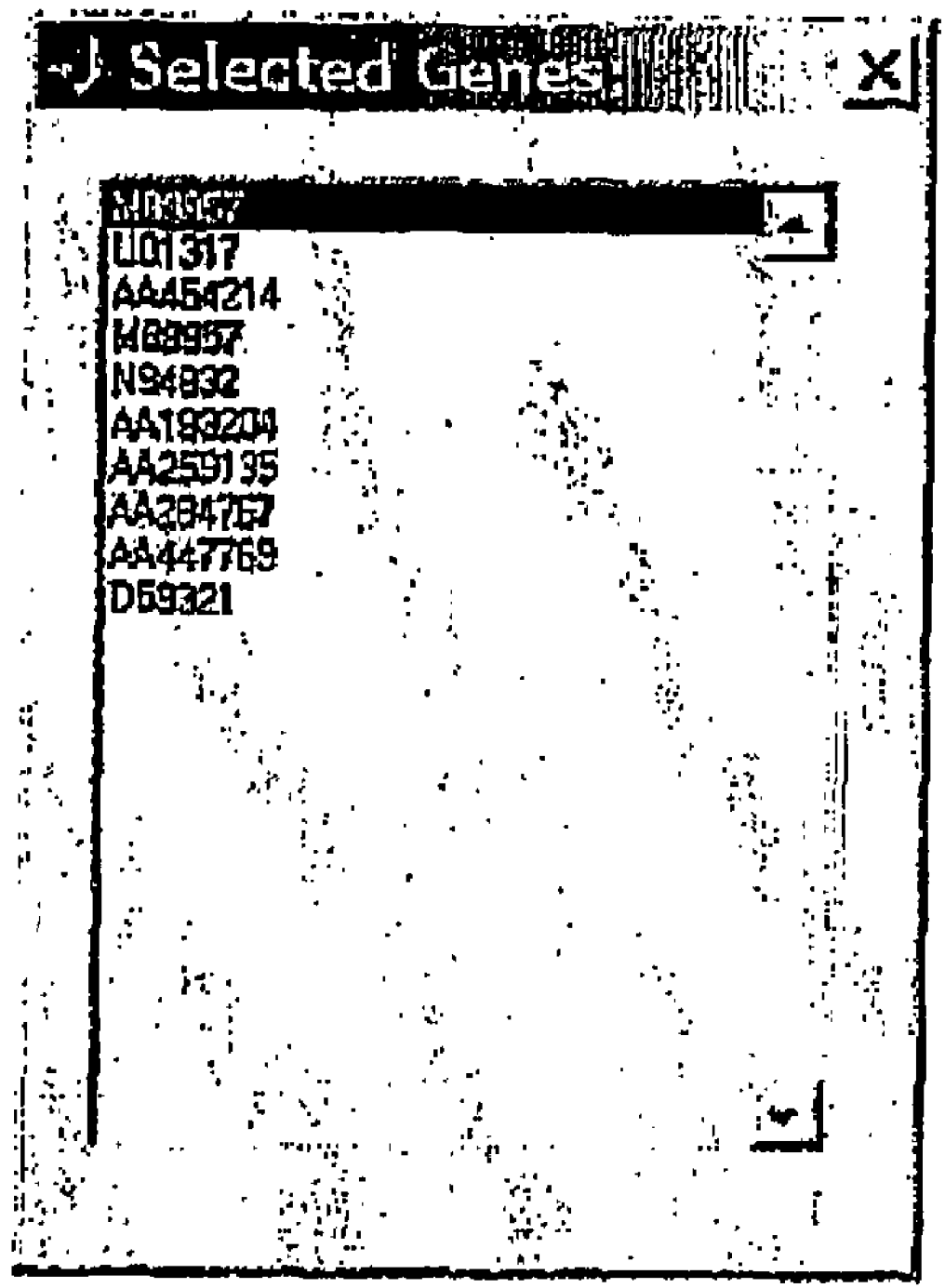
FIG. 24 shows the gene expression profile for Renal cell carcinoma.
Figure 25A:
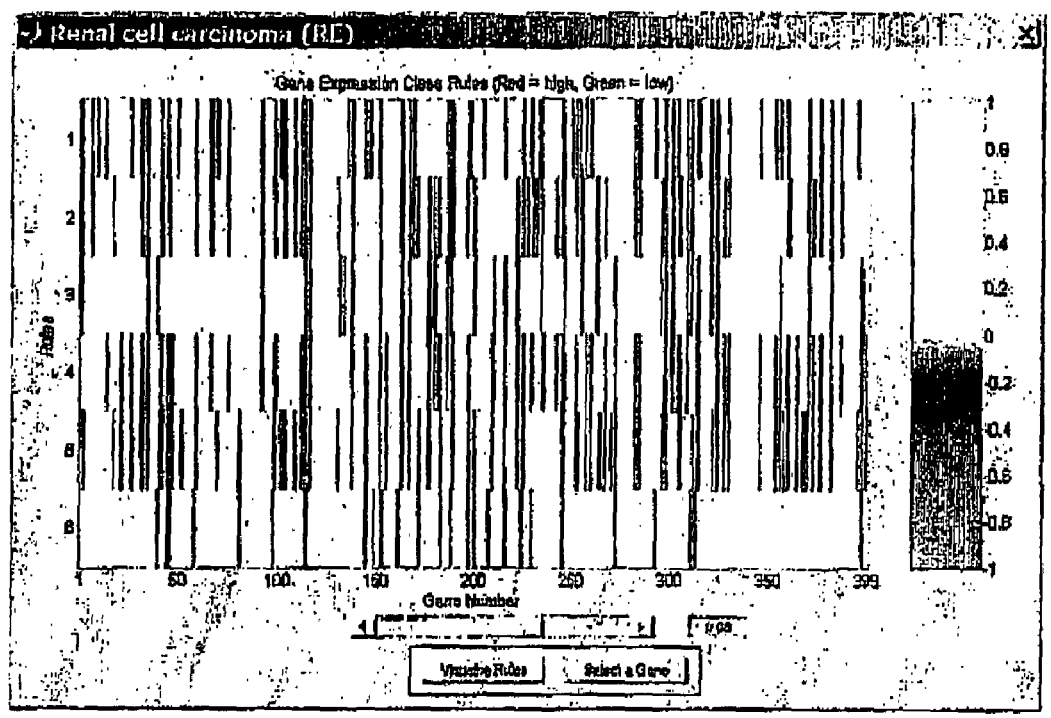
FIGS. 25a and 25b show the 6 gene expression subgroup profiles for Renal cell carcinoma highlighting underexpression and overexpression respectively.
Figure 25B:
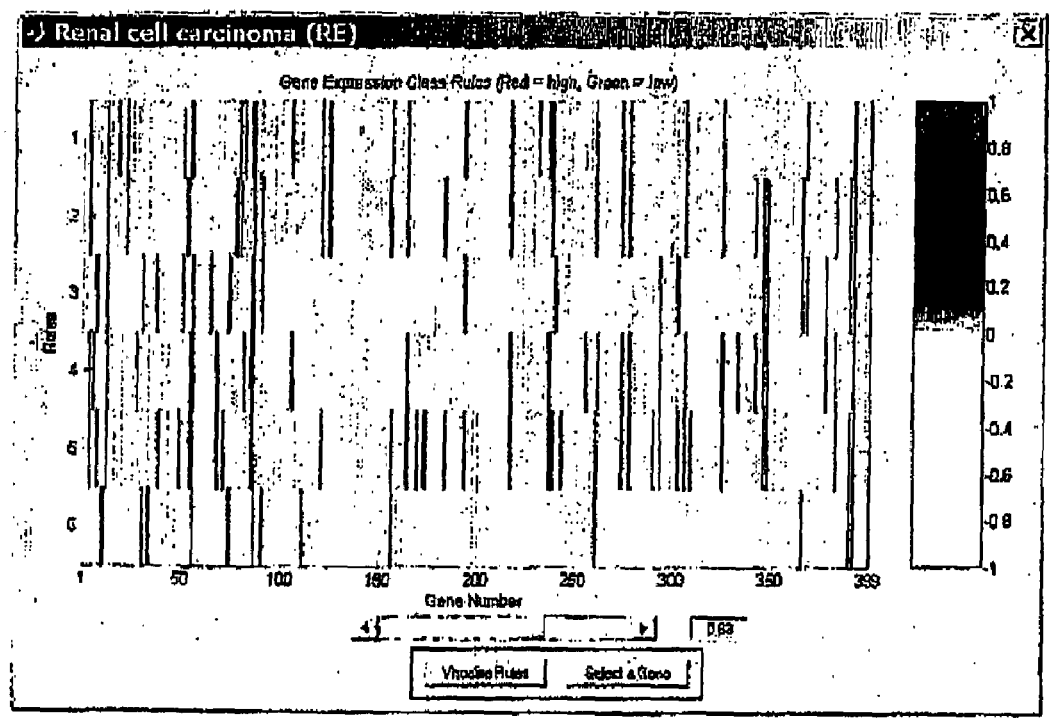

FIG. 24 shows the gene expression profile for Renal cell carcinoma genes as opposed to the profiles of the other 13 types of cancer considered here. The gates are represented by their GeneBank accession number. Genes numbered on the list with the follow order numbers are over expressed: 6,7. The rest of the genes on the list below are under-expressed. Minimum level of fuzzy membership degree of over-, or under expression is 0.63. FIGS. 25a and 25b show the 6 gene expression subgroup profiles for Renal cell carcinoma highlighting underexpressed and overexpressed genes respectively.

Figure 26:
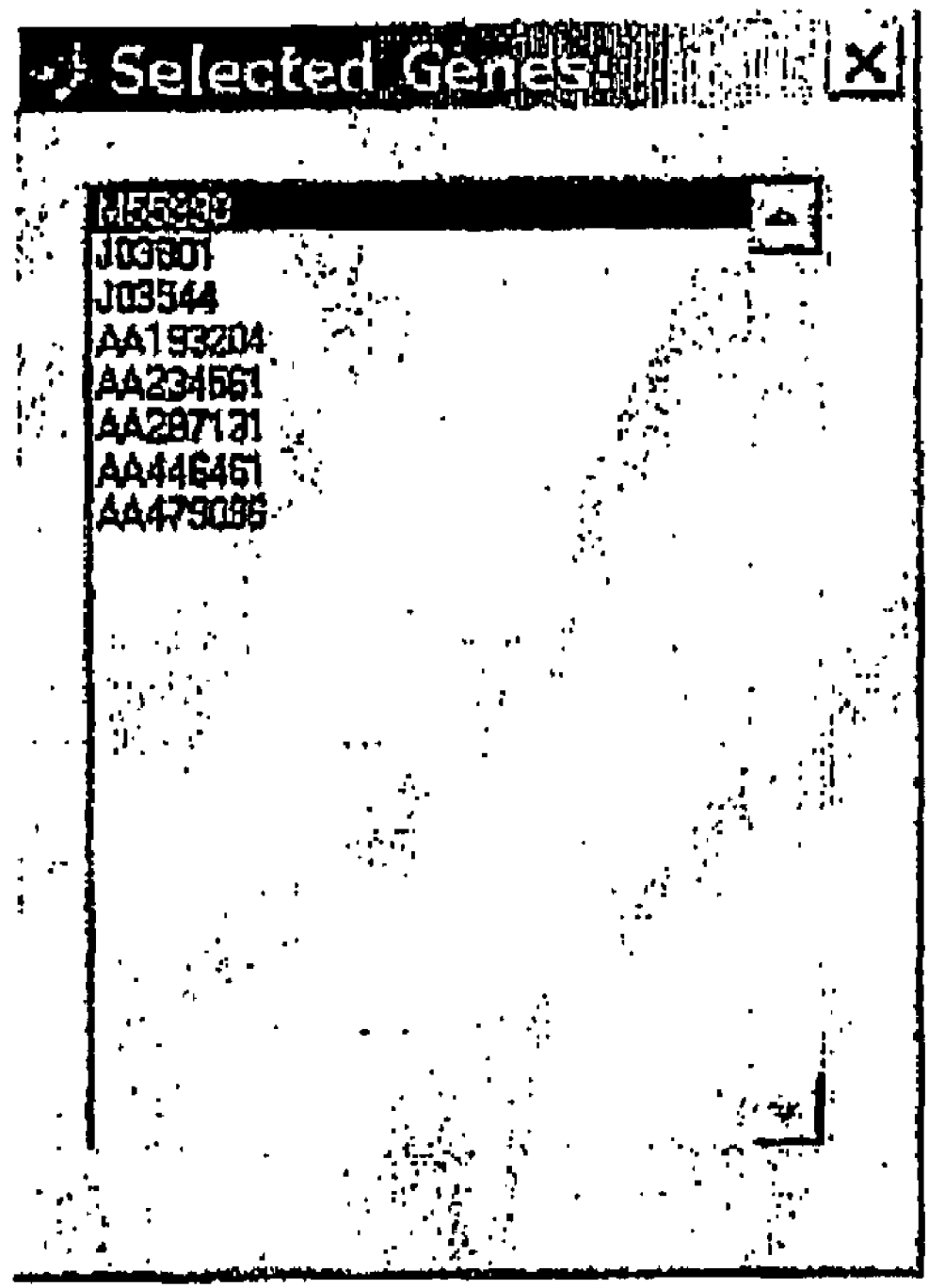
FIG. 26 shows the gene expression profile for Pancreatic adenocarcinoma genes.
Figure 27A:
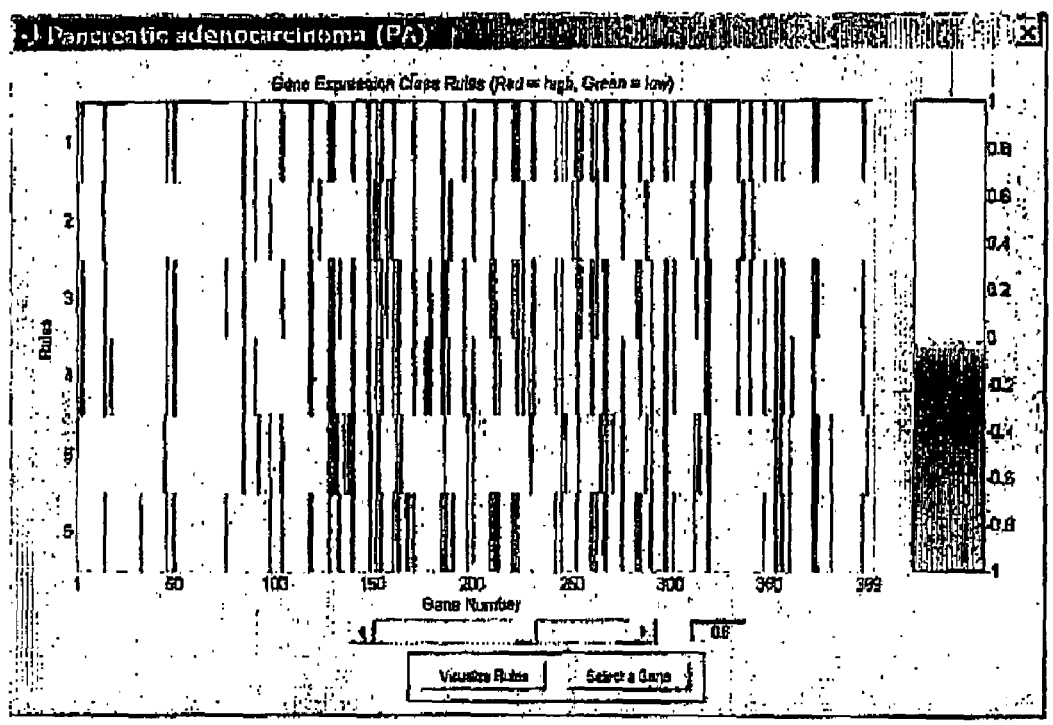
FIGS. 27a and 27b show the 6 gene expression subgroup profiles for Pancreatic adenocarcinoma highlighting underexpression and overexpression respectively.
Figure 27B:
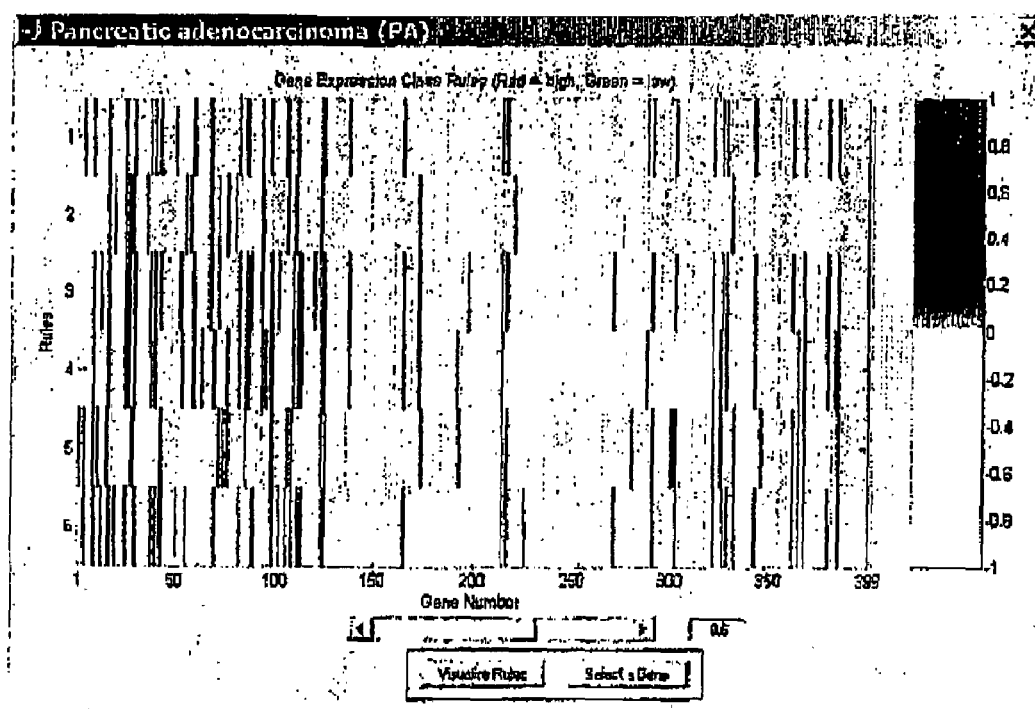

FIG. 26 shows the gene expression profile for Pancreatic adenocarcinoma genes as opposed to the profiles of the other 13 types of cancer considered here. The genes are represented by their GenBank accession number. Genes numbered on the list with the following order numbers are over-expressed 1,2,3,4,5,6,8. The rest of the genes on the list below are under-expressed. Minimum level of fuzzy membership degree of over-, or under expression is 0.6. FIGS. 27a and 27b show the 6 gene expression subgroup profiles for Pancreatic adenocarcinoma highlighting underexpressed and overexpressed genes respectively.

Figure 28:
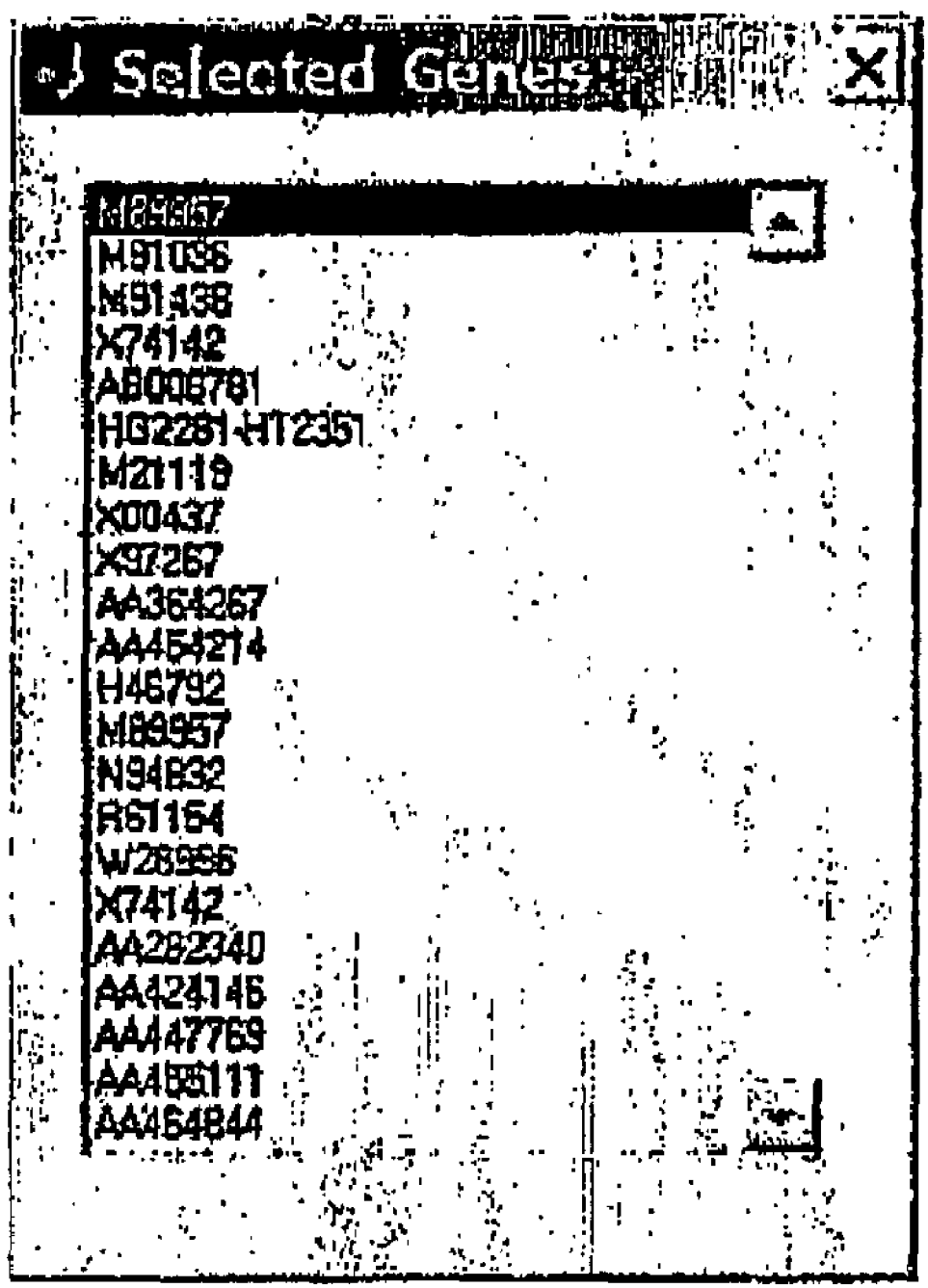
FIG. 28 shows the gene expression profile for Ovarian adenocarcinoma genes.
Figure 29A:
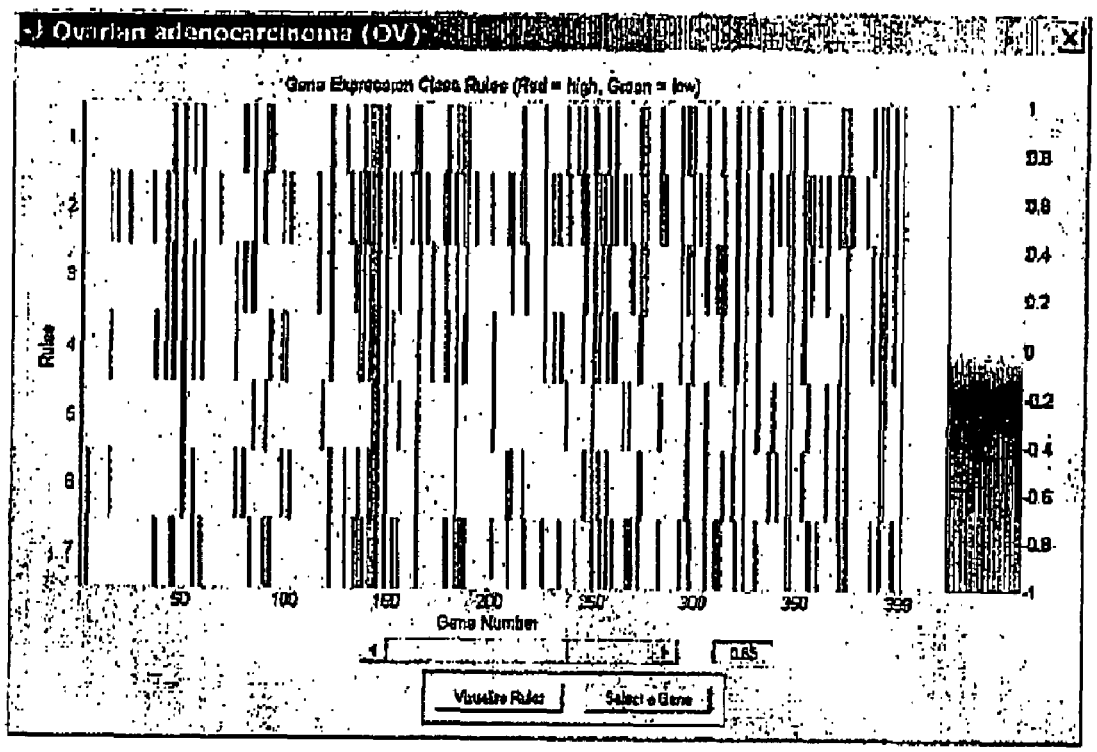
FIGS. 29a and 29b show the 7 gene expression subgroup profiles for Ovarian adenocarcinoma highlighting underexpression and overexpression respectively.
Figure 29B:
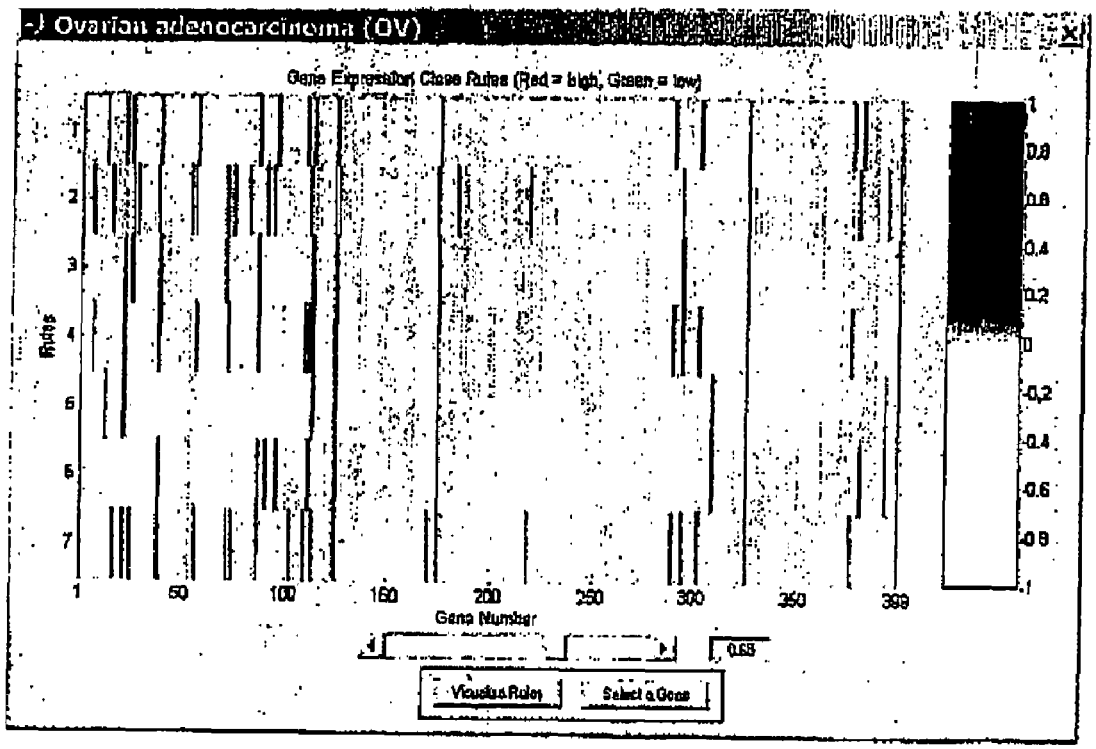

FIG. 28 shows the gene expression profile for Ovarian adenocarcinoma genes as opposed to the profiles of the other 13 types of cancer considered here. Ite genes are represented by their GenBank accession number. Genes numbered on the list with the following order numbers are overexpressed 9. The rest of the genes on the list below are under-expressed. Minimum level of fuzzy membership degree of over-, or under expression is 0.6. FIGS. 29a and 29b show the 7 gene expression subgroup profiles for Ovarian adenocarcinoma highlighting underexpressed and overexpressed genes respectively. The minimum level of fuzzy membership degree of over-, or under expression is 0.65.

Figure 30:
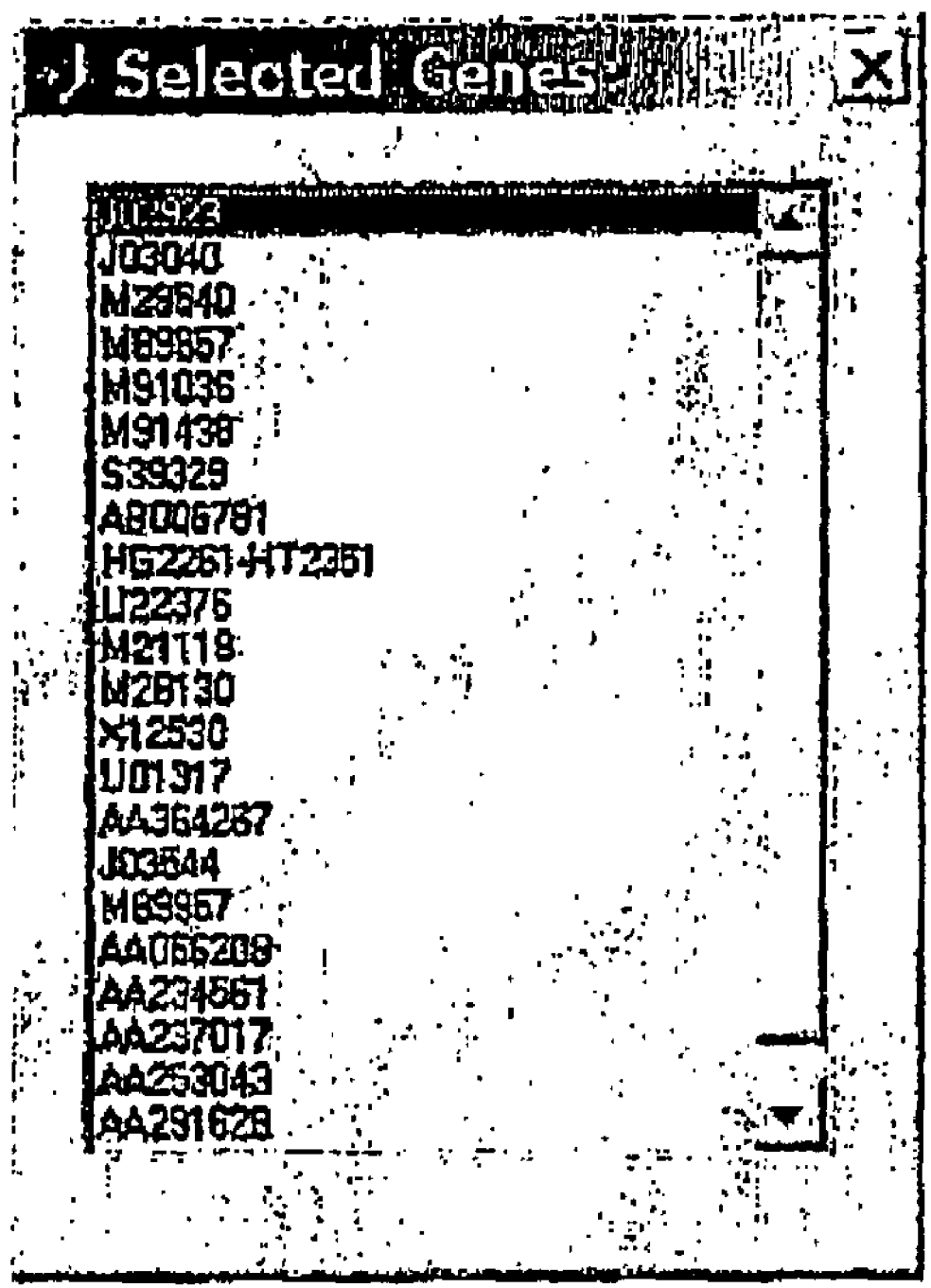
FIG. 30 shows the gene expression profile for Pleural mesothelioma genes.
Figure 31A:
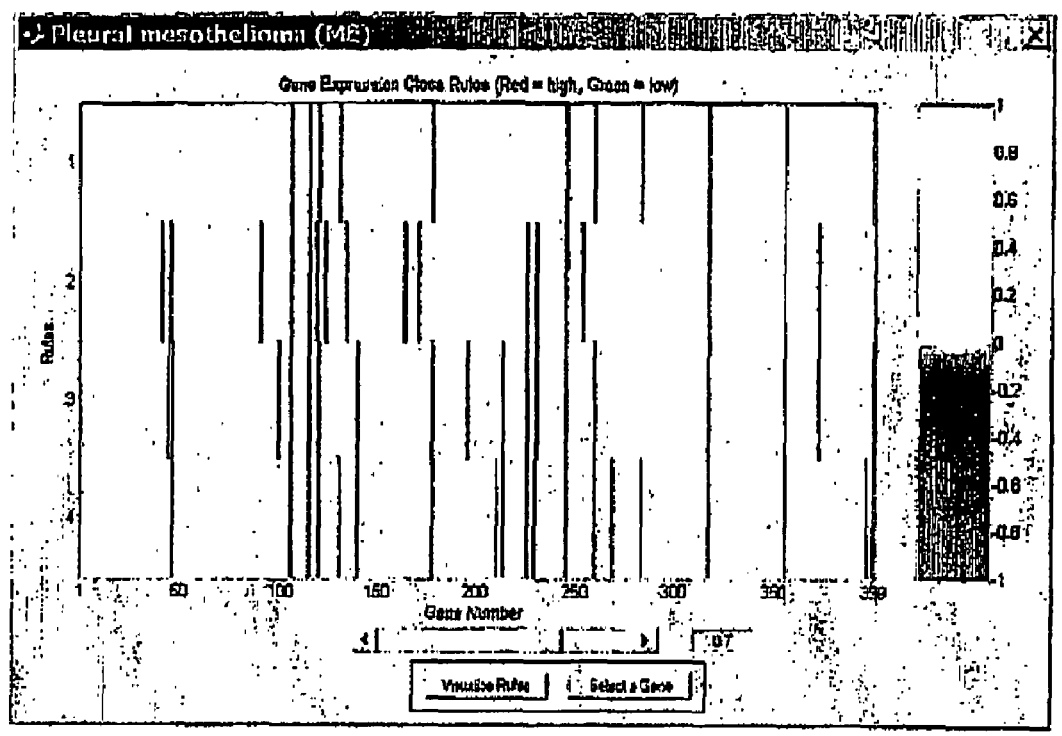
FIGS. 31a and 31b show the 4 gene expression subgroup profiles for Pleural mesothelioma highlighting underexpression and overexpression respectively.
Figure 31B:
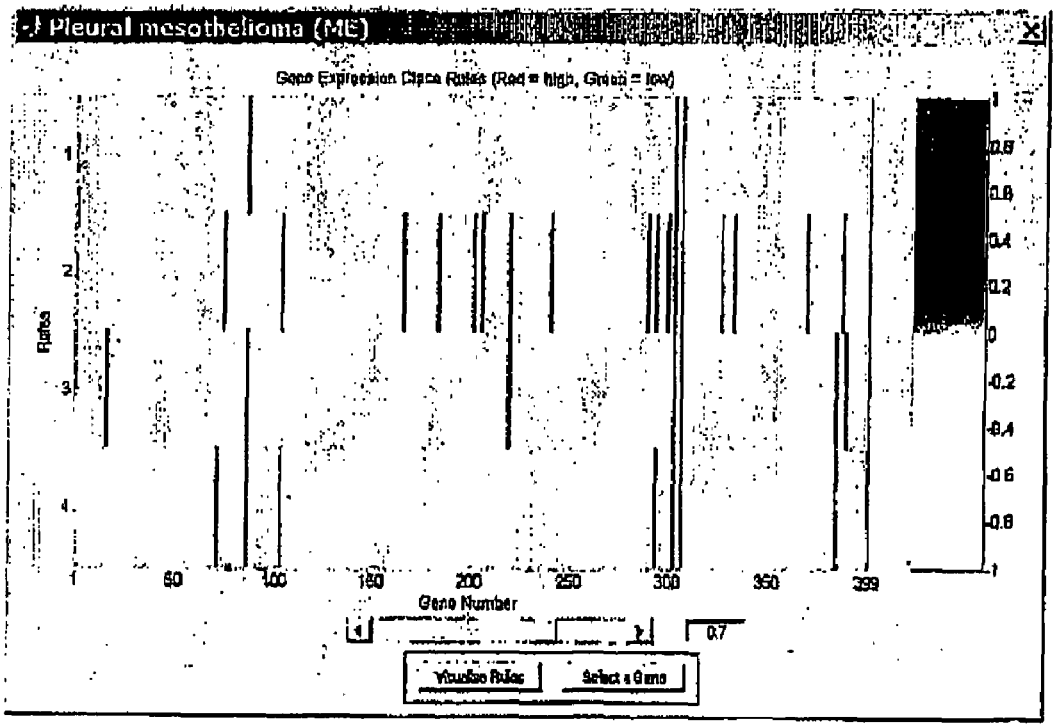

FIG. 30 shows the gene expression profile for Pleural mesothelioma genes as opposed to the profiles of the other 13 types of cancer considered here. The genes are represented by their GenBank accession number. Genes numbered on the list with the following order numbers are over-expressed: 2,13,14,16,17,18,19,20,21. The rest of the genes on the list below are under-expressed. The minimum level of fuzzy membership degree of over-, or under expression is 0.7. FIGS. 31a and 31b show the 4 gene expression subgroup profiles for Pleural mesothelioma highlighting underexpressed and overexpressed genes respectively.

Figure 32:
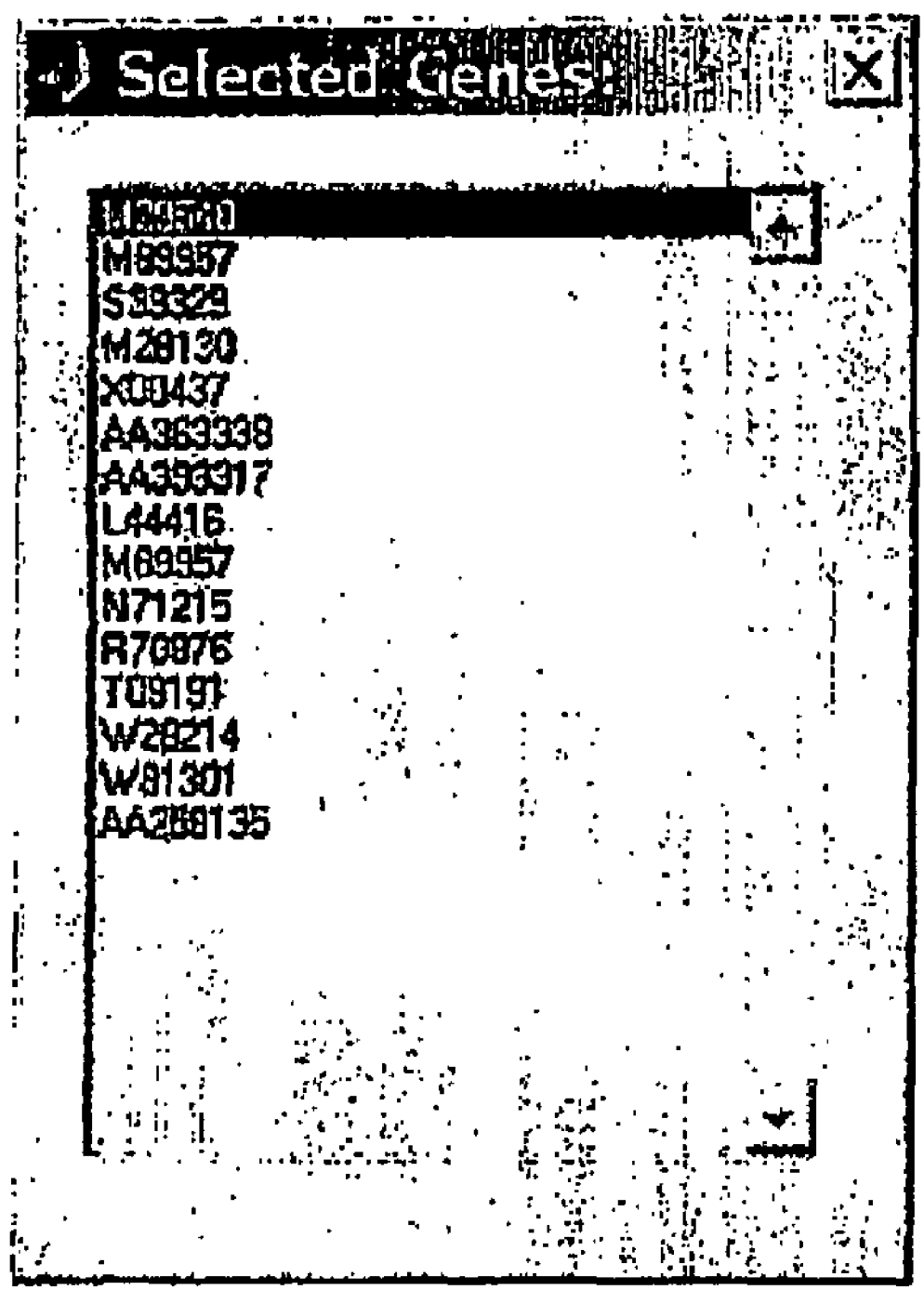
FIG. 32 shows the gene expression profile for the Central nervous system genes.
Figure 33A:
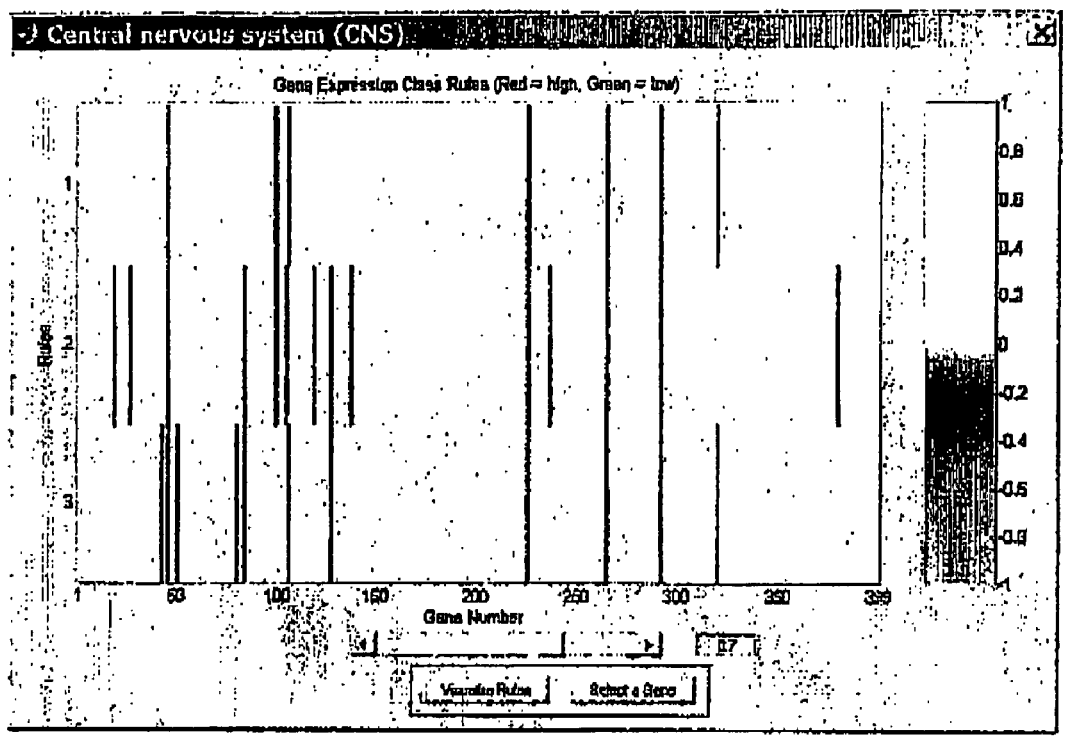
FIGS. 33a and 33b show the 3 gene expression subgroup profiles for Central nervous system cancer highlighting underexpression and overexpression respectively.
Figure 33B:
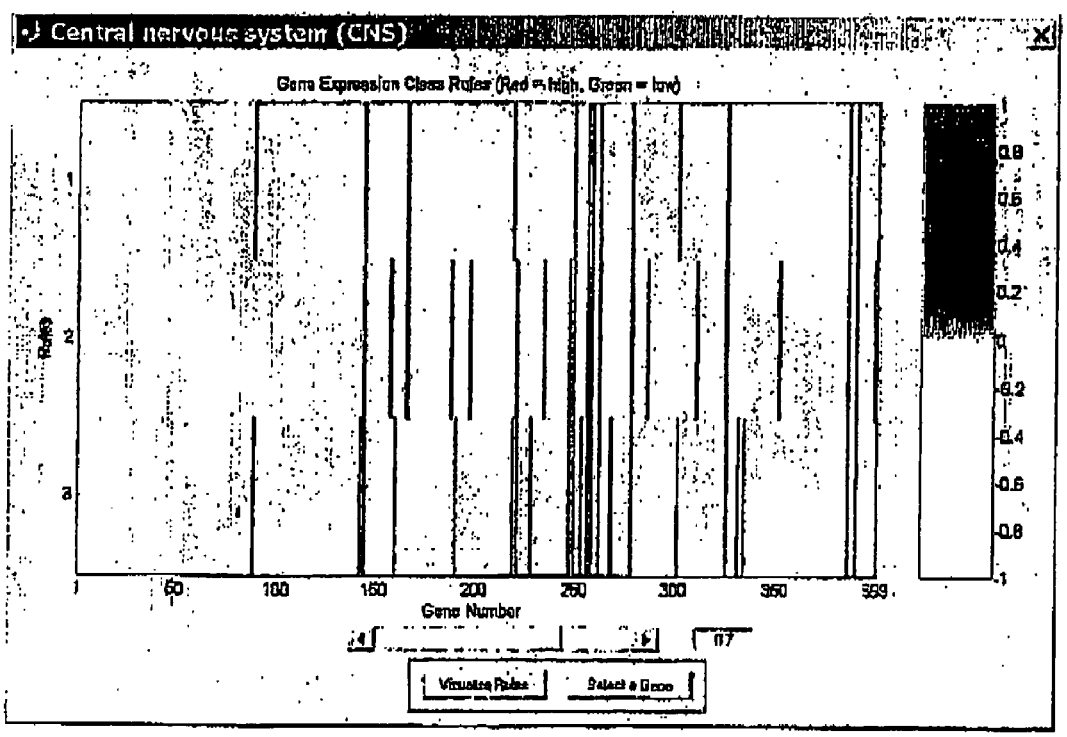

FIG. 32 shows the gene expression profile for the Central nervous system genes as opposed to the profiles of the other 13 types of cancer considered here. The genes are represented by their GenBank accession number. Genes numbered on the list with the following order numbers are overexpressed: 6,7,8,10,11,12,13,14,15. The rest of the genes on the list below are under-expressed. The minimum level of fuzzy membership degree of over-, or under expression is 0.8. FIGS. 33a and 33b show the 3 gene expression subgroup profiles for Central nervous system cancer highlighting underexpressed and overexpressed genes respectively. The minimum level of fuzzy membership degree of over-, or under expression is 0.7.

INDUSTRIAL APPLICABILITY

The neural networks and methods of this invention are useful in diagnosis, management of disease, evaluating efficacy of therapy, producing reagents and test kits suitable for diagnosing diseases or conditions, evaluating drug targets and the development of drugs for the treatment of a variety of diseases and conditions.

THE FOLLOWING PUBLICATIONS ARE INCORPORATED HEREIN BE REFERENCE

S. Dudoit, J. Fridlyand, and T. P. Speed, Comparison of Discrimination Methods for the Classification of Tumors Using Gene Expression Data, *Journal of the American Statistical Association*, vol. 97, no. 457, March, pp. 77-87, 2002.

T. R. Golub, D. K. Slonim, P. Tamayo, C. Huard, M. Gaasenbeek, J. P. Mesirov, H. Coller M. L. Lob, J. R. Downing, M. A. Caligiuri, C. D. Bloomfield, and E. S. Lander, Molecular classification of cancer: class discovery and class prediction by gene expression monitoring, *Science*, vol. 286, 15 October, pp. 531-537, 1999.

J. Khan, J. S. Wei, M. Ringner, L. H. Saal, M. Ladanyi, F. Westermann, F. Berthold, M. Schwab, C. R. Antoneseu, C. Peterson, and P. S. Meltzer, Classification and diagnostic prediction of cancers using gene expression profiling and artificial neural networks, *Nature Medicine*, Nature Publishing Group, vol. 7, no. 6, pp. 673-679, 2001.

N. Kasabov, Evolving Connectionist Systems: Methods and Applications in Bioinformatics, *Brain Study and Intelligent Machine*, Springer Verlag, 2002.

N. Kasabov, Evolving Connectionist Systems for Adaptive On-line Knowledge-Based Learning, *IEEE Transaction of Systems, Man and Cybernetics—part B: Cybernetics*, vol. 31, no. 6, pp. 902-918, 2001.

N. Kasabov, Adaptive method and system, PCT, WO 01/78003 A1.

S. Ramaswamy, P. Tamayo, R. Rifkin, S. Mukherjee, C-H. Yeang, M. Angelo, C. Ladd, M. Reich, E. Latulippe, P. Mesirov, T. Poggio, W. Gerald, M. Loda, E. S. Lander, and T. R. Golub, Multiclass cancer diagnosis using tumor gene expression signatures, *Proceedings of the National Academy of Sciences*, vol. 98, no. 26, pp. 15149-15154, 2001.

F. P. Roth, Bringing out the best features of expression data, *Genome Research*, Cold Spring Harbor Laboratory Press, vol. 11, no-11, pp. 1878-1887, 2001.

M. A. Shipp, K. N. Ross, P. Tamayo, A. P. Weng, J. L. Kutok, R. C. T. Aguiar, M. Gasenbeek, Angelo, M. Reich, G. S. Pinkus, T. S. Ray, M. A. Koval, K. W. Last, A. Norton, T. A. Lister, J. Mesirov, D. S. Neuberg, E. S. Lander, J. C. Aster, and T. R. Golub Diffuse large B-cell lymphoma outcome prediction by gene expression profiling and supervised machine learning, *Nature Medicine*, vol. 8, no. 1, pp. 68-74, 2002.

T. D. Wu, Analysing gene expression data from DNA microarrays to identify candidate genes, *Journal of Pathology*, John Wiley and Sons, Ltd., vol. 195, pp. 53-65, 2001.

C-H. Yeang, S. Ramaswamy, P. Tamayo, S. Mukherjee, K. M. Rifkin, M. Angelo, M. Reich, B. Lander, J, Mesirov, and T. Golub, Molecular classification of multiple tumor types, *Bioinformatics*, Oxford University Press, vol. 17, Suppl. 1, pp. S316-S322, 2001.

The invention claimed is:

1. A neural network system, comprising:
a processor,
a memory device,
an input layer comprising one or more input nodes configured to receive a first set of gene expression data categorized into one or more conditions from groups of subjects having said one or more conditions and to store said data in said memory device;
said input layer further comprising input nodes configured to receive a second set of gene expression data from a biological sample from a patient;
a rule base layer comprising one or more rule nodes;
an adaptive component;
and an output layer comprising one or more output nodes,
said memory device having an evolving connectionist systems (ECOS) program embodied on a computer-readable medium containing a set of instructions for execution by said processor;
where said adaptive component is configured to extract one or more first rules from the rule base layer, said one or more first rules representing relationships between the first set of gene expression data and the one or more conditions;
where each of said rule nodes in said rule base layer has a minimum activation threshold; and
where each of said rule nodes is adapted to become activated when said data satisfies the minimum activation threshold of said rule node;
where said one or more first rules is a criterion for diagnosis or prognosis of a disease condition in a patient; and
said program containing instructions to compare said one or more first rules and a second rule obtained from said second set of gene expression data from said patient to determine whether said patient has a disease condition.

2. The system of claim 1, wherein said ECOS program is an evolving fuzzy neural network (EFuNN) program.

3. The system of claim 1, wherein said fuzzy software program is an evolving classification function (ECF) program.

4. The system of claim 1, where
said adaptive component is configured to aggregate two or more selected rule nodes in said rule base layer based on said input data,
and further comprising an identifier component adapted to identify from the extracted rules over-expressed or under-expressed genes linked to the one or more conditions.

5. The system of claim 4, wherein said identifier component is adapted to identify from the extracted rules genes linked to the one or more conditions.

6. The system of claim 1, further comprising:
a gene expression data reducer that reduces gene expression data; and
a neural network modifier to modify the neural network system so that it accepts the reduced gene expression data as its input layer.

7. The system of claim 1, further comprising:
an adaptive component configured to aggregate two or more selected rule nodes in said rule base layer based on said input data; and
an identifier component adapted to identify from the extracted rules a reduced gene expression set linked to the one or more conditions.

8. The system of claim 1, wherein the instructions further comprise a pruning algorithm that prunes nodes in the rule base layer that do not demonstrate a sufficient link to the one or more prognostic outcomes.

9. The system of claim 1, where said condition is a prognostic outcome.

10. The system of claim 9, wherein said prognostic outcome is of a disease selected from the group consisting of breast adenocarcinoma, prostate adenocarcinoma, lung adenocarcinoma, colorectal adenocarcinoma, lymphoma, bladder transitional cell carcinoma, melanoma, uterine adenocarcinoma, leukemia, diffuse large B-cell lymphoma, renal cell carcinoma, pancreatic adenocarcinoma, ovarian adenocarcinoma, pleural mesothelioma, and central nervous system cancer.

11. The system of claim 1, where said condition is a diagnosis of cancer.

12. The system of claim 11, wherein cancer is selected from the group consisting of breast adenocarcinoma, prostate adenocarcinoma, lung adenocarcinoma, colorectal adenocarcinoma, lymphoma, bladder transitional cell carcinoma, melanoma, uterine adenocarcinoma, leukemia, diffuse large B-cell lymphoma, renal cell carcinoma, pancreatic adenocarcinoma, ovarian adenocarcinoma, pleural mesothelioma, and central nervous system cancer.

13. The system of claim 1, where said program further comprises instructions for:
(a) testing that data using a leave-one out method;
(b) reducing input gene expression data to give a best test accuracy thereby producing reduced gene expression data;
(c) modifying the input layer to accept the reduced gene expression data as its input layer producing a modified neural network module;
(d) training the modified neural network module; and
(e) extracting rules from the adaptive component.

14. A method comprising:
(a) providing a first set of gene expression data categorized into one or more conditions said data obtained for groups of subjects having one or more conditions;
(b) inputting said gene expression data into an input layer in a computer comprising one or more input nodes;
(c) storing said gene expression data in a memory device;
(d) extracting one or more rules from a rule base layer using an ECOS program, said one or more rules representing relationships between the gene expression data and die one or more conditions, where each of said rules meets a minimum activation threshold;
(e) training a neural network system on said gene expression data and said one or more conditions;
(f) determining a first rule relating to said first set of gene expression data;
(g) inputting a second set of gene expression data from a patient;
(h) determining a second rule relating to said second set of gene expression data; and
(j) determining whether second rule is sufficiently similar to said first rule to reach a conclusion about whether said patient has cancer.

15. The method of claim 14, wherein said ECOS program extracts rules using an EFuNN algorithm.

16. The method of claim 15, where said EFuNN algorithm comprises:
(a) start;
(b) optional preprocessing of input data;
(c) train model on existing input-output data;
(d) test model on reduced input data
(e) test model on reduced input data
(f) extract rules from model
(g) if new input data available then go to step (e)
(h) else stop.

17. The method of claim 14, wherein said ECOS program contains is an ECF algorithm.

18. The method of claim 14, where step (d) further comprises:
(d1) aggregating two or more selected rules based on said data;
(d2) identifying from the extracted rules over-expressed or under-expressed genes linked to the one or more conditions.

19. The method of claim 14, where step (d) further comprises:
(d1) aggregating two or more selected rules based on said data;
(d2) identifying from the extracted rules genes representing a reduced gene expression set linked to the one or more conditions.

20. The method of claim 14, further comprising the steps:
testing the data using a leave one out method;
reducing the gene expression data;
modifying the neural network system of step e to accept the reduced gene expression data as its input layer;
training the modified neural network system; and
extracting rules from the adaptive component.

21. The method of claim 17, wherein said ECF algorithm comprises:
(a) inputting a vector from a data set organized into classes of interest;
(b) determining the class of said input vector using a selected vector classification scheme;
(c) if any rule nodes have been already created, calculating distances between the input vector and all rule nodes already created;
(d) if all distances are greater than a max-radius parameter, creating a new rule node, position of said new rule node being the same as the input vector, radius of said new rule node being set to a min-radius parameter, class of said new rule node being determined according to a selected rule node classification scheme, and then proceeding to step a; if all distances are not greater than a max-radius parameter, proceeding to step e;
(e) finding the rule node that is nearest to the input vector;
(f) determining the distance of said input vector from said nearest rule node;
(g) if said distance is less than or equal to said radius of said nearest rule node, and the class of said nearest rule node is the same as the class of said input vector, proceeding to step a, otherwise, proceeding to step h;
(h) if said distance is less than or equal to said radius of said nearest rule node, and the class of said nearest rule node is not the same as the class of said input vector, setting the radius of said nearest rule node equal to the larger of said distance minus said min-radius parameter, and said min-radius parameter;
(i) determining whether setting the radius of said nearest rule node equal to said distance results in a second rule node of a class different from said nearest rule node lying within the area defined by the radius of said nearest rule node;
(j) if no, and if said distance is less than or equal to said max-radius parameter, and the class of said nearest rule node is the same as the class of said input vector, setting the radius of said nearest rule node equal to said distance, otherwise, if all distances are greater than a max-radius parameter, creating a new rule node, position of said new rule node being the same as the input vector, radius of said new rule node being set to a min-radius parameter, class of said new rule node being determined according to a selected rule node classification scheme;
(k) determining whether any vectors remain to be input;
(l) if yes, proceeding to step a, otherwise, stop.

22. The method of claim 21, wherein said selected vector classification scheme of step (b) comprises:
(b1) determining which of the following is true of the location of a vector of interest:
I) location of vector of interest lies within an area defined by the radius of one or more rule nodes all belonging to the same class;
II) location of vector of interest lies within an area defined by the radius of two or more rule nodes not all belonging to the same class;
III) location of vector of interest does not lie within area defined by radius of any rule node;
(b2) if I, setting the class of the vector of interest equal to the class of said one or more rule nodes, and proceeding to step b8, otherwise, proceeding to step b3;
(b3) if II, setting the class of the vector of interest equal to the class of said nearest rule node;
(b4) if III, determining whether class of vector of interest is to be calculated using a one-of-n mode or an m-of-n mode;
(b5) if one-of-n mode is to be used, determining nearest rule node, and setting class of vector of interest equal to class of nearest rule node, or if m-of-n mode is to be used, determining the m nearest rule nodes, separating said m nearest rule nodes according to their respective classes, calculating average distances from vector of interest to rule nodes within each respective class, determining class for which average distance is smallest, and setting class of vector of interest equal to that class.

23. The method of claim 14, further comprising determining whether gene expression data extracted from a biological sample from a patient suspected of having said one or more conditions satisfies a rule representing a relationship between said gene expression data and one or more classes of conditions.

24. The method of claim 23, where said one or more conditions are selected from the group of cancers consisting of breast adenocarcinoma, prostate adenocarcinoma, lung adenocarcinoma, colorectal adenocarcinoma, lymphoma, bladder transitional cell carcinoma, melanoma, uterine adenocarcinoma, leukemia, diffuse large B-cell lymphoma, renal cell carcinoma, pancreatic adenocarcinoma, ovarian adenocarcinoma, pleural mesothelioma, and central nervous system cancer.

25. The method of claim 14, where said gene expression data is obtained for dystrophin related protein, protein kinase C gamma, MINOR/NOR1, PDE4B, Protein kinase beta-1 and Zink-finger protein C2H2-150.

26. The method of claim 14, wherein said gene expression data for breast adenocarcinoma is obtained for the genes S39329, U89942, Z15880, AB006781, HG2261-HT2351, M21119, M28130, U01317, AA454214, H08939, W26436, AA071089, AA236458, AA262710, AA284787, AA447769, AA449419, AA452928, AA453034, AA479299, AA488178 and D59321.

27. The method of claim 14, wherein said gene expression data for prostate cancer is obtained for the genes U01317, AA364167, AA427468, AA428172, AA482319, AA0171646, AA070437, AA193204, AA234561, AA237017, AA259135, AA291629, AA405049, AA437235, AA453304, AA479096, AA482224 and AA599931.

28. The method of claim 14, wherein said gene expression data for lung adenocarcinoma is obtained for genes M89957, M91438, S39329, X15880, M21119, X00437, AA283620, AA364267, AA428172, AA45421, H46792, M89957, W26996, AA088851, AA193204, AA236458, AA447769, AA460849 and D59321.

29. The method of claim 14, wherein said gene expression data for colorectal adenocarcinoma is obtained for genes D83735, L19527, M22632, M25280, M62302, M84711, M91036, U09953, U14968, M62691, U01317, AA454214, H46732, M62302, N34832, N98707, AA161292, AA165369, AA447769, AA452928, AA453034 and AA599991.

30. The method of claim 14, wherein said gene expression data for lymphoma is obtained for genes D64124, M91036 J03801, AA454214, H46792, J03544, N94832, R10770, AA005262, AA024658, AA284767, AA348466 and AA44169.

31. The method of claim 14, wherein said gene expression data for bladder transitional cell carcinoma is obtained for genes X15880, AA056208, AA070437, AA071089 and AA479096.

32. The method of claim 14, wherein said gene expression data for melanoma is obtained for genes D79205, L44416, AA01746, AA026054, AA056208, AA233257 and AA259135.

33. The method of claim 14, wherein said gene expression data for uterine adenocarcinoma is obtained for genes D79205, D89667, HG613-HT613, L19527, M31520, M84711, S39329, U09953, U14968, X62691, X98085, M31520, N94832, AA284767, AA608546 and D59321.

34. The method of claim 14, wherein said gene expression data for leukemia is obtained for genes L19527, M31520, M84711, U09953, U14968, X62691, X78732, X02761, M31520, J 303464 and N98707.

35. The method of claim 14, wherein gene expression data for renal cell carcinoma is obtained for genes M88957, U01317, AA454214, M89957, N94832, AA193204AA259135, AA284767, AA47769 and D59321.

36. The method of claim 14, wherein gene expression data for pancreatic adenocarcinoma is obtained for genes M55998, J03901, J03544, AA193204, AA234561, AA287131, AA446461 and AA479096.

37. The method of claim 14, wherein gene expression data for ovarian adenocarcinoma is obtained for genes M89857, M91036, M91438, X74142, AB006781, HG2261-HT2351, M21119, X00437, X97267, AA364267, AA454214, H46792, M89957, N94832, R61154, W26996, X74142, AA262340, AA424146, AA447769, AA455111 and AA464844.

38. The method of claim 14, wherein gene expression data for pleural mesothelioma is obtained for genes J02923, J03040, M29540, M89957, M91036, M91438, S39329, AB006781HG2261-HT2351, U22376, M21119, M28130, X12530, U01317, AA364267, J03544, M89957, AA056208, AA234561, AA237017, AA253043 and AA291629.

39. The method of claim 14, wherein said gene expression data for central nervous system is obtained for genes M29540, <89957, S39329, M28130, X00437, AA363338, AA393317, L44416, M89957, N17215, R70976T09191, W28214, W81301 and AA259135.

40. The method of claim 14, wherein gene expression data for diffuse large B-cell lymphoma is obtained for genes KIAA0278, gene encoding prepro form of corticotrophin releasing factor, dopamine beta-hydroxylase (dopamine beta-monooxygenase), SP4 trancription factor, CCAAT BOX-BINDING TRANSCRIPTION FACTOR 1, LIM domain protein CLP-36 mRNA, CES2 Carboxylesterase 2 (liver), KIAA0197, LYZ (lysozyme), ApM2 mRNA for GS2374, HPrp18 mRNA, KIAA0036, D-aspartate oxidase, Partial mRNA for pyrophosphatase and JNK activating kinase (JNKK1) mRNA.

* * * * *